United States Patent
Moore

(10) Patent No.: US 7,316,912 B2
(45) Date of Patent: Jan. 8, 2008

(54) TYROSYLPROTEIN SULFOTRANSFERASES AND METHODS OF USE THEREOF

(75) Inventor: Kevin L. Moore, Oklahoma City, OK (US)

(73) Assignee: Siwa Biotech Corporation, Oklahoma City, OK (US)

(*) Notice: Subject to any disclaimer, the term of this patent is extended or adjusted under 35 U.S.C. 154(b) by 0 days.

(21) Appl. No.: 11/336,497

(22) Filed: Jan. 20, 2006

(65) Prior Publication Data

US 2006/0115859 A1 Jun. 1, 2006

Related U.S. Application Data

(63) Continuation of application No. 10/201,525, filed on Jul. 22, 2002, now Pat. No. 7,029,890, which is a continuation-in-part of application No. 09/785,343, filed on Feb. 16, 2001, now Pat. No. 6,605,455, which is a continuation-in-part of application No. 09/374,493, filed on Aug. 13, 1999, now Pat. No. 6,204,016, which is a continuation-in-part of application No. PCT/US99/16750, filed on Jul. 23, 1999, which is a continuation-in-part of application No. 09/150,133, filed on Sep. 9, 1998, now Pat. No. 6,060,295.

(60) Provisional application No. 60/072,994, filed on Jan. 29, 1998.

(51) Int. Cl.
C12Q 1/48 (2006.01)
C12P 21/06 (2006.01)

(52) U.S. Cl. .................. 435/15; 435/69.1; 435/69.2; 435/193; 536/23.2

(58) Field of Classification Search .............. 435/69.1, 435/69.2, 193, 15; 536/23.2
See application file for complete search history.

(56) References Cited

U.S. PATENT DOCUMENTS

| | | | |
|---|---|---|---|
| 5,032,519 A | 7/1991 | Paulson et al. | |
| 5,541,095 A | 7/1996 | Hirschberg et al. | |
| 5,714,594 A | 2/1998 | Weinshilboum et al. | |
| 5,728,819 A | 3/1998 | Jacobs et al. | |
| 6,060,295 A | 5/2000 | Moore | |
| 6,071,732 A | 6/2000 | Moore | |
| 6,204,016 B1 | 3/2001 | Moore | |
| 6,207,414 B1 | 3/2001 | Moore | |
| 6,207,432 B1 | 3/2001 | Moore | |
| 6,605,455 B1 | 8/2003 | Moore | |
| 7,029,890 B2 * | 4/2006 | Moore | 435/193 |

FOREIGN PATENT DOCUMENTS

| WO | WO 97/32889 | 9/1997 |
|---|---|---|
| WO | WO 99/01756 | 1/1999 |

OTHER PUBLICATIONS

Baeuerle et al., "Tyrosine Sulfation Is a *trans*-Golgi-Specific Protein Modification", The Journal of Cell Biology, 105(6):2655-2664, Dec. 1987.
Beisswanger et al., "Existence of distinct tyrosylprotein sulfotransferase genes; Molecular characterization of tyrosylprotein sulfotransferase-2", Proc. Natl. Acad. Sci., vol. 95, pp. 11134-11139, Sep. 1998. (XP-002111842).
Beisswanger et al., "Existence of distinct tyrosylprotein sulfotransferase genes; Molecular characterization of tyrosylprotein sulfotransferase-2", Proc. Natl. Acad. Sci., vol. 95, pp. 11134-11139, Sep. 1998. (XP-002126086).
Bennett, "*Homo sapiens* mRNA for Tyrosyl Sulfotransferase-2", Submitted (May 28, 1998) to the EMBL/GenBank/DDBJ databases., Hist. Lab., 24.5.33, School of Dentistry, Noerre Alle; 20, 2200N, Denmark. (May 28, 1998). (XP-002126068).
Breathnach, R. et al., "Organization and expression of eucaryotic split genes coding for proteins," Annu. Rev. Biochem., 50:349-383, (1981).
Bridgeman, "Human DNA Sequence From BAC 445C9 on Chromosome 22q12.1", Submitted (Dec. 2, 1997) to the EMBL/GenBank/DDBJ databases. (XP-002126070).
Bundgaard, J.R. et al., "New consensus features for tyrosine O-sulfation determined by mutational analysis," J. Biol. Chem., 272:21700-21705, (1997).
Dong, J. F. et al., "Tyrosine sulfation of the glycoprotein Ib-IX complex: identification of sulfated residues and effect on ligand binding," Biochemistry, 33:13946-13953, (1994).
Driscoll, W.J. et al., "Proposed active site domain in estrogen sulfotransferase as determined by mutational analysis," Proc. Natl. Acad. Sci. U.S.A., 92:12328-12332, (1995).
Eng, J.K. et al., J. Am. Soc. Mass Spectrom., 5:976-989, (1994).
Ferrari, S. et al., Genomics, 35:367-371, (1996).
Freiberg et al., "Molecular basis of symbiosis between *Rhizobium* and legumes," Nature, vol. 387, pp. 394-401, Mar. 22, 1997.
Friederich et al., "Inhibition of Tyrosine Sulfation in the Trans-Golgi Retards the Transport of a Constitutively Secreted Protein to the Cell Surface", The Journal of Cell Biology, 107(5):1655-1667, Nov. 5, 1988.
Fukuta, M. et al., J. Biol. Chem., 270:18575-18580, (1995).
Hashimoto, Y. et al., J. Biol. Chem., 267:15744-15750, (1992).

(Continued)

Primary Examiner—Tekchand Saidha
(74) Attorney, Agent, or Firm—Knobbe Martens Olson & Bear LLP

(57) ABSTRACT

Tyrosylprotein sulfotransferases and nucleic acids encoding the tyrosylprotein sulfotransferases are described. Dual isotopes of the enzyme and of the nucleic acids encoding said enzymes have been identified in human, mouse and *C. elegans*. The polypeptides and polynucleotides exhibit a wide range of homologies. The polynucleotides can be used to transform or transfect host cells for producing substantially pure forms of the enzyme, or for use in an expression system for post-translational tyrosine sulfation of proteins or peptides produced within the expression system. The enzymes can be used to sulfate peptides or proteins requiring sulfation.

31 Claims, 13 Drawing Sheets

OTHER PUBLICATIONS

Hilbert et al., "Cloning and Expression of the cDNA Encoding the Human Homologue of the DNA Repair Enzyme, *Escherichia coli* Endonuclease III," *Journal of Biological Chemistry*, 272(10):6733-6740, Mar. 7, 1997.

Hilleier et al., "*Homo sapiens* cDNA clone 774175 5' Similar to WP:F42G9.8", Jun. 5, 1997 (XP002111846).

Hilleier et al., "*Homo sapiens* cDNA Clone 625544 5'Similar to WP:F42G9.8 CEO7235", Jan. 19, 1997 (XP002126066).

Hortin, G. et al., *J. Biol. Chem.*, 261:1786-1793, (1986).

Hortin, G. et al., *J. Biol. Chem.*, 262:3082-3085, (1987).

Hortin, G. et al., *J. Biol. Chem.*, 261:15827-15830 (1986).

Hortin, G.L., *Blood*, 76:946-952 (1990).

Hortin, G.L. et al., *Proc. Natl., Acad. Sci. USA*, 86:1338-1342 (1989).

Huttner, *Nature* (London), 299:273-276, (1982).

Huttner et al., "Protein Sulfation On Tyrosine", *Modern Cell Biology*, 6:97-140, 1988.

Kakuta et al., "Conserved Structural Motifs In the Sulfotransferase Famuily", *TIBS*, 23:129-130, Apr. 1998.

Kakuta, Y. et al., *Nature Struct. Biol.*, 4:904-908, (1997).

Kobayashi, M. et al., *J. Biol. Chem.*, 272:13980-13985, (1997).

Kohara, "C. Elegans cDNA Clone yk166c1:5'End, Single Read,"Sep. 13, 1996 (XP-002126072).

Komatsu, K. et al., *Biochemical and Biophysical Research Communications*, vol. 204, No. 3 1178-1185, (1994).

Kozak, M., *Nucl. Acids. Res.*, 15:8125-8148, (1987).

Lane, W.S. et al., *J. Protein Chem.*, 10:151-160, (1991).

Lee, R.W.H. et al., *Proc. Natl. Acad. Sci. USA*, 82:6143-6147, (1985).

Lennon, G. et al., *Genomics*, 33:151-152, (1996).

Leyte, A. et al., *J. Biol. Chem.*, 266:740-746, (1991).

Lin et al., "Characterization of a Tyrosylprotein Sulfotransferase in Human Liver," *Biochem Parmacol.*, 40(3):629-635, Aug. 1, 1990.

Lin et al., "Recognition Of Substrates Bt Tyrosylprotein Sulfotransferase," *The Journal of Biological Chemistry*, 267(5):2876-2879, Feb. 15, 1992.

Marchese, P. et al., *J. Biol. Chem.*, 270:9571-9578, (1995).

Marra et al., "Mus Musculus cDNA Clone 567635 5' Similar to WP:F42G9.8 CEO7235," (XP-002126067), AA183558, Feb. 16, 1997.

Marra et al., "Mus Musculus cDNA Clone 567635 5' Similar to WP:F42G9.8 CE07235," (XP-002126071), AC-AA277588, Apr. 2, 1997.

Marsolais, F. et al., *J. Biol. Chem.*, 270:30458-30463, (1995).

Niehrs et al., "Analysis Of The Substrate Specificity Of Tyrosylprotein Sulfotransferase Using Synthetic Peptides," *The Journal of Biological Chemistry*, 265(15):8525-8532, May 25, 1990.

Niehrs et al., "Conversion of Recombinant Hirudin to the Natural Form by in Vitro Tyrosine Sulfation. Differntial Substrate Specificities of Leech and Bovine Tyrosylprotein Sulfotransferases," *Journal of Biological Chemistry*, 265(16):9314-9318, Jun. 5, 1990.

Niehrs et al., "Protein Tyrosine Sulfation, 1993—An Update," *Chemico-Biological Interactions*, 92:257-271, 1994.

Niehrs et al., "Purification And Characterization Of Tyrosylprotein Sulfotransferase," *The EMBO Journal*, 9(1):35-42, 1990.

Ouyang et al., "Tyrosylprotein Sulfotransferase: Purification and Molecular Cloning of an Enzyme that Catalyzes Tyrosine O-Sulfation, a Common Postranslational Modification of Eukaryotic Proteins," *Proceedings of the National Academy of Sciences of USA*, 95:2896-2901, Mar. 1998, (XP-002111843).

Pouyani, T. et al., *Cell*, 83:333-343, (1995).

Pittman, D.D., *Biochemistry*, 31:3315-3325, (1992).

Rens-Domiano et al., "characterization of Tyrosylprotein Sulfotransferase From Rat Liver and Other Tissues," *The Journal of Biologica Chemistry*, 264(2):899-905, Jan. 15, 1989.

Rosa et al., *J. Biol. Chem.*, 267:12227-12232, (1992).

Sako, D. et al., *Cell*, 83:323-331, (1995).

Shworak, N.W. et al., *J. Biol. Chem.*, 272:28008-28019, (1997).

Skrzypczak-Jankun, E. et al., *J. Mol. Biol.*, 221:1379-1393, (1991).

Stearns, D.J. et al., *J. Biol. Chem.*, 263-826-832, (1988).

Stone, S.R. et al., *Biochemistry*, 25:4622-4628 (1986).

Warden, C.H. et al., *Genomics*, 18:295-307, (1993).

Weinshilboum, R.M. et al., *FASEB J.*, 11:3-14, (1997).

Wilkins et al., "Tyrosine Sulfation of P-selectin Glycoprotein Ligand-1 is Required for High Affinity Binding to P-selectin," *Journal of Biological Chemistry*, 270(39):22677-22680, Sep. 29, 1995.

William et al., "Purification Of Tyrosylprotein Sulfotransferase From Rat Submandibular Salivary Glands," *Archives of Biochemistry and Biophysics*, 338(1):90-96, Feb. 1, 1997.

Wilson et al., "COSMID F42G9.8," Submitted (May 1994) to EMBL/GENBANK/DDBJ Data Banks, Nature 368 (1994), (XP-002126069).

Wilson et al., "2.2 Mb of contiguous nucleotide sequence from chromosome III of C. elegans," *Nature*, vol. 368, pp. 32-38, Mar. 3, 1994.

Ziegler, D.M. et al., *Biochemistry*, 5:2932-2938, (1966).

Wood, T.C. et al., "Human liver thermolabile phenol sulfotransferase: cDNA cloning, expression and characterization." *Biochem Biophys Res Commun.*, 198(3):1119-27, (1994).

\* cited by examiner

MVGKLKQN`LLLACLVISSVTVFYIG`QHAMECHHRIEERSQ 40

PVKLESTRTTVRTGLDLKAŃKTFAYHKDMPLIFIGGVPRS 80

GTTLMRAMLDAHPDIRCGEETRVIPRILALKQMWSRSSKE 120

KIRLDEAGVTDEVLDSAMQAFLLEIIVKHGEPAPYLCNKD 160

PFALKSLTYLSRLFPNAKFLLMVRDGRASVHSMISRKVTI 200

AGFDLNSYRDCLTKWNRAIETMYNQCMEVGYKKCMLVHYE 240

QLVLHPERWMRTLLKFLQIPWŃHSVLHHEEMIGKAGGVSL 280

SKVERSTDQVIKPVNVGALSKWVGKIPPDVLQDMAVIAPM 320

LAKLGYDPYANPPNYGKPDPKIIENTRRVYKGEFQLPDFL 360

KEKPQTEQVE 370

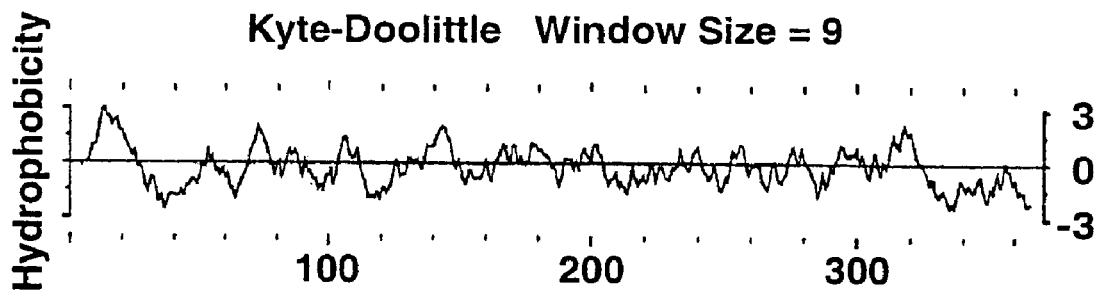

FIGURE 3

```
TPST  MVGKLKQNLLLACLVISSVTVFYLGQHAMECHHRIEERSQPARLENPKATVRAGL.DIKANKTFT.YHKDMPLIF......    73
              **    *****                                        *
EST   ..........................................METSMPEYYE.....VFGEFRGVLMDKRFTKYWEDVEMFLARPDD    40

TPST  ..IGGVPRSGTTLMRA...MLDAHPDIRCGEETRVIPRILALKQMWSRSSKEKIRLDEAGVTDEVLDSAMQAFLLEVIVK    148
         : |:    ||||   |  ::|:| : |:::|:  |  |:|:|      :|: |:| : |   : |:|  |:|::  
EST   LVIATYPKSGTTWISEVVYMIYKEGDVEKCKEDAIFNRIPYL..........................ECRNEDLINGIKQ......LK     97

TPST  HGEPAPYLCNKDPFALKSLTYLARLF.PNAKFLLMVRDGRASVHSMISRKVTIAGF.DLNSYRDCLTKWNRA..........    218
        | |    |  | |:   |: :|  |||:|:|  | ::  :| |:| |: || :|:| ::    |: |
EST   EKESPRIV..KTHLPPKVLP..ASFWEKNCKMIYLCHNAKDVAVSYYFLLMITSYPNKSFSEFVEKFMQGVPYGSWY    173

TPST  ..IETMYNQCMEVGYKKCMLVHYEQLVLHPERWMRTLLKFLHIPWNHSVLHHEEMIGKAGGVSLSKVERSTDQVIKPVNV    296
         |||    |  |   :| ::     |:   |:| :|  |
EST   DHVKAWWEKSKN...SRVLFMFYEDM...KEDIRREVVKLI.....................EFLERKPSAEL..VDRIIQHTSFQEMK    233

TPST  GALSKWVGKIPPDVLQDMAVIAPMLAKLGYDPYANPPNYGKPDPKILENTRRVYKGEFQLPDFLKEKPQTEQVE       370
                                  :|:    :|::   |                  |  ||| | |:|::||
EST   NNPSTNYTMMPEEMMNQK..VSPFMRKGIIGDWKNH................FPEALRERFDEHYKQQ..MKDCTVKFRMEL    295
```

FIGURE 6

```
          Clone              < P   N   Y   A   T   L   T >
Human    810937*      1191  CCCAACTATGGCAACCCTGACC 1211
─  ─  ─  ─  ─     ─  ─  ─  ─     ─  ─  ─  ─  ─
Mouse    569461*      1147  CCCAACTATGGGAACCCCGAC  1167
Human    307478*       482  CCCAACTATGGCAACCCT      499
Human    256487        171  CCCAACTATGGCAACCCTGAC   191
Human    EST86111       43  CCCAACTATGGCAACCCTGAC    63
Human    BAC445C9    33809  CCCAACTATGGCAACCCTGAC  33829
                            < P   N   Y   G   N   P   D >
```

FIGURE 7

MRLSVRR|VLLAAGCALVLVLAVQL|GQQVLECRAVLAGLRS 40

PRGAMRPEQEELVMVGTNHVEYRYGKAMPLIFVGGVPRSG 80

TTLMRAMLDAHPEVRCGEETRIIPRVLAMRQAWSKSGREK 120

LRLDEAGVTDEVLDAAMQAFILEVIAKHGEPAPVLCNKDP 160

FTLKSSVYLSRLFPNSKFLLMVRDGRASVHSMITRKVTIA 200

GFDLSSYRDCLTKWNKAIEVMYAQCMEVGKEKCLPVYYEQ 240

LVLHPRRSLKLILDFLGIAWSDAVLHHEDLIGKPGGVSLS 280

KIERSTDQVIKPVNLEALSKWTGHIPGDVVRDMAQIAPML 320

AQLGYDPYANPPNYGNPDPFVI*NTQRVLKGDYKTPANLK 360

GYFQVNQV*STSSHLGSS 377

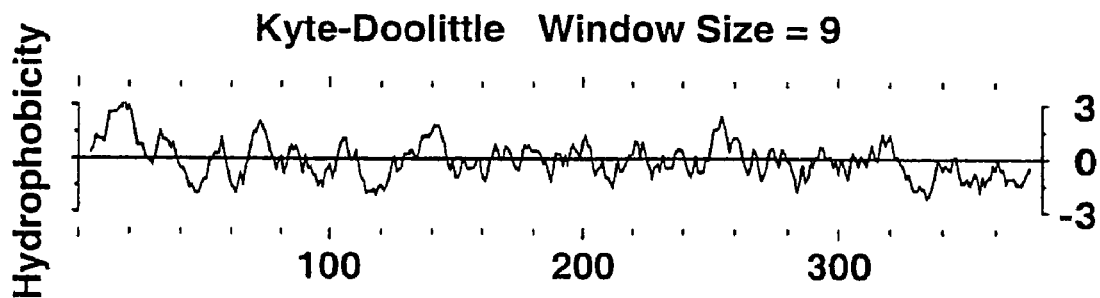

Kyte-Doolittle Window Size = 9

SEQUENCE LISTING

<160> NUMBER OF SEQ ID NOS: 45

<210> SEQ ID NO 1
<211> LENGTH: 370
<212> TYPE: PRT
<213> ORGANISM: Homo sapiens

<400> SEQUENCE: 1

```
Met Val Gly Lys Leu Lys Gln Asn Leu Leu Leu Ala Cys Leu Val Ile
1               5                   10                  15

Ser Ser Val Thr Val Phe Tyr Leu Gly Gln His Ala Met Glu Cys His
                20                  25                  30

His Arg Ile Glu Glu Arg Ser Gln Pro Val Lys Leu Glu Ser Thr Arg
            35                  40                  45

Thr Thr Val Arg Thr Gly Leu Asp Leu Lys Ala Asn Lys Thr Phe Ala
        50                  55                  60

Tyr His Lys Asp Met Pro Leu Ile Phe Ile Gly Val Pro Arg Ser
65                  70                  75                  80

Gly Thr Thr Leu Met Arg Ala Met Leu Asp Ala His Pro Asp Ile Arg
                85                  90                  95

Cys Gly Glu Glu Thr Arg Val Ile Pro Arg Ile Leu Ala Leu Lys Gln
                100                 105                 110

Met Trp Ser Arg Ser Ser Lys Glu Lys Ile Arg Leu Asp Glu Ala Gly
            115                 120                 125

Val Thr Asp Glu Val Leu Asp Ser Ala Met Gln Ala Phe Leu Leu Glu
        130                 135                 140

Ile Ile Val Lys His Gly Glu Pro Ala Pro Tyr Leu Cys Asn Lys Asp
145                 150                 155                 160

Pro Phe Ala Leu Lys Ser Leu Thr Tyr Leu Ser Arg Leu Phe Pro Asn
                165                 170                 175
```

```
Ala Lys Phe Leu Leu Met Val Arg Asp Gly Arg Ala Ser Val His Ser
            180                 185                 190

Met Ile Ser Arg Lys Val Thr Ile Ala Gly Phe Asp Leu Asn Ser Tyr
            195                 200                 205

Arg Asp Cys Leu Thr Lys Trp Asn Arg Ala Ile Glu Thr Met Tyr Asn
            210                 215                 220

Gln Cys Met Glu Val Gly Tyr Lys Lys Cys Met Leu Val His Tyr Glu
225                 230                 235                 240

Gln Leu Val Leu His Pro Glu Arg Trp Met Arg Thr Leu Leu Lys Phe
                245                 250                 255

Leu Gln Ile Pro Trp Asn His Ser Val Leu His Glu Glu Met Ile
            260                 265                 270

Gly Lys Ala Gly Gly Val Ser Leu Ser Lys Val Glu Arg Ser Thr Asp
            275                 280                 285

Gln Val Ile Lys Pro Val Asn Val Gly Ala Leu Ser Lys Trp Val Gly
            290                 295                 300

Lys Ile Pro Pro Asp Val Leu Gln Asp Met Ala Val Ile Ala Pro Met
305                 310                 315                 320

Leu Ala Lys Leu Gly Tyr Asp Pro Tyr Ala Asn Pro Asn Tyr Gly
                325                 330                 335

Lys Pro Asp Pro Lys Ile Ile Glu Asn Thr Arg Arg Val Tyr Lys Gly
            340                 345                 350

Glu Phe Gln Leu Pro Asp Phe Leu Lys Glu Lys Pro Gln Thr Glu Gln
            355                 360                 365

Val Glu
    370

<210> SEQ ID NO 2
<211> LENGTH: 1768
<212> TYPE: DNA
<213> ORGANISM: Homo sapiens

<400> SEQUENCE: 2
gtagactgtc catggcctga acattttccg aaaatcattt tgagcaaaat atctgtttaa      60
taacaagata accacatcaa gatggttgga aagctgaagc agaacttact attggcatgt     120
ctggtgatta gttctgtgac tgtgttttac ctgggccagc atgccatgga atgccatcac     180
cggatagagg aacgtagcca gccagtcaaa ttggagagca aaggaccac tgtgagaact      240 ggcctggacc tcaaagccaa caaaaccttt gcctatcaca agatatgcc tttaatattt      300 attggrggtg tgcctcggag tggaaccaca ctcatgaggg ccatgctgga cgcacatcct     360
gacattcgct gtggagagga aaccagggtc attccccgaa tcctggccct gaagcagatg     420
tggtcacggt caagtaaaga aagatccgc ctggatgagg ctggtgttac tgatgaagtg      480
ctggattctg ccatgcaagc cttcttacta gaaattatcg ttaagcatgg ggagccagcc     540
ccttatttat gtaataaaga tccttttgcc ctgaatctt taacttacct ttctaggtta      600
ttccccaatg ccaaatttct cctgatggtc cgagatggcc gggcatcagt acattcaatg     660
atttctcgaa aagttactat agctggattt gatctgaaca gctataggga ctgtttgaca     720
aagtggaatc gtgctataga gaccatgtat aaccagtgta tggaggttgg ttataaaaag     780
tgcatgttgg ttcactatga acaacttgtc ttacatcctg aacggtggat gagaacactc     840
ttaaagttcc tccagattcc atggaaccac tcagtattgc accatgaaga gatgattggg     900
aaagctgggg gagtgtctct gtcaaaagtg gagagatcta cagaccaagt aatcaagcca     960
```

-continued

```
gtcaatgtag gagctctatc aaaatgggtt gggaagatac cgccagatgt tttacaagac    1020
atggcagtga ttgctcctat gcttgccaag cttggatatg acccatatgc caacccacct    1080
aactacggaa aacctgatcc caaaattatt gaaaacactc gaagggtcta taagggagaa    1140
ttccaactac ctgactttct aaagaaaaa ccacagactg agcaagtgga gtagcagaac    1200
caggagcctc ttccatacat gaggaaagat tgctgccttt tcagcagaag ggaaattcct    1260
aggattggct gtcccctgcc aagcttggtg gagcgtctgc accttggctg cgccgcctgt    1320
gcatttgcca gtttcctccc actgagagga tggaggtgtc cgcacagctt tgggcctcgt    1380
gagggatctg cctcctgagc aaagagctct tgatcccgat tcatgcaca gccctgcagt    1440 aaggagccca aaggaacat gtgtttcctg ttaaaactcc tcttgttctc ttttcttaca    1500
ttatgacgtt tgttttcaag gagagggttt aaaaatggga tcctgtaagc agacttgggc    1560
agtctccttt tgaaataggt tgtctgtaca tgttctaatg ttttgtagaa cacgtgtgcc    1620
tgtttaagtg tattgatgtg aataatatta aatatcctaa ttatttaatt cattgtattg    1680
tttctgagaa gttgggaaat taccattata catttacaac ctaatgactt ttgtatttta    1740
tttttcaaaa taaaagcttt caatgtga                                      1768
```

<210> SEQ ID NO 3
<211> LENGTH: 370
<212> TYPE: PRT
<213> ORGANISM: Mus musculus

<400> SEQUENCE: 3

```
Met Val Gly Lys Leu Lys Gln Asn Leu Leu Leu Ala Cys Leu Val Ile
1               5                   10                  15

Ser Ser Val Thr Val Phe Tyr Leu Gly Gln His Ala Met Glu Cys His
            20                  25                  30

His Arg Ile Glu Glu Arg Ser Gln Pro Ala Arg Leu Glu Asn Pro Lys
        35                  40                  45

Ala Thr Val Arg Ala Gly Leu Asp Ile Lys Ala Asn Lys Thr Phe Thr
    50                  55                  60

Tyr His Lys Asp Met Pro Leu Ile Phe Ile Gly Gly Val Pro Arg Ser
65                  70                  75                  80

Gly Thr Thr Leu Met Arg Ala Met Leu Asp Ala His Pro Asp Ile Arg
                85                  90                  95

Cys Gly Glu Glu Thr Arg Val Ile Pro Arg Ile Leu Ala Leu Lys Gln
            100                 105                 110

Met Trp Ser Arg Ser Ser Lys Glu Lys Ile Arg Leu Asp Glu Ala Gly
        115                 120                 125

Val Thr Asp Glu Val Leu Asp Ser Ala Met Gln Ala Phe Leu Leu Glu
    130                 135                 140

Val Ile Val Lys His Gly Glu Pro Ala Pro Tyr Leu Cys Asn Lys Asp
145                 150                 155                 160

Pro Phe Ala Leu Lys Ser Leu Thr Tyr Leu Ala Arg Leu Phe Pro Asn
                165                 170                 175

Ala Lys Phe Leu Leu Met Val Arg Asp Gly Arg Ala Ser Val His Ser
            180                 185                 190

Met Ile Ser Arg Lys Val Thr Ile Ala Gly Phe Asp Leu Asn Ser Tyr
        195                 200                 205

Arg Asp Cys Leu Thr Lys Trp Asn Arg Ala Ile Glu Thr Met Tyr Asn
    210                 215                 220
```

```
Gln Cys Met Glu Val Gly Tyr Lys Lys Cys Met Leu Val His Tyr Glu
225                 230                 235                 240

Gln Leu Val Leu His Pro Glu Arg Trp Met Arg Thr Leu Leu Lys Phe
            245                 250                 255

Leu His Ile Pro Trp Asn His Ser Val Leu His Glu Glu Met Ile
        260                 265                 270

Gly Lys Ala Gly Gly Val Ser Leu Ser Lys Val Glu Arg Ser Thr Asp
    275                 280                 285

Gln Val Ile Lys Pro Val Asn Val Gly Ala Leu Ser Lys Trp Val Gly
    290                 295                 300

Lys Ile Pro Pro Asp Val Leu Gln Asp Met Ala Val Ile Ala Pro Met
305                 310                 315                 320

Leu Ala Lys Leu Gly Tyr Asp Pro Tyr Ala Asn Pro Pro Asn Tyr Gly
                325                 330                 335

Lys Pro Asp Pro Lys Ile Leu Glu Asn Thr Arg Arg Val Tyr Lys Gly
            340                 345                 350

Glu Phe Gln Leu Pro Asp Phe Leu Lys Glu Lys Pro Gln Thr Glu Gln
            355                 360                 365

Val Glu
    370

<210> SEQ ID NO 4
<211> LENGTH: 1867
<212> TYPE: DNA
<213> ORGANISM: Mus musculus

<400> SEQUENCE: 4
tgcctgcctc cggaataagc tgttgaattc ttgtttcttc cagcgcggtg tctgcctgca      60
cgctgccatg cgtcctgcca tgatgataat ggactgaccc tctgaaactg tgccgatccc     120
cttgccacag tcgagtctcc atggcctgac cgtgtcttga caataatttt gagcaaaatc     180
tatgtctaat aagaagataa ccacatcaag atggttggga agctgaagca gaacttactc     240
ttggcgtgtc tggtgattag ttctgtgacc gtgttttacc tgggccagca tgccatggag     300
tgccatcacc gaatagagga acgtagccag ccagcccgac tggagaaccc caaggcgact     360
gtgcgagctg gcctcgacat caaagccaac aaaacattca cctatcacaa agatatgcct     420
ttaatattca tcgggggtgt gcctcggagc ggcaccacac tcatgagggc tatgctggac     480
gcacatcctg acatccgctg tggagaggaa accagggtca tccctcgaat cctggccctg     540
aagcagatgt ggtcccggtc cagtaaagag aagatccgct ggatgaggc gggtgtcaca     600 gatgaagtgc tagattctgc catgcaagcc ttccttctgg aggtcattgt taaacatggg     660
gagccggcac cttatttatg taacaaagat ccgtttgccc tgaaatcctt gacttacctt     720
gctaggttat ttcccaatgc caaatttctc ctgatggtcc gagatggccg gcgtcagta     780 cattcaatga tttctcggaa agttactata gctggctttg acctgaacag ctaccgggac     840
tgtctgacca gtggaaccg ggccatagaa accatgtaca accagtgtat ggaagttggt     900
tataagaaat gcatgttggt tcactatgaa cagctcgtct acaccctga cggtggatg      960 agaacgctct taaagttcct ccatattcca tggaaccatt ccgttttgca ccatgaagaa    1020
atgatcggga agctgggggg agtttctctg tcaaaggtgg aaagatcaac agaccaagtc    1080
atcaaacccg tcaacgtggg ggcgctatcg aagtgggttg gaagatacc cccggacgtc    1140 ttacaagaca tggccgtgat tgcacccatg ctcgccaagc ttggatatga cccatacgcc    1200
aatcctccta actacggaaa acctgacccc aagatccttg aaaacaccag gagggtctat    1260
```

-continued

```
aaaggagaat tcagctccc tgactttctg aaagaaaaac cccagacgga gcaagtggag      1320
taactgagcc cgtaacttcc cacagggacg actgctgcct tgtctacaga agggaaatct     1380
cgggaacggc tgtctgctgc gacaaggagt gtctgtgccc atcgctcctg ttcacctgcc     1440
agcctcctgt ccccaggggg ggtgtcacac acccgggcct ccccaagtga tggctcttga     1500
gcccaggaac atgcatggcc ctcaggatga ggagcccagc agggacacag ttctgtcaca     1560
gctcctcttg tccttgtctt tccttcccag gttccagtct ttaatttcaa ggaaaggaga     1620
gtttgaagtt ggcattctgt taacaaaatc aggcagtctc attccgaata ggttctatgt     1680
acacgttccg atgttttgta gaacactcgt gcctgttgaa acgtatcgat gtggataata     1740
gtaaatacct taattattta ataattcat tgtattgttt cagagacgtt tggaaattac      1800
tgtatacatt tacaacctaa tgactttgt attttatttt tcaaaataaa agcttaaatg      1860
tgaagca                                                               1867
```

<210> SEQ ID NO 5
<211> LENGTH: 377
<212> TYPE: PRT
<213> ORGANISM: Homo sapiens

<400> SEQUENCE: 5

```
Met Arg Leu Ser Val Arg Val Leu Leu Ala Ala Gly Cys Ala Leu
1               5                   10                  15

Val Leu Val Leu Ala Val Gln Leu Gly Gln Gln Val Leu Glu Cys Arg
                20                  25                  30

Ala Val Leu Ala Gly Leu Arg Ser Pro Arg Gly Ala Met Arg Pro Glu
            35                  40                  45

Gln Glu Glu Leu Val Met Val Gly Thr Asn His Val Glu Tyr Arg Tyr
        50                  55                  60

Gly Lys Ala Met Pro Leu Ile Phe Val Gly Val Pro Arg Ser Gly
65                  70                  75                  80

Thr Thr Leu Met Arg Ala Met Leu Asp Ala His Pro Glu Val Arg Cys
                85                  90                  95

Gly Glu Glu Thr Arg Ile Ile Pro Arg Val Leu Ala Met Arg Gln Ala
            100                 105                 110

Trp Ser Lys Ser Gly Arg Glu Lys Leu Arg Leu Asp Glu Ala Gly Val
        115                 120                 125

Thr Asp Glu Val Leu Asp Ala Ala Met Gln Ala Phe Ile Leu Glu Val
130                 135                 140

Ile Ala Lys His Gly Glu Pro Ala Arg Val Leu Cys Asn Lys Asp Pro
145                 150                 155                 160

Phe Thr Leu Lys Ser Ser Val Tyr Leu Ser Arg Leu Phe Pro Asn Ser
                165                 170                 175

Lys Phe Leu Leu Met Val Arg Asp Gly Arg Ala Ser Val His Ser Met
            180                 185                 190

Ile Thr Arg Lys Val Thr Ile Ala Gly Phe Asp Leu Ser Ser Tyr Arg
        195                 200                 205

Asp Cys Leu Thr Lys Trp Asn Lys Ala Ile Glu Val Met Tyr Ala Gln
210                 215                 220

Cys Met Glu Val Gly Lys Glu Lys Cys Leu Pro Val Tyr Tyr Glu Gln
225                 230                 235                 240

Leu Val Leu His Pro Arg Arg Ser Leu Lys Leu Ile Leu Asp Phe Leu
                245                 250                 255
```

```
Gly Ile Ala Trp Ser Asp Ala Val Leu His His Glu Asp Leu Ile Gly
            260                 265                 270

Lys Pro Gly Val Ser Leu Ser Lys Ile Glu Arg Ser Thr Asp Gln
        275                 280                 285

Val Ile Lys Pro Val Asn Leu Glu Ala Leu Ser Lys Trp Thr Gly His
    290                 295                 300

Ile Pro Gly Asp Val Val Arg Asp Met Ala Gln Ile Ala Pro Met Leu
305                 310                 315                 320

Ala Gln Leu Gly Tyr Asp Pro Tyr Ala Asn Pro Asn Tyr Gly Asn
            325                 330                 335

Pro Asp Pro Phe Val Ile Asn Asn Thr Gln Arg Val Leu Lys Gly Asp
        340                 345                 350

Tyr Lys Thr Pro Ala Asn Leu Lys Gly Tyr Phe Gln Val Asn Gln Asn
        355                 360                 365

Ser Thr Ser Ser His Leu Gly Ser Ser
    370                 375

<210> SEQ ID NO 6
<211> LENGTH: 1855
<212> TYPE: DNA
<213> ORGANISM: Homo sapiens

<400> SEQUENCE: 6
ctgggtgcgt ggggctgcct cgccgcgtct cgccacgggc tctgccagca gacagccttg      60
gcacacaggc acaagggctg gagcccagag atgagagtgc caagggaga tgtgagcctg     120 gcgggctgcc cgctaacctg tcgctgaagc cccagaagcg ggccctcagg ccaggcctac     180
cctgcctccg gccagcatg cgcctgtcgg tgcggaggt gctgctggca gccggctgcg      240
ccctggtcct ggtgctggcg gttcagctgg acagcaggt gctagagtgc cgggcggtgc      300
tggcgggcct gcggagcccc cggggggcca tgcggcctga gcaggaggag ctggtgatgg     360
tgggcaccaa ccacgtggaa taccgctatg caaggccat gccgctcatc ttcgtgggtg     420
gcgtgcctcg cagtggcacc acgttgatgc gcgccatgct ggacgcccac cccgaggtgc     480
gctgcggcga ggagacccgc atcatcccgc gcgtgctggc catgcgccag gcctggtcca     540
agtctggccg tgagaagctg cggctggatg aggcggggt gacggatgag gtgctggacg     600
ccgccatgca ggccttcatc ctggaggtga ttgccaagca cggagagccg gcccgcgtgc     660
tctgcaacaa ggacccattt acgctcaagt cctcggtcta cctgtcgcgc ctgttcccca     720
actccaagtt cctgctgatg gtgcgggacg gccgggcctc cgtgcactcc atgatcacgc     780
gcaaagtcac cattgcgggc tttgacctca gcagctaccg tgactgcctc accaagtgga     840
acaaggccat cgaggtgatg tacgcccagt gcatggaggt aggcaaggag aagtgcttgc     900
ctgtgtacta cgagcagctg gtgctgcacc ccaggcgctc actcaagctc atcctcgact     960
tcctcggcat cgcctggagc gacgctgtcc tccaccatga agacctcatt ggcaagcccg    1020
gtggtgtctc cctgtccaag atcgagcggt ccacggacca ggtcatcaag cctgttaacc    1080
tggaagcgct ctccaagtgg actggccaca tccctgggga tgtggtgcgg acatggccc    1140 agatcgcccc catgctggct cagctcggct atgacccta tgcaaacccc cccaactatg    1200
gcaaccctga ccccttcgtc atcaacaaca cacagcgggt cttgaaaggg gactataaaa    1260
caccagccaa tctgaaagga tattttcagg tgaaccagaa cagcacctcc tcccacttag    1320
gaagctcgtg atttccagat ctccgcaaat gacttcattg ccaagaagag aagaaaatgc    1380
atttaagtgg aaatcggacc tctaatccaa gcatattgct tgctattaat cgccaaaaca    1440
```

-continued

```
ggactgctga tgaggaatgt atttgcatat gtttgcaaaa gctgaatcat tgaaaacgta   1500
ccttgaaact ctctatctct ggacactcca gggtagagaa tgaagggtat ggaagtagtc   1560
cggcttttga aacttaggta ttttatattt ttcccctcaa gaactttttt ttaagagaca   1620
gatttgccat cctccttaat ttgcaggact gccttggtgg ctttgtttgc tgggacaagg   1680
cccacaacct gtgcctctcc tattgaccct tactttgaat tcaaagaatc tatttaagag   1740
tttaatatat gaggctttct ttgattcctc ctcagttcta cctagtttca cagaggaaaa   1800
aaatactctt tgaataaagt gaacagaggc tcatttgttt gtgcctcact ttaca        1855
```

<210> SEQ ID NO 7
<211> LENGTH: 376
<212> TYPE: PRT
<213> ORGANISM: Mus musculus

<400> SEQUENCE: 7

```
Met Arg Leu Ser Val Arg Lys Val Leu Leu Ala Ala Gly Cys Ala Leu
1               5                   10                  15

Ala Leu Val Leu Ala Val Gln Leu Gly Gln Gln Val Leu Glu Cys Arg
            20                  25                  30

Ala Val Leu Gly Gly Thr Arg Asn Pro Arg Arg Met Arg Pro Glu Gln
        35                  40                  45

Glu Glu Leu Val Met Leu Gly Ala Asp His Val Glu Tyr Arg Tyr Gly
    50                  55                  60

Lys Ala Met Pro Leu Ile Phe Val Gly Val Pro Arg Ser Gly Thr
65                  70                  75                  80

Thr Leu Met Arg Ala Met Leu Asp Ala His Pro Glu Val Arg Cys Gly
                85                  90                  95

Glu Glu Thr Arg Ile Ile Pro Arg Val Leu Ala Met Arg Gln Ala Trp
            100                 105                 110

Thr Lys Ser Gly Arg Glu Lys Leu Arg Leu Asp Glu Ala Gly Val Thr
        115                 120                 125

Asp Glu Val Leu Asp Ala Ala Met Gln Ala Phe Ile Leu Glu Val Ile
    130                 135                 140

Ala Lys His Gly Glu Pro Ala Arg Val Leu Cys Asn Lys Asp Pro Phe
145                 150                 155                 160

Thr Leu Lys Ser Ser Val Tyr Leu Ala Arg Leu Phe Pro Asn Ser Lys
                165                 170                 175

Phe Leu Leu Met Val Arg Asp Gly Arg Ala Ser Val His Ser Met Ile
            180                 185                 190

Thr Arg Lys Val Thr Ile Ala Gly Phe Asp Leu Ser Ser Tyr Arg Asp
        195                 200                 205

Cys Leu Thr Lys Trp Asn Lys Ala Ile Glu Val Met Tyr Ala Gln Cys
    210                 215                 220

Met Glu Val Gly Arg Asp Lys Cys Leu Pro Val Tyr Tyr Glu Gln Leu
225                 230                 235                 240

Val Leu His Pro Arg Arg Ser Leu Lys Arg Ile Leu Asp Phe Leu Gly
                245                 250                 255

Ile Ala Trp Ser Asp Thr Val Leu His His Glu Asp Leu Ile Gly Lys
            260                 265                 270

Pro Gly Gly Val Ser Leu Ser Lys Ile Glu Arg Ser Thr Asp Gln Val
        275                 280                 285

Ile Lys Pro Val Asn Leu Glu Ala Leu Ser Lys Trp Thr Gly His Ile
    290                 295                 300
```

Pro Arg Asp Val Val Arg Asp Met Ala Gln Ile Ala Pro Met Leu Ala
305                 310                 315                 320

Arg Leu Gly Tyr Asp Pro Tyr Ala Asn Pro Asn Tyr Gly Asn Pro
            325                 330                 335

Asp Pro Ile Val Ile Asn Asn Thr His Arg Val Leu Lys Gly Asp Tyr
            340                 345                 350

Lys Thr Pro Ala Asn Leu Lys Gly Tyr Phe Gln Val Asn Gln Asn Ser
        355                 360                 365

Thr Ser Pro His Leu Gly Ser Ser
    370                 375

<210> SEQ ID NO 8
<211> LENGTH: 1760
<212> TYPE: DNA
<213> ORGANISM: Mus muscuulus

<400> SEQUENCE: 8

| | | | | | |
|---|---|---|---|---|---|
| atttgggcac | ggactgtcag | ggcaggaagc | cgtggtgacc | aggctcgagg | actggtgctt | 60 |
| gaaaatgagg | gcgcccaggg | gagatgtata | ccaggtgggc | ctgctgaccc | gtccatgagg | 120 |
| cgggccccct | ggctgggcct | gcgaccctgg | ctgggcatgc | gcctgtcggt | gcgtaaggtg | 180 |
| ctgctggccg | ccggctgtgc | tctggccctg | tgctcgctg | tgcagcttgg | gcagcaagta | 240 |
| ctggagtgcc | gggcggtgct | cggggcaca | cggaacccac | ggaggatgcg | gccggagcag | 300 |
| gaggaactgg | tgatgctcgg | cgccgaccac | gtggagtacc | gctatggcaa | ggccatgcca | 360 |
| ctcatctttg | tgggcggcgt | gccacgcagt | ggcaccacgc | tcatgcgcgc | catgttggac | 420 |
| gcacacccag | aggtgcgctg | tggggaggag | acgcgcatca | tccctcgtgt | gctggccatg | 480 |
| cggcaggcct | ggaccaagtc | tggccgtgag | aagctgcggc | tggacgaggc | aggtgtgacg | 540 |
| gatgaggtgc | tggacgcggc | catgcaggcc | ttcattctgg | aggtgatcgc | caagcacggc | 600 |
| gaaccagccc | gcgtgctgtg | taacaaggac | cccttcacac | tcaagtcatc | cgtctacctg | 660 |
| gcacgcctgt | tccccaactc | caaattcctg | ctaatggtgc | gtgacggccg | ggcgtccgtg | 720 |
| cactccatga | tcacgcgcaa | ggtcaccatc | gcgggctttg | acctcagcag | ctaccgagac | 780 |
| tgcctcacca | gtggaacaa | ggccatcgag | gtgatgtacg | cacagtgcat | ggaggtgggc | 840 |
| agggacaagt | gcctgcccgt | gtactatgag | cagttggtgc | tgcaccccg | gcgctcactc | 900 |
| aaacgcatcc | tggacttcct | gggcatcgcc | tggagtgaca | cagtcctgca | ccacgaggac | 960 |
| ctcattggca | agcctggggg | cgtctccttg | tccaagatcg | agcggtccac | ggaccaggtc | 1020 |
| atcaaaccgg | tgaacttgga | agctctctcc | aagtggacgg | ccacatccc | tagagacgtg | 1080 |
| gtgagggata | tggcccagat | tgcccccatg | ctggcccggc | ttggctatga | cccgtatgcg | 1140 |
| aatccaccca | actatgggaa | ccccgacccc | attgtcatca | acaacacaca | ccgggtcttg | 1200 |
| aaaggagact | ataaaacgcc | agccaatctg | aaaggatatt | tccaggtgaa | ccagaacagc | 1260 |
| acctccccac | acctaggaag | ttcgtgattt | ccagtccctg | cagggctcag | acgcctcagt | 1320 |
| cctcgacctg | cacacggaag | ctggactaac | ccaagcacat | ggcttgctct | cagtcacgcc | 1380 |
| gggcggggcc | tgccgggttg | gagcattcat | acatctcggc | aaagcgggc | ttggaacctc | 1440 |
| cgctccagga | caacactaag | gagggagaga | ctacttccgc | ttcagaaact | ggagatttt | 1500 |
| ctaatttttc | tctccttggg | aactttttt | ttaaagaatt | gaatttgcta | tcttccctaa | 1560 |
| cggacagacc | ccttggtgac | ctcatctcct | gggacaagac | cggagacccg | tgcctctcct | 1620 |
| tgactggacg | ttgaactcaa | aggatctatt | taagagttta | atatatgggc | tctccttgct | 1680 |

```
ctagtcctac tcagtttcac agagaaaaga aattaattat ttgaataaag tagacaggct    1740
gctgtctgtg ccttacttca                                                1760
```

<210> SEQ ID NO 9
<211> LENGTH: 380
<212> TYPE: PRT
<213> ORGANISM: Caenorhabditis elegans

<400> SEQUENCE: 9

```
Met Arg Lys Asn Arg Glu Leu Leu Val Leu Phe Leu Val Val Phe
1               5                   10                  15

Ile Leu Phe Tyr Phe Ile Thr Ala Arg Thr Ala Asp Asp Pro Tyr Tyr
            20                  25                  30

Ser Asn His Arg Glu Lys Phe Asn Gly Ala Ala Ala Asp Gly Asp
        35                  40                  45

Glu Ser Leu Pro Phe His Gln Leu Thr Ser Val Arg Ser Asp Asp Gly
50                  55                  60

Tyr Asn Arg Thr Ser Pro Phe Ile Phe Ile Gly Gly Val Pro Arg Ser
65                  70                  75                  80

Gly Thr Thr Leu Met Arg Ala Met Leu Asp Ala His Pro Glu Val Arg
                85                  90                  95

Cys Gly Glu Glu Thr Arg Val Ile Pro Arg Ile Leu Asn Leu Arg Ser
            100                 105                 110

Gln Trp Lys Lys Ser Glu Lys Glu Trp Asn Arg Leu Gln Gln Ala Gly
        115                 120                 125

Val Thr Gly Glu Val Ile Asn Asn Ala Ile Ser Ser Phe Ile Met Glu
    130                 135                 140

Ile Met Val Gly His Gly Asp Arg Ala Pro Arg Leu Cys Asn Lys Asp
145                 150                 155                 160

Pro Phe Thr Met Lys Ser Ala Val Tyr Leu Lys Glu Leu Phe Pro Asn
                165                 170                 175

Ala Lys Tyr Leu Leu Met Ile Arg Asp Gly Arg Ala Thr Val Asn Ser
            180                 185                 190

Ile Ile Ser Arg Lys Val Thr Ile Thr Gly Phe Asp Leu Asn Asp Phe
        195                 200                 205

Arg Gln Cys Met Thr Lys Trp Asn Ala Ala Ile Gln Ile Met Val Asp
    210                 215                 220

Gln Cys Glu Ser Val Gly Glu Lys Asn Cys Leu Lys Val Tyr Tyr Glu
225                 230                 235                 240

Gln Leu Val Leu His Pro Glu Ala Gln Met Arg Arg Ile Thr Glu Phe
                245                 250                 255

Leu Asp Ile Pro Trp Asp Lys Val Leu His His Glu Gln Leu Ile
            260                 265                 270

Gly Lys Asp Ile Ser Leu Ser Asn Val Glu Arg Ser Ser Asp Gln Val
        275                 280                 285

Val Lys Pro Val Asn Leu Asp Ala Leu Ile Lys Trp Val Gly Thr Ile
    290                 295                 300

Pro Glu Asp Val Val Ala Asp Met Asp Ser Val Ala Pro Met Leu Arg
305                 310                 315                 320

Arg Leu Gly Tyr Asp Pro Asn Ala Asn Pro Pro Asn Tyr Gly Lys Pro
                325                 330                 335

Asp Glu Leu Val Ala Lys Lys Thr Glu Asp Val His Lys Asn Gly Ala
            340                 345                 350
```

```
Glu Trp Tyr Lys Lys Ala Val Gln Val Val Asn Asp Pro Gly Arg Val
            355                 360                 365

Asp Lys Pro Ile Val Asp Asn Glu Val Ser Lys Leu
    370                 375                 380

<210> SEQ ID NO 10
<211> LENGTH: 1426
<212> TYPE: DNA
<213> ORGANISM: Cainorhabditis elegans

<400> SEQUENCE: 10
caccgatgca ctcatagtga agcagcagca gcagccaaaa ttgaatgaga aaggcgaata      60
ttataatgag aaaaaatcga gagttgctac tcgtcctctt cctcgtcgtt tttatactat    120
tctattttat tactgcgaga actgcagacg acccgtacta cagtaaccat cgggagaaat    180
tcaatggtgc cgccgccgac gacggcgacg agtcgttacc ttttcatcaa ttaacgtcag    240
tacgaagtga tgatggatac aatagaacgt ctcctttcat attcataggt ggtgttcctc    300
gctccggtac aactctgatg cgtgcgatgc ttgacgctca tccagaagtc agatgtggtg    360
aggagacacg tgtcattcca cgcatcctga atctacggtc acaatggaaa aagtcggaaa    420
aggagtggaa tcgactgcag caggctggag tgacgggtga agtgattaac aatgcgatca    480
gctcgtttat catggagata atggttggcc acggagatcg ggctcctcgt ctctgcaaca    540
aggatccatt cacaatgaaa tcagccgtct acctaaaaga actcttccca aatgccaaat    600
atcttctaat gatccgtgat ggacgggcca ccgtgaatag tataatctca cgaaaagtca    660
caattaccgg attcgatttg aacgatttcc gtcaatgcat gacgaaatgg aatgcggcaa    720
ttcaaataat ggtagatcag tgtgaatcgg ttggagagaa aaattgtttg aaagtgtatt    780
atgagcagct ggtgctacat ccggaagcac aaatgcggcg aattacagag ttttttggata    840 ttccgtggga tgataaagtg ctgcaccatg agcagcttat tggaaaagat atttctttat    900
cgaatgtgga acggagctcg gatcaagtcg ttaaaccggt taatcttgat gctcttatca    960
aatgggttgg aacgattcct gaggatgttg ttgctgatat ggattcggtt gcgccgatgt   1020
taaggagatt aggatatgat ccgaatgcaa atccaccaaa ctatgaaaaa cccgacgaac   1080
tagtcgcgaa aaaacggaa gatgttcata aaaatggagc cgaatggtac aagaaagcag   1140
ttcaagtggt caacgatccc ggccgcgtcg ataaaccaat tgttgataat gaagtatcga   1200
aattatagag aaatcgaaga agaatatttt tataaattga acttttttaa cgggtccccc   1260
ccatctcttc tagttgcctt tcccacccc acttttttccc ctaattcgtg atatttccat   1320
tctctccgtt gtgtgtttgt gtaccattaa tttattttca aatgttccat cttttgcatt   1380
cgggttttat tattttatta ttatcataaa gttttcgaga ttttta               1426

<210> SEQ ID NO 11
<211> LENGTH: 359
<212> TYPE: PRT
<213> ORGANISM: Cainorhabditis elegans

<400> SEQUENCE: 11

Met Tyr Thr Ala Leu Asn Asn Met Leu Ser Asn Ile Cys Ala Thr Ile
1               5                   10                  15

Glu Leu Ile Phe Glu Tyr Ile Asn Cys Ser Gln Pro Phe Phe Ile Tyr
            20                  25                  30

Ile Phe Ile Phe Cys Phe Thr Ile Cys Leu Leu Ile Phe Ser Ser Ile
        35                  40                  45
```

```
Lys Cys Lys Lys Leu Gln Glu Lys Leu Glu Gln Leu Ser Leu Ser Lys
 50                  55                  60

Glu Ser Leu Ile Phe Asn Glu Gln Asp Ala Arg His Ser Arg Arg Leu
 65                  70                  75                  80

Leu Ser Asn Leu Glu Gln Leu Ile Phe Val Gly Gly Val Pro Arg Ser
                 85                  90                  95

Gly Thr Thr Leu Met Arg Ala Ile Leu Asp Ala His Pro Asp Val Arg
            100                 105                 110

Cys Gly Gly Glu Thr Met Leu Leu Pro Ser Phe Leu Thr Trp Gln Ala
        115                 120                 125

Gly Trp Arg Asn Asp Trp Val Asn Asn Ser Gly Ile Thr Gln Glu Val
    130                 135                 140

Phe Asp Asp Ala Val Ser Ala Phe Ile Thr Glu Ile Val Ala Lys His
145                 150                 155                 160

Ser Glu Leu Ala Pro Arg Leu Cys Asn Lys Asp Pro Tyr Thr Ala Leu
                165                 170                 175

Trp Leu Pro Thr Ile Arg Arg Leu Tyr Pro Asn Ala Lys Phe Ile Leu
            180                 185                 190

Met Ile Arg Asp Ala Arg Ala Val Val His Ser Met Ile Glu Arg Lys
        195                 200                 205

Val Pro Val Ala Gly Tyr Asn Thr Ser Asp Glu Ile Ser Met Phe Val
    210                 215                 220

Gln Trp Asn Gln Glu Leu Arg Lys Met Thr Phe Gln Cys Asn Asn Ala
225                 230                 235                 240

Pro Gly Gln Cys Ile Lys Val Tyr Tyr Glu Arg Leu Ile Gln Lys Pro
                245                 250                 255

Ala Glu Glu Ile Leu Arg Ile Thr Asn Phe Leu Asp Leu Pro Phe Ser
            260                 265                 270

Gln Gln Met Leu Arg His Gln Asp Leu Ile Gly Asp Glu Val Asp Leu
        275                 280                 285

Asn Asp Gln Glu Phe Ser Ala Ser Gln Val Lys Asn Ser Ile Asn Thr
    290                 295                 300

Lys Ala Leu Thr Ser Trp Phe Asp Cys Phe Ser Glu Glu Thr Leu Arg
305                 310                 315                 320

Lys Leu Asp Asp Val Ala Pro Phe Leu Gly Ile Leu Gly Tyr Asp Thr
                325                 330                 335

Ser Ile Ser Lys Pro Asp Tyr Ser Thr Phe Ala Asp Asp Phe Tyr
            340                 345                 350

Gln Phe Lys Asn Phe Tyr Ser
        355
```

<210> SEQ ID NO 12
<211> LENGTH: 1080
<212> TYPE: DNA
<213> ORGANISM: Caenorhabditis elegans

<400> SEQUENCE: 12

| | | | | | |
|---|---|---|---|---|---|
| atgtataccg | cgcttaataa | tatgctttca | aatatttgtg | caactattga | attaattttt | 60 |
| gaatatatta | actgttccca | gcccttttt | atctatattt | tcattttttg | ctttacaatc | 120 |
| tgtcttttga | tattctcttc | aataaagtgt | aagaaacttc | aggaaaagtt | agaacagcta | 180 |
| agtctttcaa | aagagagctt | aatcttcaat | gagcaagatg | ctcgacactc | gagacgactc | 240 |
| ctctcaaatt | tggagcagct | gattttgtg | ggtggtgtgc | cgagaagtgg | gactactttg | 300 |
| atgagagcta | ttctagatgc | acatccggat | gttcgatgtg | gcggtgaaac | catgctgctt | 360 |

```
ccaagtttcc ttacatggca agcaggctgg cggaatgatt gggtcaataa ttcaggaatt    420
actcaggaag tatttgacga cgctgtttca gcattcatca ctgagatagt cgcgaagcac    480
agtgaactag cacctcgtct gtgcaacaag gatccataca ccgcattgtg gcttccgact    540
attcgccgac tgtacccgaa tgcaaagttt attctgatga ttcgagatgc tcgtgccgta    600
gttcattcaa tgatagaaag aaaagtacca gttgctggt ataatacgtc tgatgaaatt    660
tcaatgtttg ttcagtggaa tcaggagctt cgaaaatga cttttcaatg caataatgcg    720
ccagggcaat gcataaaagt atattatgaa cgactgattc aaaaacctgc ggaagaaatc    780
ctacgtatca ccaacttcct ggatctgcca ttttcccagc aaatgctaag acatcaagat    840
ttaattggag acgaagttga tttaaacgat caagaattct ctgcatcaca agttaaaaac    900
tcgataaaca ctaaagcctt aacctcgtgg tttgattgtt ttagtgaaga aactctacga    960
aaacttgatg acgtggcacc ttttttggga attcttggat acgatacgtc gatttcaaaa    1020
cccgattatt ccacatttgc ggatgacgat ttttaccaat ttaaaaattt ttattcttaa    1080
```

<210> SEQ ID NO 13
<211> LENGTH: 295
<212> TYPE: PRT
<213> ORGANISM: Mus musculus

<400> SEQUENCE: 13

```
Met Glu Thr Ser Met Pro Glu Tyr Tyr Glu Val Phe Gly Glu Phe Arg
1               5                   10                  15

Gly Val Leu Met Asp Lys Arg Phe Thr Lys Tyr Trp Glu Asp Val Glu
            20                  25                  30

Met Phe Leu Ala Arg Pro Asp Asp Leu Val Ile Ala Thr Tyr Pro Lys
        35                  40                  45

Ser Gly Thr Thr Trp Ile Ser Glu Val Val Tyr Met Ile Tyr Lys Glu
    50                  55                  60

Gly Asp Val Glu Lys Cys Lys Glu Asp Ala Ile Phe Asn Arg Ile Pro
65                  70                  75                  80

Tyr Leu Glu Cys Arg Asn Glu Asp Leu Ile Asn Gly Ile Lys Gln Leu
                85                  90                  95

Lys Glu Lys Glu Ser Pro Arg Ile Val Lys Thr His Leu Pro Pro Lys
            100                 105                 110

Val Leu Pro Ala Ser Phe Trp Glu Lys Asn Cys Lys Met Ile Tyr Leu
        115                 120                 125

Cys Arg Asn Ala Lys Asp Val Ala Val Ser Tyr Tyr Tyr Phe Leu Leu
    130                 135                 140

Met Ile Thr Ser Tyr Pro Asn Pro Lys Ser Phe Ser Glu Phe Val Glu
145                 150                 155                 160

Lys Phe Met Gln Gly Gln Val Pro Tyr Gly Ser Trp Tyr Asp His Val
                165                 170                 175

Lys Ala Trp Trp Glu Lys Ser Lys Asn Ser Arg Val Leu Phe Met Phe
            180                 185                 190

Tyr Glu Asp Met Lys Glu Asp Ile Arg Arg Glu Val Lys Leu Ile
        195                 200                 205

Glu Phe Leu Glu Arg Lys Pro Ser Ala Glu Leu Val Asp Arg Ile Ile
    210                 215                 220

Gln His Thr Ser Phe Gln Glu Met Lys Asn Asn Pro Ser Thr Asn Tyr
225                 230                 235                 240

Thr Met Met Pro Glu Glu Met Met Asn Gln Lys Val Ser Pro Phe Met
```

```
                245                 250                 255
Arg Lys Gly Ile Ile Gly Asp Trp Lys Asn His Phe Pro Glu Ala Leu
            260                 265                 270

Arg Glu Arg Phe Asp Glu His Tyr Lys Gln Gln Met Lys Asp Cys Thr
        275                 280                 285

Val Lys Phe Arg Met Glu Leu
    290                 295

<210> SEQ ID NO 14
<211> LENGTH: 7
<212> TYPE: PRT
<213> ORGANISM: Homo sapiens

<400> SEQUENCE: 14

Pro Asn Tyr Ala Thr Leu Thr
1               5

<210> SEQ ID NO 15
<211> LENGTH: 22
<212> TYPE: DNA
<213> ORGANISM: Homo sapiens

<400> SEQUENCE: 15
cccaactatg gcaaccctga cc                                          22

<210> SEQ ID NO 16
<211> LENGTH: 21
<212> TYPE: DNA
<213> ORGANISM: Mus musculus

<400> SEQUENCE: 16
cccaactatg ggaaccccga c                                           21

<210> SEQ ID NO 17
<211> LENGTH: 18
<212> TYPE: DNA
<213> ORGANISM: Homo sapiens

<400> SEQUENCE: 17
cccaactatg gcaaccct                                               18

<210> SEQ ID NO 18
<211> LENGTH: 21
<212> TYPE: DNA
<213> ORGANISM: Homo sapiens

<400> SEQUENCE: 18
cccaactatg gcaaccctga c                                           21

<210> SEQ ID NO 19
<211> LENGTH: 21
<212> TYPE: DNA
<213> ORGANISM: Homo sapiens

<400> SEQUENCE: 19
cccaactatg gcaaccctga c                                           21

<210> SEQ ID NO 20
<211> LENGTH: 21
<212> TYPE: DNA
<213> ORGANISM: Homo sapiens

<400> SEQUENCE: 20
```

-continued cccaactatg gcaaccctga c     21

<210> SEQ ID NO 21
<211> LENGTH: 7
<212> TYPE: PRT
<213> ORGANISM: Homo sapiens or Mus musculus

<400> SEQUENCE: 21

Pro Asn Tyr Gly Asn Pro Asp
1               5

<210> SEQ ID NO 22
<211> LENGTH: 16
<212> TYPE: PRT
<213> ORGANISM: Homo sapiens

<400> SEQUENCE: 22

Gln Ala Thr Glu Tyr Glu Tyr Leu Asp Tyr Asp Phe Leu Pro Glu Cys
1               5                   10                  15

<210> SEQ ID NO 23
<211> LENGTH: 17
<212> TYPE: PRT
<213> ORGANISM: Homo sapiens

<400> SEQUENCE: 23

Glu Ala Asn Glu Asp Tyr Glu Asp Tyr Glu Tyr Asp Glu Leu Pro Ala
1               5                   10                  15

Cys

<210> SEQ ID NO 24
<211> LENGTH: 16
<212> TYPE: PRT
<213> ORGANISM: Homo sapiens

<400> SEQUENCE: 24

Glu Gly Glu Glu Asp Asp Asp Tyr Leu Asp Leu Glu Lys Ile Phe Cys
1               5                   10                  15

<210> SEQ ID NO 25
<211> LENGTH: 27
<212> TYPE: DNA
<213> ORGANISM: Homo sapiens

<400> SEQUENCE: 25
ctgggtgcgc tcgccacggt aggtggc     27

<210> SEQ ID NO 26
<211> LENGTH: 36
<212> TYPE: DNA
<213> ORGANISM: Homo sapiens

<400> SEQUENCE: 26
cctctccagg gctctgcccc aagggaggta agtgca     36

<210> SEQ ID NO 27
<211> LENGTH: 36
<212> TYPE: DNA
<213> ORGANISM: Homo sapiens

<400> SEQUENCE: 27
tctccccaga tgtgagcccc tgtccaagtg agtgga     36

```
<210> SEQ ID NO 28
<211> LENGTH: 36
<212> TYPE: DNA
<213> ORGANISM: Homo sapiens

<400> SEQUENCE: 28
tctccccagg atcgagcgac acagcgggtg agtgtg                              36

<210> SEQ ID NO 29
<211> LENGTH: 36
<212> TYPE: DNA
<213> ORGANISM: Homo sapiens

<400> SEQUENCE: 29
cttccttagg tcttgaaata ttttcaggtt agaaac                              36

<210> SEQ ID NO 30
<211> LENGTH: 36
<212> TYPE: DNA
<213> ORGANISM: Homo sapiens

<400> SEQUENCE: 30
tttctccagg tgaaccagga tttccaggta agcctg                              36

<210> SEQ ID NO 31
<211> LENGTH: 27
<212> TYPE: DNA
<213> ORGANISM: Homo sapiens

<400> SEQUENCE: 31
cactttcaga tctccgcatt actttac                                        27

<210> SEQ ID NO 32
<211> LENGTH: 30
<212> TYPE: DNA
<213> ORGANISM: Artificial Sequence
<220> FEATURE:
<223> OTHER INFORMATION: primer

<400> SEQUENCE: 32
cgggatccgg ttgggaagct gaagcagaac                                     30

<210> SEQ ID NO 33
<211> LENGTH: 30
<212> TYPE: DNA
<213> ORGANISM: Artificial Sequence
<220> FEATURE:
<223> OTHER INFORMATION: primer

<400> SEQUENCE: 33
ggactagtat tactccactt gctccgtctg                                     30

<210> SEQ ID NO 34
<211> LENGTH: 15
<212> TYPE: PRT
<213> ORGANISM: Artificial Sequence
<220> FEATURE:
<223> OTHER INFORMATION: HPC4 epitope

<400> SEQUENCE: 34

Met Glu Asp Gln Val Asp Pro Arg Leu Ile Asp Gly Lys Asp Pro
1               5                   10                  15

<210> SEQ ID NO 35
```

```
<210> SEQ ID NO 35
<211> LENGTH: 25
<212> TYPE: DNA
<213> ORGANISM: Artificial Sequence
<220> FEATURE:
<223> OTHER INFORMATION: primer

<400> SEQUENCE: 35
cgggatccgc gcctgtcggt gcgta                                            25

<210> SEQ ID NO 36
<211> LENGTH: 25
<212> TYPE: DNA
<213> ORGANISM: Artificial Sequence
<220> FEATURE:
<223> OTHER INFORMATION: primer

<400> SEQUENCE: 36
ggaattctgg aaatcacgag cttcc                                            25

<210> SEQ ID NO 37
<211> LENGTH: 27
<212> TYPE: DNA
<213> ORGANISM: Artificial Sequence
<220> FEATURE:
<223> OTHER INFORMATION: primer

<400> SEQUENCE: 37
cgggatccag gacagcaggt gctagag                                          27

<210> SEQ ID NO 38
<211> LENGTH: 27
<212> TYPE: DNA
<213> ORGANISM: Artificial Sequence
<220> FEATURE:
<223> OTHER INFORMATION: primer

<400> SEQUENCE: 38
cgggatccag ggcagcaagt actggag                                          27

<210> SEQ ID NO 39
<211> LENGTH: 19
<212> TYPE: PRT
<213> ORGANISM: Artificial Sequence
<220> FEATURE:
<223> OTHER INFORMATION: transferrin

<400> SEQUENCE: 39

Met Arg Leu Ala Val Gly Ala Leu Leu Val Cys Ala Val Leu Gly Leu
 1               5                  10                  15

Cys Leu Ala

<210> SEQ ID NO 40
<211> LENGTH: 16
<212> TYPE: PRT
<213> ORGANISM: Artificial Sequence
<220> FEATURE:
<223> OTHER INFORMATION: N-terminus of recombinant soluble enzymes

<400> SEQUENCE: 40

Glu Asp Gln Val Asp Pro Arg Leu Ile Asp Gly Lys Asp Pro Gly Gln
 1               5                  10                  15

<210> SEQ ID NO 41
<211> LENGTH: 18
<212> TYPE: PRT
<213> ORGANISM: Artificial Sequence
```

```
<220> FEATURE:
<223> OTHER INFORMATION: peptide corresponding to residues 360-376 of
      mouse TPST-2

<400> SEQUENCE: 41

Cys Gly Tyr Phe Gln Val Asn Gln Val Ser Thr Ser Pro His Leu Gly
1               5                   10                  15

Ser Ser

<210> SEQ ID NO 42
<211> LENGTH: 27
<212> TYPE: DNA
<213> ORGANISM: Artificial Sequence
<220> FEATURE:
<223> OTHER INFORMATION: primer

<400> SEQUENCE: 42
ccatcctaat acgactcact atagggc                                              27

<210> SEQ ID NO 43
<211> LENGTH: 24
<212> TYPE: DNA
<213> ORGANISM: Artificial Sequence
<220> FEATURE:
<223> OTHER INFORMATION: primer

<400> SEQUENCE: 43
gcgcacagac actccttgtc gcag                                                 24

<210> SEQ ID NO 44
<211> LENGTH: 7
<212> TYPE: PRT
<213> ORGANISM: Artificial sequence
<220> FEATURE:
<223> OTHER INFORMATION: residues which contact the 5' phosphate of PAPS

<400> SEQUENCE: 44

Pro Lys Ser Gly Thr Thr Trp
1               5

<210> SEQ ID NO 45
<211> LENGTH: 7
<212> TYPE: PRT
<213> ORGANISM: Artificial sequence
<220> FEATURE:
<223> OTHER INFORMATION: peptide which corresponds to various residues
      of TPST-1, TPST-2, TPST-A & TPST-B

<400> SEQUENCE: 45

Pro Arg Ser Gly Thr Thr Leu
1               5
```

TYROSYLPROTEIN SULFOTRANSFERASES AND METHODS OF USE THEREOF

CROSS-REFERENCE TO RELATED APPLICATIONS

The present application is a continuation of U.S. Ser. No. 10/201,525, filed Jul. 22, 2002 now U.S. Pat. No. 7,029,890, which is a continuation-in-part of U.S. Ser. No. 09/785,343, filed Feb. 16, 2001, now U.S. Pat. No. 6,605,455, which is a continuation-in-part of U.S. Ser. No. 09/374,493, filed Aug. 13, 1999, now U.S. Pat. No. 6,204,016, which is a continuation-in-part of U.S. Ser. No. 09/150,133, filed Sep. 9, 1998, now U.S. Pat. No. 6,060,295, which claims the benefit of U.S. Provisional Application Ser. No. 60/072,994, filed Jan. 29, 1998. Said U.S. Ser. No. 09/785,343 is also a continuation-in-part of International Application No. PCT/US99/16750 filed Jul. 23, 1999, now published as WO 00/14250. The disclosures of each of the above-referenced applications are incorporated by reference herein.

STATEMENT REGARDING FEDERALLY SPONSORED RESEARCH OR DEVELOPMENT

Some Aspects of this invention were made in the course of Grant HL53602 awarded by the NIH/National Heart, Lung and Blood Institute and therefor the Government has certain rights in some aspects of this invention.

BACKGROUND

The present invention is related to tyrosylprotein sulfotransferases and polynucleotides which encode said tyrosylprotein sulfotransferases and methods of use thereof.

Tyrosine O-sulfation is a post-translation modification of membrane and secretory proteins that occurs in all multicellular eukaryotes (1-3). The enzyme required for this reaction, called tyrosylprotein sulfotransferase (TPST), catalyzes the transfer of sulfate from 3'-phosphoadenosine 5'-phosphosulfate (PAPS) to tyrosines within highly acidic motifs of polypeptides (2,4). Evidence has previously indicated that the enzyme is a membrane-associated protein with a lumenally oriented active site localized in the trans-Golgi network (5,6).

Many proteins have been shown to contain tyrosine sulfate. Among these are several proteins involved in inflammation and hemostasis, including PSGL-1 (7), the α-chain of complement factor C4 (8), coagulation Factors V (9) and VIII (10,11), platelet glycoprotein Ibα (12,13), $α_2$-antiplasmin (14), and heparin cofactor II (15). Although the role of tyrosine O-sulfation is incompletely understood, it is clear that tyrosine O-sulfation plays a role in protein-protein interactions in several systems. Tyrosine O-sulfation is required for the optimal interaction between Factor VIII and Von Willebrand factor (10,11), PSGL-1 and P-selectin (7), GPIbα with Von Willebrand factor and α-thrombin (12,13), and complement factor C4 and C1s (8).

The kinetics of the TPST reaction has been studied using crude and partially-purified enzyme preparations from a variety of mammalian tissues (18,19). However, it has not been clear whether TPST activity is due to one enzyme or a family of enzymes. Two groups have previously reported attempts to purify TPST (20,21). However, neither group was able to sufficiently purify the protein to identify its amino acid sequence, nor have cDNAs encoding the enzyme previously been identified. As a result, there has remained a need in the field for complete identification of TPST and of cDNAs encoding TPST.

BRIEF DESCRIPTION OF THE DRAWINGS

FIG. 3 shows the amino acid sequence and hydropathy plot of human TPST-1 (SEQ ID NO:1). Peptides sequenced from the rat protein are underlined. The Hydropathy plot of human TPST-1 was calculated by the method of Kyte and Doolittle using the PEPPLOT program (Genetics Computer Group, Inc.).

FIG. 6 shows the alignment of the amino acid sequences of mouse estrogen sulfotransferase (SEQ ID NO:13) and mouse TPST-1 (SEQ ID NO:3). The alignment was produced using the BESTFIT program (Genetics Computer Group, Inc.). Amino acid identities between mouse estrogen sulfotransferase and mouse TPST-1 are indicated by a bar, whereas similarities are indicated by double and single dots. Residues involved in co-substrate binding in the estrogen sulfotransferase crystal structure are highlighted. Differences between mouse and human TPST-1 are indicated by asterisk.

FIG. 7 shows alignment of human and mouse TPST-2 cDNA and BAC clone nucleotide sequences. The 21 nucleotides spanning a frame shift mutation in human TPST-2 cDNA clone 810937 (SEQ ID NO:15) were aligned with the corresponding segments of the indicated mouse or human cDNA clones and the human BAC clone 445C9 (SEQ ID NO:20). The position of the frame shift is highlighted by the box. The clones indicated by the asterisk were sequenced in our laboratory. The other sequences were obtained from the NCBI Database and have the following GeneBank accession numbers; clone 256487 (SEQ ID NO:18), H94110; clone EST86111 (SEQ ID NO:19), AA374022; BAC clone 445C9 (SEQ ID NO:20), z95115. The mouse clone 569461 sequence is SEQ ID NO:16; the human clone 307478 sequence is SEQ ID NO:17; the amino-acid sequence on the first line of FIG. 7 is SEQ ID NO:14; and the amino-acid sequence on the last line of FIG. 7 is SEQ ID NO:21.

FIG. 8 shows the amino acid sequence and hydropathy plot of human TPST-2 (SEQ ID NO:5). Two potential sites for N-linked glycosylation are indicated by asterisks and the putative transmembrane domain is boxed. The hydropathy plot was calculated by the method of Kyte and Doolittle using the PEPPLOT program (Genetics Computer Group).

Figure 9:
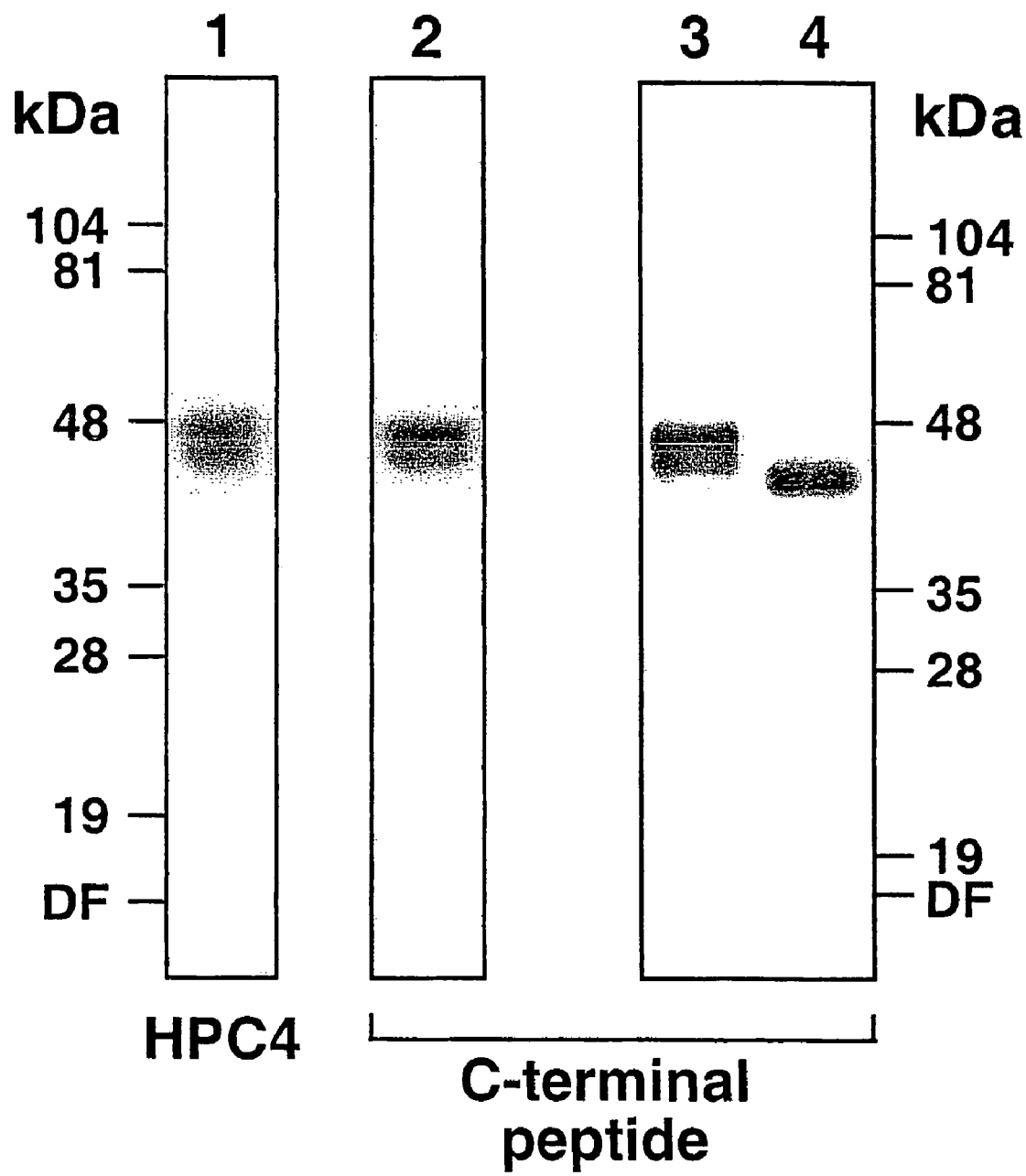

FIG. 9 shows a gel characterizing recombinant TPST-2. Soluble human TPST-2 fusion protein was transiently expressed in 293-T cells and partially purified using HPC4 affinity chromatography. Samples were electrophoresed on 10% SDS polyacrylamide gels under reducing conditions and proteins visualized by Western blotting using HPC4 (lane 1) or antiserum to the C-terminal peptide of TPST-2 (lanes 2-4). The sample in lane 3 was sham-treated and that in lane 4 was treated with peptide N-glycosidase F. DF=dye front.

Figure 10:
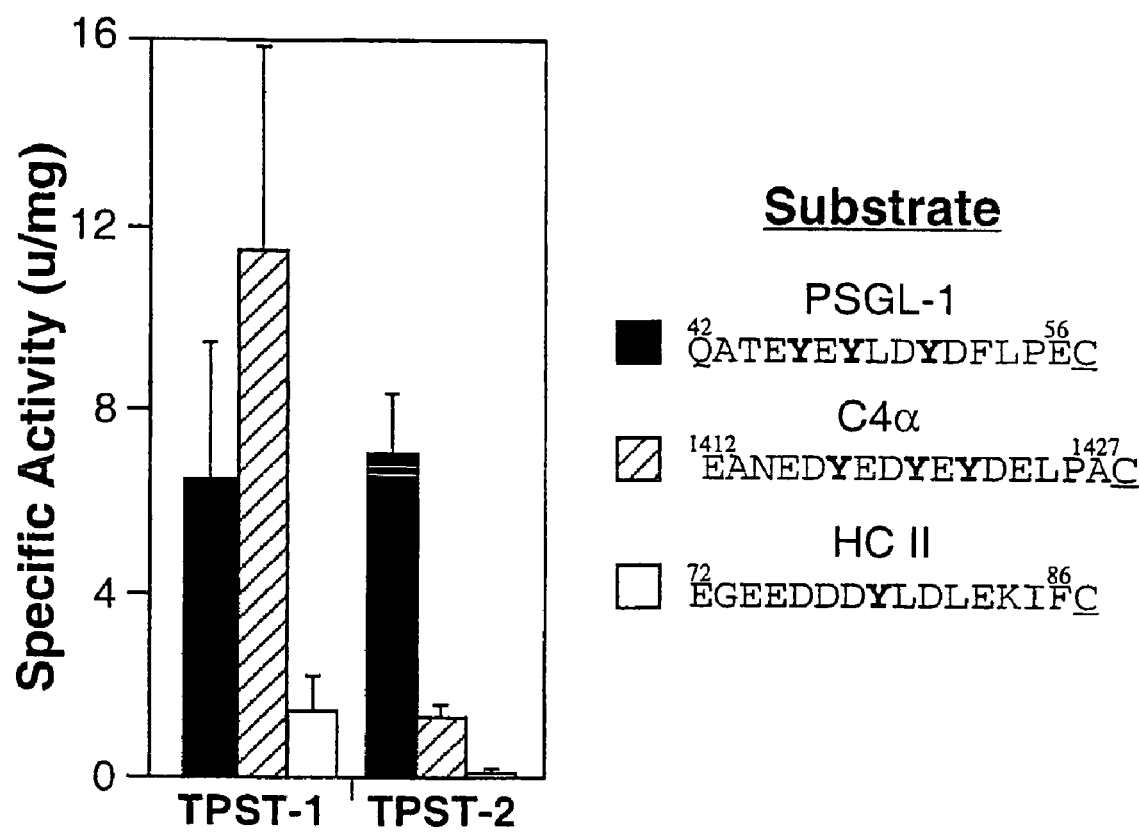

FIG. 10 shows a graph characterizing substrate specificity of TPST-1 and TPST-2. Extracts of mock-transfected 293-T cells or 293-T cells transiently transfected with cDNAs encoding human TPST-1 or TPST-2 HPC4 fusion proteins were prepared, extracted and assayed for TPST activity and protein content. The values shown are the specific activities (mean±SD) of cell extracts from three independent transfections assayed in duplicate using the indicated peptide substrate. The sequences of the peptide substrates are shown on the left. The cysteine residues used to immobilize the peptides are underlined. In FIG. 10, the PSGL-1 sequence is SEQ ID NO:22; the C4α sequence is SEQ ID NO:23; and the HCII sequence is SEQ ID NO:24.

Figure 11:
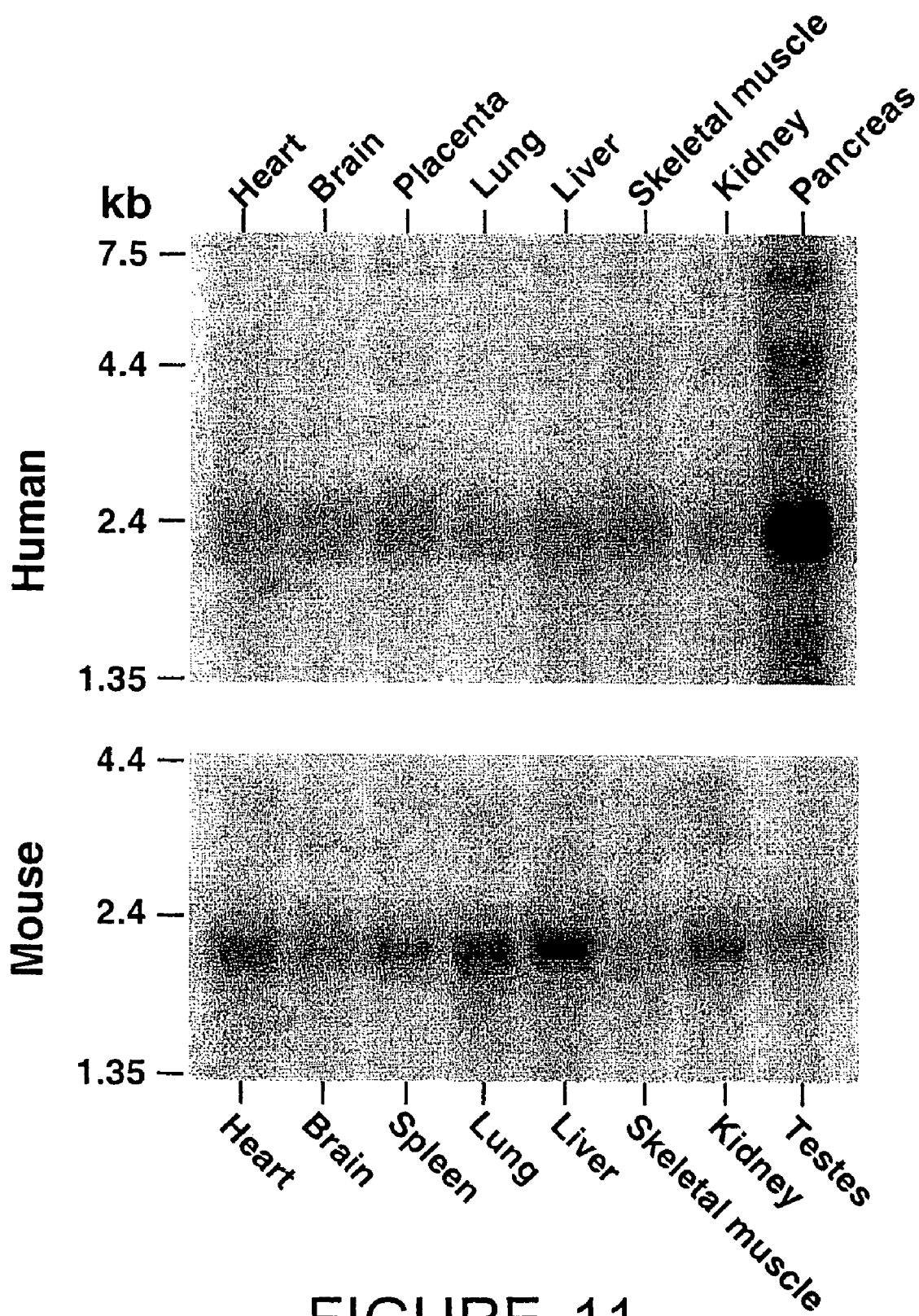

FIG. 11 is a Northern Blot analysis of poly(A)+ mRNA from multiple human and mouse tissues and human cell lines probed with $^{32}$P-labeled partial cDNA probes from TPST-2.

Figure 12:
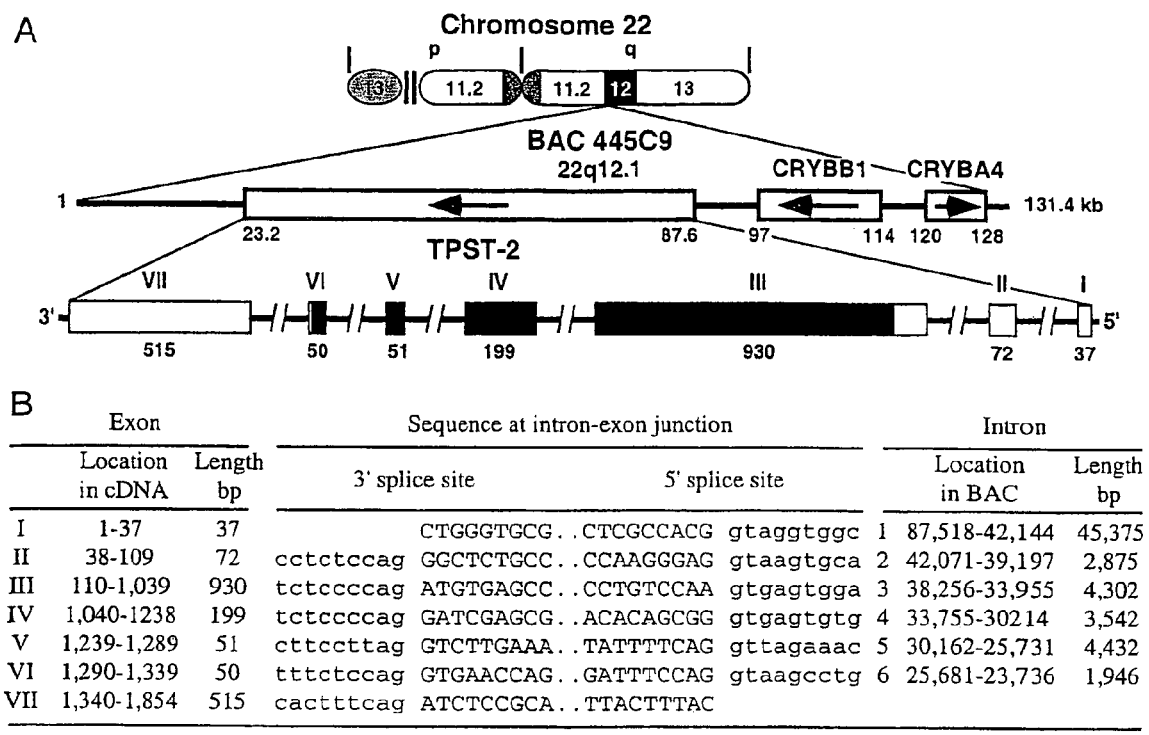

FIG. 12 is a schematic showing the genomic organization of the human TPST-2 gene. A. Location and orientation of the human TPST-2 gene in BAC clone 445C9 and structure of the human TPST-2 gene. Black rectangles represent coding regions and open rectangles represent noncoding regions of exons. The exon number is indicated in roman numerals above the exon and the number beneath the exons represent their lengths in bp. B. Sequences of the intron-exon junctions of the gene for human TPST-2. In FIG. 12, the sequence labelled "I" is SEQ ID NO:25; the sequence labelled "II" is SEQ ID NO:26; the sequence labelled "III" is SEQ ID NO:27; the sequence labelled "IV" is SEQ ID NO:28; the sequence labelled "V" is SEQ ID NO:29; the sequence labelled "VI" is SEQ ID NO:30; and the sequence labelled "VII" is SEQ ID NO:31.

FIG. 13 shows a multiple sequence alignment of the TPSTs of the present invention. The alignment of human TPST-1 (SEQ ID NO:1), human TPST-2 (SEQ ID NO:5), and *C. elegans* TPST-A (SEQ ID NO:9) and TPST-B (F42G9.8) (SEQ ID NO:11) was produced using the PILEUP program (Genetics Computer Group). Amino acid identities are highlighted. Residues homologous to those involved in co-substrate binding in the estrogen sulfotransferase crystal structure (35) are indicated by arrows above the sequence alignment.

SUMMARY OF THE INVENTION

Tyrosine O-sulfation is a post-translation modification of membrane and secretory proteins that occurs in all multicellular eukaryotes. Tyrosine O-sulfation is mediated by tyrosylprotein sulfotransferase (TPST) which catalyzes the transfer of the sulfuryl group from 3'-phosphoadenosine 5'-phosphosulfate (PAPS) to tyrosine residue(s) within highly acidic motifs of polypeptides (2, 4). The present invention comprises a TPST purified from rat liver microsomes and cloned human and mouse cDNAs that encode this enzyme designated herein as TPST-1. The human and mouse TPST-1 cDNAs encode N-glycosylated proteins of 370 amino acids with type II transmembrane topology and are broadly expressed in mammalian tissues as assessed by Northern blotting. The invention further comprises a second mammalian TPST, designated TSPT-2, having 377 and 376 amino acids, in the human and the mouse, respectively, and human and mouse cDNAs encoding TPST-2 and TPSTs from the nematode *Caenorhabditis. elegans*, designated TPST-A and TPST-B having 380, and 359 amino acids, respectively and cDNAs encoding TPST-A and TPST-B. The invention further comprises homologous proteins encoded by homologous cDNAs, homologous cDNAs, vectors and host cells which express the cDNAs, and methods of using the TPST proteins and cDNAs.

In further aspects, the present invention contemplates cloning vectors, which comprises the nucleic acid of the invention; and prokaryotic or eukaryotic expression vectors, which comprise the nucleic acid molecule of the invention, operatively associated with an expression control sequence. Accordingly, the invention further relates to a bacterial or mammalian cell transfected or transformed with an appropriate expression vector.

In yet a further aspect, the invention is directed to an antibody that binds to the TPST described above. Such an antibody can be a polyclonal or a monoclonal antibody. The invention is also directed to antibodies that bind to a ligand binding site of the TPST.

Accordingly, a primary object of the present invention is to provide a nucleic acid, in particular a DNA, that encodes a novel TPST or a fragment, or homologous derivative or analog thereof.

Yet a further object of the invention is to provide a cloning vector and an expression vector for such a nucleic acid molecule.

Still another object of the invention is to provide a recombinant cell line that contains such an expression vector.

It is also an object of the invention to provide the TPST, and fragments thereof, as the extra cytoplasmic domain thereof.

It is also an object of the invention to produce TPST using an expression system comprising a TPST-encoding polynucleotide.

Yet a further object of the invention is to provide monoclonal and polyclonal antibodies to such proteins.

It is another object of the present invention to provide a novel immunoassay for detecting such a tyrosylprotein sulfotransferase using such monoclonal antibodies.

These and other objects of the present invention can be better appreciated and understood by reference to the following drawings and detailed description of the invention.

DESCRIPTION OF THE INVENTION

Tyrosylprotein sulfotransferases are a family of enzymes that catalyze the post-translational sulfation of tyrosine residues within acidic motifs of many polypeptides in multicellular organisms. Tyrosine O-sulfation is a common post-translational modification shown to be important in protein-protein interactions in several systems. TPST has been purified herein from rat liver microsomes based on its affinity for the $NH_2$-terminus of PSGL-1, a known TPST substrate. Twelve tryptic peptides derived from the rat enzyme were used to isolate human and mouse cDNAs that encode novel Type II transmembrane proteins of 370 amino acid residues designated herein as TPST-1. All 12 tryptic peptides derived from the purified rat protein, comprising about 35% of the protein, are represented in the deduced amino acid sequence of the human and mouse cDNA of TPST-1. Human and mouse cDNAs encoding a second member of the TPST family, designated TPST-2 have also been isolated and expressed. The human and mouse TPST-2 cDNAs encode type II transmembrane proteins of 377 and 376 amino acid residues, respectively. Furthermore, the predicted molecular weights of the TPST-1 and TPST-2 coding region, in conjunction with the two potential N-glycosylation sites, are consistent with the sizes of the purified native or recombinant enzymes as assessed by SDS-PAGE. Both human and mouse TPST-1 and TPST-2 cDNAs induce overexpression of TPST activity when transfected into mammalian cells. These data conclusively demonstrate that the cDNAs encode tyrosylprotein sulfotransferases. Also, identified herein are two cDNAs from the nematode C. elegans encoding proteins of 380 amino acids and 359 amino acids, respectively designated TPST-A and TPST-B, type II proteins that induce overexpression of TPST activity when expressed in mammalian cells.

TPST-1 and TPST-2 specific transcripts are present in many mammalian tissues. In addition, both transcripts are present in multiple tumor cell lines and in human umbilical cell vein endothelial cells as assessed by Northern blotting (Y B Ouyang and K L Moore, unpublished observations). These data suggest that TPST-1 and TPST-2 are coexpressed in many, if not all, mammalian cells.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown herein or may be a different coding sequence which coding sequence, as a result of the redundancy or degeneracy of the genetic code, encodes the same, mature polypeptide as the DNA coding sequences shown herein.

The polynucleotides which encode for the mature polypeptides may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the amino acid sequences of SEQ ID NO:1, SEQ ID NO:3, SEQ ID NO:5, SEQ ID NO:7, SEQ ID NO:9, and SEQ ID NO:11. The variants of the polynucleotide may be naturally occurring allelic variants of the polynucleotides or nonnaturally occurring variants of the polynucleotides.

Thus, the present invention includes polynucleotides encoding the same mature polypeptides as shown in SEQ ID NO:1, SEQ ID NO:3, SEQ ID NO:5, SEQ ID NO:7, SEQ ID NO:9, and SEQ ID NO:11 as well as variants of such polynucleotides which variants encode for a fragment, derivative or analog of said polypeptides. Such nucleotide variants include deletion variants, substitution variants and addition or insertion variants.

As hereinabove indicated, the polynucleotide may have a coding sequence which is a naturally occurring allelic variant of the coding sequence of SEQ ID NO:2, SEQ ID NO:4, SEQ ID NO:6, SEQ ID NO:8, SEQ ID NO:10, or SEQ ID NO:12. As known in the art, an allelic variant is an alternate form of a polynucleotide sequence which may have a substitution, deletion or addition of one or more nucleotides, which does not substantially alter the function of the encoded polypeptide.

The present invention further relates to a TPST polypeptide which has the amino acid sequence of SEQ ID NO:1, SEQ ID NO:3, SEQ ID NO:5, SEQ ID NO:7, SEQ ID NO:9, or SEQ ID NO:11, as well as fragments, analogs and derivatives of such polypeptide.

The terms "fragment," "derivative," and "analog" when referring to the polypeptide of SEQ ID NO:1, SEQ ID NO:3, SEQ ID NO:5, SEQ ID NO:7, SEQ ID NO:9, and SEQ ID NO:11 mean a polypeptide which retains essentially the same biological functions or activities as such polypeptide. Thus, an analog includes a proprotein which can be activated by cleavage of a proprotein portion to produce an active mature polypeptide.

The polypeptide of the present invention may be a natural polypeptide or a synthetic polypeptide, or preferably a recombinant polypeptide.

The fragment, derivative or analog of the polypeptide of SEQ ID NO:1, SEQ ID NO:3, SEQ ID NO:5, SEQ ID NO:7, SEQ ID NO:9, or SEQ ID NO:11 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring) in a form sufficient to be useful in performing its inherent enzymatic function. For example, a naturally-occurring polynucleotide or polypeptide present in a living animal is not isolated, but the same polynucleotide or polypeptide separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, or a phage or other vectors known in the art. The engineered host cells can be cultured in conventional nutrient media modified as appropriate for activating promoters, selecting transformants or amplifying the TPST genes. The culture conditions, such as temperature, pH and the like, are those previously used with the host cell selected for expression, and will be apparent to the ordinary skilled artisan.

The TPST-encoding polynucleotides of the present invention may be employed for producing tyrosine sulfated polypeptides by recombinant techniques or synthetic in vitro techniques. Thus, for example, the TPST polynucleotides may be included along with a gene encoding a protein requiring tyrosine sulfation in any one of a variety of expression vectors for expressing the TPST and the protein requiring tyrosine sulfation. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable in the host. In one embodiment, the protein requiring tyrosine sulfation is P-selection glycoprotein ligand-1 or a portion thereof which has P-selectin binding activity.

The appropriate DNA sequence (or sequences) may be inserted into the vector by a variety of procedures. For example, the DNA sequence may be inserted into an appropriate restriction endonuclease sites(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein as described elsewhere herein.

As representative examples of appropriate hosts, there may be mentioned: bacterial cells, such as *E. coli, Streptomyces, Salmonella typhimurium*; fungal cells, such as yeast; insect cells such as *Drosophila* and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. Bacterial: pQE70, pQE60, pQE-9 (Qiagen), pbs, pD10, phagescript, psiX174, pBluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art.

In a further embodiment, the present invention relates to host cells containing the above-described constructs. The host cells may be obtained using techniques known in the art. Suitable host cells include prokaryotic or lower or higher eukaryotic organisms or cell lines, for example bacterial, mammalian, yeast, or other fungi, viral, plant or insect cells. Methods for transforming or transfecting cells to express foreign DNA are well known in the art (See for example, Itakura et al., U.S. Pat. No. 4,704,362; Hinnen et al., PNAS USA 75:1929-1933, 1978; Murray et al., U.S. Pat. No. 4,801,542; Upshall et al., U.S. Pat. No. 4,766,075; and Sambrook et al., Molecular Cloning: A Laboratory Manual 2nd Ed., Cold Spring Harbor Laboratory Press, 1989), all of which are incorporated herein by reference.

Introduction of the construct into the host cell can be effected by methods well known in the art such as by calcium phosphate transfection, DEAE-Dextran mediated transfection, or electroporation. (Davis, L., Dibner, M. Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eurkaryotes may be increased by inserting an enhancer sequence into the vector.

Enhancers are cis-acting elements of DNA, usually about from 10 to 300 bp that act on a promoter to increase its transcription. Examples include the SV40 enhancer, a cytomegalovirus early promoter enhancer, the polyoma enhancer, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extraccellular medium. Optionally, the heterologous sequence can encode a fusion protein including an N-terminal or C-terminal identification peptide imparting desired characteristics, e.g., stabilization for simplified purification of expressed recombinant product.

Useful expression vectors for bacterial use are constructed by inserting one or more structural DNA sequences encoding one or more desired proteins together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. Coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322, (ATCC 37017). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents. Such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of transcribing compatible vectors, for example, the C127, 293, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The TPST polypeptides or portions thereof can be recovered and purified from recombinant cell cultures by methods including but not limited to ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography, alone or in combination. Protein refolding steps can be used as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

A recombinant TPST of the invention, or functional fragment, derivative or analog thereof, may be expressed chromosomally, after integration of the TPST coding sequence by recombination. In this regard any of a number of amplification systems may be used to achieve high levels of stable gene expression (See Sambrook et al., 1989, supra).

The cell into which the recombinant vector comprising the nucleic acid encoding the TPST is cultured in an appropriate cell culture medium under conditions that provide for expression of the TPST by the cell. If full length TPST is expressed, the expressed protein will comprise an integral membrane binding portion. If a TPST lacking a membrane binding domain is expressed, the expressed soluble TPST can then be recovered from the culture according to methods well known in the art. Such methods are described in detail, infra.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab (F(ab')2 fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by other appropriate forms of administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495-497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to immunogenic polypeptide products of this invention.

The polyclonal or monoclonal antibodies may be labelled with a detectable marker including various enzymes, fluorescent materials, luminescent materials and radioactive materials. Examples of suitable enzymes include horseradish peroxidase, alkaline phosphatase, β-galactosidase, or acetylcholinesterase; examples of suitable fluorescent materials include umbeliferone, fluorescein, fluorescein isothiocyanate, rhodamine, dichlorotriazinylamine fluorescein, dansyl chloride or phycoerythrin; an example of a luminescent materials include luminol and aequorin; and examples of suitable radioactive material include $S^{35}$, $Cu^{64}$, $Ga^{67}$, $Zr^{89}$, $Ru^{97}$, $Tc^{99m}$, $Rh^{105}$, $Pd^{109}$, $In^{111}$, $I^{123}$, $I^{125}$, $I^{131}$, $Re^{186}$, $Au^{198}$, $Au^{199}$, $Pb^{203}$, $At^{211}$, $Pb^{212}$ and $Bi^{212}$. The antibodies may also be labelled or conjugated to one partner of a ligand binding pair. Representative examples include avidin-biotin and riboflavin-riboflavin binding protein.

Methods for conjugating or labelling the antibodies discussed above with the representative labels set forth above may be readily accomplished using conventional techniques such as described in U.S. Pat. No. 4,744,981 (Trichothecene Antibody); U.S. Pat. No. 5,106,951 (Antibody Conjugate); U.S. Pat. No. 4,018,884 (Fluorengenic Materials and Labelling Techniques); U.S. Pat. No. 4,897,255 (Metal Radionucleotide Labeled Proteins for Diagnosis and Therapy); U.S. Pat. No. 4,988,496 (Metal Radionuclide Chelating Compounds for Improved Chelation Kinetics); Inman, Methods in Enzymology, Vol. 34, Affinity Techniques, Enzyme Purification; Part B, Jacoby and Wichek (eds) Academic Press, New York, P. 30, 1974; and Wilcheck and Bayer, The Avidin-Biotin Complex in Bioanalytical Applications Anal. Biochem. 171:1-32, 1988.

Due to the degeneracy of nucleotide coding sequences, other DNA sequences which encode substantially the same amino acid sequence as a TPST gene described herein may be used in the practice of the present invention. These include but are not limited to nucleotide sequences comprising all or portions of TPST genes which are altered by the substitution of different codons that encode the same amino acid residue within the sequence, thus producing a silent change. Likewise, the TSPT derivatives of the invention include, but are not limited to those containing, as a primary amino acid sequence, all or part of the amino acid sequence of the TSPT protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent. Substitutions for an amino acid within the sequence may be selected from but are not limited to other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) aminos acids include aspartic acid and glutamic acid.

The genes encoding TPST derivatives and analogs of the invention can be produced by various methods known in the art. The manipulations which result in their production can occur at the gene or protein level. For example, the cloned TPST gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of TPST, care should be taken to ensure that the modified gene remains within the same translational reading frame as the TPST coding sequence, uninterrupted by translation stop signals, in the gene region where the desired activity is encoded.

Within the context of the present invention, TPST may include various structural forms of the primary protein which retain biological activity. For example, TPST polypeptide may be in the form of acidic or basic salts or in neutral form. In addition, individual amino acid residues may be modified by oxidation or reduction. Furthermore, various substitutions, deletions or additions may be made to the amino acid or nucleic acid sequences, the net effect being that biological activity of TPST is retained. Due to code degeneracy, for example, there may be considerable variation in nucleotide sequences encoding the same amino acid.

Mutations in nucleotide sequences constructed for expression of derivatives of TPST polypeptide must preserve the reading frame phase of the coding sequences. Furthermore, the mutations will preferably not create complementary regions that could hybridize to produce secondary mRNA structures, such as loops or hairpins which could adversely affect translation of the mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site specific mutagenesis procedures may be employed to provide an altered gene having particular codons altered according the substitution, deletion, or insertion required. Deletions or truncations of TPSTs may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al., (Molecular Cloning: A Laboratory Manual, 2nd Ed., Cold Spring Harbor Laboratory Press, 1989).

As noted above, a nucleic acid sequence encoding a TPST can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated TPST gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479-488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in PCR Technology: Principles and Applications for DNA amplification, H. Erlich, ed., Stockton Press, Chapter 6, pp. 61-70).

It is well known in the art that some DNA sequences within a larger stretch of sequence are more important than others in determining functionality. A skilled artisan can test allowable variations in sequence, without expense of undue experimentation, by well-known mutagenic techniques which include, but are not limited to, those discussed by D. Shortle et al. (1981) Ann. Rev. Genet. 15:265; M. Smith (1985) ibid. 19:423; D. Botstein and D. Shortle (1985) Science 229:1193; by linker scanning mutagenesis (S. McKnight and R. Kingsbury (1982) Science 217:316), or by saturation mutagenesis (R. Myers et al. (1986) Science 232:613). These variations may be determined by standard techniques in combination with assay methods described herein to enable those in the art to manipulate and bring into utility the functional units of upstream transcription activating sequence, promoter elements, structural genes, and polyadenylation signals. Using the methods described herein the skilled artisan can without application of undue experimentation test altered sequences within the upstream activator for retention of function. All such shortened or altered functional sequences of the activating element sequences described herein are within the scope of this invention.

The nucleic acid molecule of the invention also permits the identification and isolation, or synthesis of nucleotide sequences which may be used as primers to amplify a nucleic acid molecule of the invention, for example in the polymerase chain reaction (PCR) which is discussed in more detail below. The primers may be used to amplify the genomic DNA of other species which possess TPST activity. The PCR amplified sequences can be examined to determine the relationship between the various TPST genes.

The length and bases of the primers for use in the PCR are selected so that they will hybridize to different strands of the desired sequence and at relative positions along the sequence such that an extension product synthesized from one primer when it is separated from its template can serve as a template for extension of the other primer into a nucleic acid of defined length.

Primers which may be used in the invention are oligonucleotides of the nucleic acid molecule of the invention which occur naturally as in purified restriction endonuclease digest or are produced synthetically using techniques known in the art such as for example, phosphotriester and phosphodiesters methods (See Good et al.,. Nucl. Acid Res 4:2157, 1977) or automated techniques (See for example, Conolly, B. A. Nucleic Acids Res. 15:15(8\7): 3131, 1987). The primers are capable of acting as a point of initiation of synthesis when placed under conditions which permit the synthesis of a primer extension product which is complementary to the DNA sequence of the invention i.e., in the presence of nucleotide substrates, an agent for polymerization such as DNA polymerase and at suitable temperature and pH. Preferably, the primers are sequences that do not form secondary structures by base pairing with other copies of the primer or sequences that form a hair pin configuration. The primer may be single or double-stranded. When the primer is double-stranded it may be treated to separate its strands before using to prepare amplification products. The primer preferably contains between about 7 and 25 nucleotides.

The primers may be labelled with detectable markers which allow for detection of the amplified products. Suitable detectable markers are radioactive markers such as $P^{32}$, $S^{35}$, $I^{125}$, and $H^3$, luminescent markers such as chemiluminescent markers, preferably luminol, and fluorescent markers, preferably dansyl chloride, fluorcein-5-isothiocyanate, and 4-fluor-7-nitrobenz-2-axa-1,3 diazole, enzyme markers such as horseradish peroxidase, alkaline phosphatase, β-galactosidase, acetylchoilinesterase, or biotin.

It will be appreciated that the primers may contain non-complementary sequences provided that a sufficient amount of the primer contains a sequence which is complementary to a nucleic acid molecule of the invention or oligonucleotide sequence thereof, which is to be amplified. Restriction site linkers may also be incorporated into the primers allowing for digestion of the amplified products with the appropriate restriction enzymes facilitating cloning and sequencing of the amplified product.

In an embodiment of the invention a method of determining the presence of a nucleic acid molecule having a sequence encoding a TPST or a predetermined oligonucleotide fragment thereof in a sample, is provided comprising treating the sample with primers which are capable of amplifying the nucleic acid molecule or the predetermined oligonucleotide fragment thereof in a polymerase chain reaction to form amplified sequences, under conditions which permit the formation of amplified sequences and assaying for amplified sequences.

The polymerase chain reaction refers to a process for amplifying a target nucleic acid sequence as generally described in Innis et al., Academic Pres, 1990; in Mullis et. al., U.S. Pat. No. 4,863,195 and Mullis, U.S. Pat. No. 4,683,202 which are incorporated herein by reference. Conditions for amplifying a nucleic acid template are described in M. A. Innis and D. H. Gelfand, PCR Protocols, A Guide to Methods and Applications, M. A. Innis, D. H. Gelfand, J. J. Shinsky and T. J. White eds, pp 3-12, Academic Press 1989, which is also incorporated herein by reference.

It will be appreciated that other techniques such as the Ligase Chain Reaction (LCR) and NASBA may be used to amplify a nucleic acid molecule of the invention. In LCR, two primers which hybridized adjacent to each other on the target strand are ligated in the presence of the target strand to produce a complementary strand (Barney in "PCR Methods and Applications", August 1991, Vol 1(1), page 4, and European Published Application No. 0320308, published Jun. 14, 1989. NASBA is a continuous amplification method using two primers, one incorporating a promoter sequence recognized by an RNA polymerase and the second derived from the complementary sequence of the target sequence to the first primer (U.S. Pat. No. 5,130,238 to Malek).

The present invention also provides novel fusion proteins in which any of the enzymes of the present invention are fused to a polypeptide such as protein A, streptavidin, fragments of c-myc, maltose binding protein, IgG, IgM, amino acid tag, etc. In addition, it is preferred that the polypeptide fused to the enzyme of the present invention is chosen to facilitate the release of the fusion protein from a prokaryotic cell or a eukaryotic cell, into the culture medium, and to enable its (affinity) purification and possibly immobilization on a solid phase matrix.

In another embodiment, the present invention provides novel DNA sequences which encode a fusion protein according to the present invention.

The present invention also provides novel immunoassays for the detection and/or quantitation of the present enzymes in a sample. The present immunoassays utilize one or more of the present monoclonal or polyclonal antibodies which specifically bind to the present enzymes. Preferably the present immunoassays utilize a monoclonal antibody. The present immunoassay may be a competitive assay, a sandwich assay, or a displacement assay, such as those described in Harlow, E. et al., *Antibodies. A Laboratory Manual*, Cold Spring Harbor Laboratory Press, Cold Spring Harbor, N.Y. (1988) and may rely on the signal generated by a radiolabel, a chromophore, or an enzyme, such as horseradish peroxidase.

It is known that sulfated tyrosine residues are essential components of the glycoprotein ligand (PSGL-1) P-selectin. These receptor-counter-receptor pairs operate to enable leukocytes (neutrophils, monocytes, eosinophils, lymphocytes in general (in recirculatary events), and some kinds of T lymphocytes) to leave the vascular tree and participate in normal inflammatory events in humans, or in pathological inflammatory events in humans (like ARDS, tissue-reperfusion injury, and a host of other such events). Since tyrosylprotein sulfotransferase is important in causing sulfation of PSGL-1, pharmacologic inhibitors of this enzyme will diminish binding of neutrophils to endothelial cells and thus act as anti-inflammatory pharmaceutical agents for use in humans or other animals in acute and chronic selectin-dependent inflammatory states. The tyrosylprotein sulfotransferases described herein therefore represent tools to be used in an assay for identifying compounds that inhibit these enzymes, either through "screening" methods to identify such inhibitory compounds in natural product or chemical libraries (using recombinant enzyme or cell lines expressing this enzyme, in screening assays), or through "rational drug design" strategies (via solution of the enzyme's tertiary structure with the aid of recombinant enzyme, followed by design or identification of molecules that inhibit the enzyme's catalytic activity or other essential function). It is well within the ability of a person of ordinary skill in the art to develop and use such screening methods given the knowledge of the amino acid and DNA sequences of the TPSTs provided herein.

Compounds, for example, peptides identified during the screening process, which inhibit TPST activity or expression are preferably administered in a pharmaceutically acceptable vehicle. Suitable pharmaceutical vehicles are known to those skilled in the art. For parenteral administration, the compound will usually be dissolved or suspended in sterile water or saline. For enteral administration, the compound will be incorporated into an inert carrier in tablet, liquid, or capsular form. Suitable carriers may be starches or sugars and include lubricants, flavorings, binders, and other materials of the same nature. The compounds can also be administered locally by topical application of a solution, cream, gel, or polymeric material (for example, a Pluronic™, BASF).

Alternatively, the compound may be administered in liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14, "Liposomes", *Drug Carriers in Biology and Medicine*, pp. 287-341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. Nos. 4,906,474, 4,925,673, and 3,625,214.

The peptides, for example, can also be administered as a pharmaceutically acceptable acid- or base-addition salt, formed by reaction with inorganic acids. The peptides are generally active when administered parenterally in amounts above about 1 μg/kg of body weight. Based on extrapolation from other proteins, for treatment of most inflammatory disorders, the dosage range will be between 0.1 to 70 mg/kg of body weight. This dosage will be dependent, in part, on whether one or more peptides are administered.

Absence of tyrosylprotein sulfotransferase conceivably could be associated with a detrimental phenotype, DNA sequence polymorphisms, including restriction fragment length polymorphisms, within or linked to the gene corresponding to this cloned gene segment may be used to genotype individuals at this locus, for the purpose of genetic counseling. Likewise, the molecular basis for such detrimental phenotypes might be elucidated via the study of the gene segment described here, should it be causally-related to such phenotypes.

As noted and described elsewhere herein, the TPST enzymes of the present invention can be used in vitro in a synthetic process to cause the sulfation of a protein comprising one or more tyrosine residues. In said process, the protein or peptide to which sulfate is to be added is combined with the TPST enzyme and with a sulfate donor source such as PAPS sulfate under suitable conditions. In an especially preferred embodiment, the TPST is used in a synthetic process to sulfate P-selectin glycoprotein ligand-1, or a portion thereof comprising tyrosine.

The invention will be more fully understood by reference to the following examples. However, the examples are merely intended to illustrate embodiments of the invention and are not to be construed to limit the scope of the invention.

EXAMPLES

Assay of Sulfotransferase Activity. TPST activity was determined by measuring the transfer of [$^{35}$S]sulfate from [$^{35}$S]PAPS (Dupont/NEN) to an immobilized peptide. The peptide (QATEYEYLDYDFLPEC (SEQ ID NO:22)) represents the NH$_2$-terminal 15 residues of the mature PSGL-1 polypeptide to which a carboxy terminal cysteine residue was added. It spans three potential tyrosine sulfation sites that have been shown to be sulfated in mammalian cells (7,22,23). The peptide was linked via the cysteine residue to iodoacetamide-activated resin (UltraLink™ Iodoacetyl, Pierce) at a density of 1.5-3.0 μmol/ml resin. The enzyme assay was performed by combining 10 μl of peptide-derivitized beads with 2-20 μl of sample in 40 mM PIPES, pH 6.8, 0.3 M NaCl, 20 mM MnCl$_2$, 50 mM NaF, 1% Triton X-100, 1 mM 5'AMP in a final volume of 130 ml. The assay was initiated by addition of 0.5 μCi of [$^{35}$S]PAPS (about 1.7 μM). After 30 min at 37° C., the reaction beads were washed extensively with 6 M guanidine at 65° C. and the radioactivity incorporated into the beads determined by liquid scintillation counting. The reaction rate was optimal at pH 6.8-7.0, 0.3 M NaCl, and 2 μM PAPS and was linear with respect to time and sample input. Transfer of [$^{35}$S]sulfate was inhibited by free peptide with an $IC_{50}$ equimolar to the concentration of immobilized peptide in the assay. One unit of activity was defined as 1 pmol of product formed per minute.

Purification of Tyrosylprotein Sulfotransferase. Male 200-300 gm Sprague-Dawley rats (Harlan) were anesthetized with $CO_2$, decapitated, and the livers excised and immersed in cold homogenization buffer [10 mM Tris-HCl (pH 7.5), 1.5 mM $MgCl_2$, 250 mM sucrose, 0.5 mM DTT, 0.5 mM PMSF]. All further steps are performed at 4° C. Livers were minced, suspended in 30 ml/gm liver of buffer, passed twice through a Zeigler-Pettit continuous-flow homogenizer (24), and the homogenate centrifuged (10 min, 800 g). The post-nuclear supernatant was centrifuged (90 min, 28,000 g), the microsomal pellet suspended in 1.5 ml/gm liver of 2% Triton X-100, 20 mM TAPS (pH 9.0), 0.5 mM PMSF, 10 µg/ml leupeptin/antipain, and stirred for 1 h. PMSF was added to 0.5 mM and the microsomal extract was clarified by centrifugation (60 min, 40,200 g). To the supernatant was added glycerol to 10% (w/v), MOPS (pH 7.5) to 50 mM, and PMSF to 0.5 mM.

Extract from 120 livers was applied at 25 cm/h to a 5×20 cm Toyopearl SP-550C column (TosoHaas) equilibrated with 50 mM MOPS (pH 7.5), 10% (w/v) glycerol, 0.05% Triton X-100 (Buffer A). The column was washed with Buffer A, then eluted with 0.25 M NaCl in Buffer A, followed by 1 M NaCl in Buffer A. After this and subsequent steps, fractions were frozen in liquid $N_2$ and stored at −80° C.

Enzyme eluted from Toyopearl SP-550C was pooled and diluted with Buffer A to a conductivity equivalent to 0.15 M NaCl. The material was applied at 110 cm/h to a PSGL-1 peptide column (1.5×6 cm, 1.5 µmol peptide/ml) equilibrated with 0.1 M NaCl in 50 mM MOPS (pH 7.5), 10% (w/v) glycerol, 0.02% Triton X-100 (Buffer B). The column was washed with 0.1 M NaCl in Buffer B, then step eluted with 0.35 M NaCl, followed by 1 M NaCl in Buffer B at 55 cm/h.

Fractions from the PSGL-1 peptide column were pooled and dialyzed against Buffer B until the conductivity was equivalent to 0.2 M NaCl. The material was applied at 150 cm/h to an ethanolamine UltraLink™ precolumn (1×10 cm) in series with a PSGL-1 peptide column (0.5×20 cm, 2.7 µmol peptide/ml) equilibrated with 0.15 M NaCl in Buffer B. After washing with 0.2 M NaCl in Buffer B the precolumn was removed from the circuit. The column was eluted with 0.3 M NaCl in Buffer B and then developed with a 20 ml linear 0.3 to 1 M NaCl gradient at 30 cm/h.

In gel Tryptic digestion, HPLC Separation, and Microsequencing. Proteins were separated by SDS-PAGE and stained with Coomassie Blue. Protein bands were excised and subjected to in gel reduction, S-carboxyamidomethylation, and tryptic digestion (Promega). A 10% aliquot of the resultant mixture was analyzed as follows. Sequence information was determined by capillary reverse-phase chromatography (180 mm×15 cm, LC Packings) coupled to the electrospray ionization source of a quadrupole ion trap mass spectrometer (Finnigan LCQ). The instrument was programmed to acquire successive sets of three scan modes consisting of full scale MS over the m/z range of 395-1200 amu, followed by two data dependent scans on the most abundant ion in the full scan. These data dependent scans allowed the automatic acquisition of a high resolution scan to determine charge state and exact mass, and MS/MS spectra for peptide sequence information. Interpretation of the MS/MS spectra of the peptides was facilitated by searching the NCBI non-redundant and EST databases with the algorithm SEQUEST (25). The remainder (90%) of the peptide mixture was separated by microbore HPLC using a 1 mm×150 mm Zorbax C18 reverse-phase column on a Hewlett-Packard 1090 HPLC/1040 diode array detector. Optimum fractions were chosen based on differential UV absorbance at 205, 277, and 292 nm, peak symmetry, and resolution; then further screened for length and homogeneity by matrix-assisted laser desorption time-of-flight mass spectrometry (MALDI-MS) on a Thermo BioAnalysis Lasermat 2000 (Hemel England). Strategies for peak selection, reverse-phase separation, and Edman microsequencing have been previously described (26). Tryptic peptides were submitted to automated Edman degradation on an Applied Biosystems 477A protein sequencer.

Expression of Recombinant TPST-1 in Mammalian Cells. The pcDNA3.1(+) vector (Invitrogen) was modified for expression of fusion proteins containing an $NH_2$-terminal epitope for HPC4, a $Ca^{2+}$-dependent monoclonal antibody to Protein C (27). The NheI and BamHI fragment in the multiple cloning site of the vector was replaced with a 48 bp double-stranded oligonucleotide with a 5' NheI half site and a 3' BamHI half site containing an ideal Kozak sequence immediately upstream to the sequence encoding the HPC4 epitope.

The human TPST-1 coding sequence was amplified by Advantage™ KlenTaq polymerase using EST clone #116978 as template. The primers used were: top strand 5'-CGGGATCCGGTTGGGAAGCTGAAGCAGAAC-3' (SEQ ID NO:32), bottom strand 5'-GG ACTAGTATTACTCCACTTGCTCCGTCTG-3' (SEQ ID NO:33). The PCR introduced a BamH1 site at the initiation codon and an SpeI site after the termination codon (underlined). The cycling parameters were: 25 cycles, denaturation, 94° C., 30 s; annealing, 55° C., 30 s; extension, 68° C., 2 min. The product was gel purified, ligated into the pGEM-T (Promega), and sequenced on both strands. The insert was excised using BamHI and ApaI and directionally cloned into unique BamHI and ApaI sites in the multiple cloning site of the modified pcDNA3.1(+) vector. In the fusion protein the native initiating methionine is replaced with 15 residues, containing the HPC4 epitope (M EDQVDPRLIDGKDP (SEQ ID NO:34)).

Chinese hamster ovary cells (CHO-K1) were grown in high-glucose Alpha modified Eagle's media containing 10% FCS, 2 mM glutamine at 37° C. and 5% $CO_2$. The human embryonic kidney cell line 293-T was grown in low-glucose Dulbecco's modified Eagle's media containing 10% FCS, 2 mM glutamine at 37° C. and 5% $CO_2$. Cells were transfected with empty vector or vector containing cDNAs encoding human TPST-1-HPC4 fusion protein or mouse TPST-1 using Lipofectamine (Gibco/BRL) according to the instructions of the supplier. The media was changed at 24 h and after an additional 24 h the conditioned media was collected. The cell monolayers were washed with $Ca^{2+}/Mg^{2+}$-free Hank's balanced salt solution and the cells released from the plates. The cells were pelleted by centrifugation and extracted with 1% Triton X-100, 0.1 M NaCl, 20 mM TAPS (pH 9.0), 10 µg/ml leupeptin/antipain, 5 mM benzamidine. Extracts and conditioned media were clarified by centrifugation (15 min, 10,000 g) and stored at −80° C.

Expression of Recombinant TPST-2 in Mammalian Cells. The pcDNA3.1(+) vector (Invitrogen, Carlsbad, Calif.) was modified for expression of full-length TPST fusion proteins containing an N-terminal epitope for HPC4, a $Ca^{2+}$-dependent monoclonal antibody to Protein C, as previously described herein. Full-length human and mouse TPST-2 coding sequences were amplified by Taq polymerase (Promega, Madison, Wis.) using expressed sequence tag (EST) clones 810937 and 569461 as templates, respectively. The primers used were: top strand 5'-CG<u>GGATCC</u>GCGCCTGTCGGTGCGTA-3' (SEQ ID NO:35), bottom strand 5'-G<u>GAATTC</u>TGGAAATCACGAGCTTCC-3' (SEQ ID NO:36). The cycling parameters were: 25 cycles; denaturation, 94° C. for 30 s; annealing, 55° C. for 30 s; extension, 68° C. for 2 min. The PCR introduced a BamH1 site in place of the native initiation codon and an EcoRI site after the termination codon (underlined). The products were gel purified, litigated into the pGEM-T (Promega), and sequenced on both strands. The inserts were excised using BamHI and EcoRI and directionally cloned into unique BamHI and EcoRI sites in the multiple cloning site of the modified pcDNA3.1(+) vector. In the fusion proteins the native initiating methionine is replaced with 15 residues containing the HPC4 epitope (M<u>EDQVDPRLIDGK</u>DP (SEQ ID NO:34)).

The pcDNA3.1(+) vector was also modified for expression of soluble fusion proteins containing an N-terminal HPC4 epitope. The HindIII and BamHI fragment in the multiple cloning site of the vector was replaced with a 103 bp double-stranded oligonucleotide (Integrated DNA Technologies, Inc., Coralville, Iowa) with a 5' HindIII half site and a 3' BamHI half site containing an ideal Kozak sequence followed by the nucleotide sequence encoding the transferrin single peptide and the HPC4 epitope. cDNAs encoding soluble forms of human and mouse TPST-2 were amplified by Taq polymerase using the full-length cDNAs as templates, respectively. The primers used for amplification of soluble TPST-2 were: top strand for human TPST-2; 5'CG<u>GGATCC</u>AGGACAGCAGGTGCTAGAG-3' (SEQ ID NO:37), top strand for mouse TPST-2; 5'-CG<u>GGATCC</u>AGGGCAGCAAGTACTGGAG-3' (SEQ ID NO:38), and bottom strand for human and mouse TPST-2; 5'-G<u>GAATTC</u>TGGAAATCACGAGCTTCC-3' (SEQ ID NO:36). The PCR introduced a BamH1 site at the 5' end and an EcoRI site after the termination codon (underlined). The cycling parameters were: 25 cycles, denaturation, 94° C., 30 s; annealing, 55° C., 30 s; extension, 72° C., 2 min. After the PCR both products were gel purified. The TPST-2 product was digested with BamHI and EcoRI and cloned into unique BamHI and EcoRI sites in the multiple cloning site of the vector. In the fusion proteins the native N-terminal 24 amino acids of TPST-2, including the cytoplasmic and transmembrane domain were replaced with the 19 residue cleavable transferrin signal peptide (MRLAVGALLVCAVLGLCLA (SEQ ID NO:39)) followed by the 12 residue HPC4 epitope. Thus, the N-terminus of the both recombinant soluble enzymes is NH$_2$-<u>EDQVDPRLIDGK</u>DPG$^{25}$Q (SEQ ID NO:40) (HPC4 epitope is underlined) after signal peptide cleavage. The predicted molecular masses of soluble human and mouse TPST-2 fusion proteins are 40,940 Da and 41,152 Da, respectively.

Peptide Antibody Production. A peptide corresponding to residues 360-376 (<u>C</u>GYFQVNQVSTSPHLGSS (SEQ ID NO:41)) of the cDNA-derived amino acid sequence of mouse TPST-2 was synthesized on an Applied Biosystems Model 431 peptide synthesizer. The peptide was coupled to maleimide-activated keyhole lipet hemocyanin through the added N-terminal cysteine (underlined) and injected into New Zealand White rabbits (Cocalico Biologicals, Inc. Reamstown, Pa.). Immune sera were collected and tested by Western analysis of extracts of 293-T cells transfected with cDNAs encoding mouse and human TPST-1 and TPST-2.

The antiserum recognized two closely spaced polypeptides of about 47 kDa in extracts of cells overexpressing full length mouse and human TPST-2, but not in cells overexpressing mouse or human TPST-1.

Purification of TPST-1 Fusion Protein. Human TPST-1-HPC4 was purified from extracts of ten 162 cm$^2$ dishes of transiently transfected 293-T cells. The extract was adjusted to 10% (w/v) glycerol, 50 mM MOPS (pH 7.5), and 5 mM CaCl$_2$ and incubated with 0.5 ml of HPC4-UltraLink (5 mg antibody/ml resin) for 15 h at 4° C. The resin was packed into a column and washed with 2 M NaCl, 20 mM MOPS (pH 7.5), 2 mM CaCl$_2$, 0.1% Triton X-100 followed by 0.15 M NaCl in the same buffer. Bound protein was eluted with 10 mM EDTA, 0.15 M NaCl, 20 mM MOPS (pH 7.5), 0.1% Triton X-100. Fractions were assayed for protein content and TPST activity. Samples were electrophoresed on 10% SDS polyacrylamide gels and proteins transferred to Hybond-P membranes (Amersham). The membranes were blocked, probed with HPC4, and bound antibody detected with enhanced chemiluminescence using horseradish peroxidase-conjugated anti-mouse immunoglobulin (Amersham).

Purified human TPST-1 fusion protein prepared as described above, was treated with 0.3 M βME, 5 mM EDTA (2 min, 100° C.), and incubated in the presence or absence of 2.5 units of peptide N-glycosidase F (Oxford Glycosystems) for 12 h at 37° C. Samples were analyzed by SDS-PAGE followed by Western blotting with HPC4.

Northern Blot Hybridization. For human TPST-1 a 1138 bp partial cDNA, corresponding to nt 1-1138, was excised from EST #116978 using EcoRI. For mouse TPST-1 a 1560 bp EcoRI-XhoI fragment of EST #567635, which corresponds to nt 321-1881 of the cDNA, was used as a probe. Probes were labeled with [α-$^{32}$P]dCTP (Dupont/NEN) using random hexamer priming with Klenow fragment (Pharmacia). Multiple tissue Northern blots of poly(A)$^+$ RNA (Clontech) were prehybridized for 60 min at 68° C. and hybridized with $^{32}$P-labeled probe overnight at 68° C. The blots were washed twice with 2×SSC, 0.1% SDS for 20 min at 22° C. and twice with 0.1×SSC, 0.1% SDS for 20 min at 50° C. The membrane was exposed to a phosphorimager screen for 16 h at room temperature.

Figure 1:
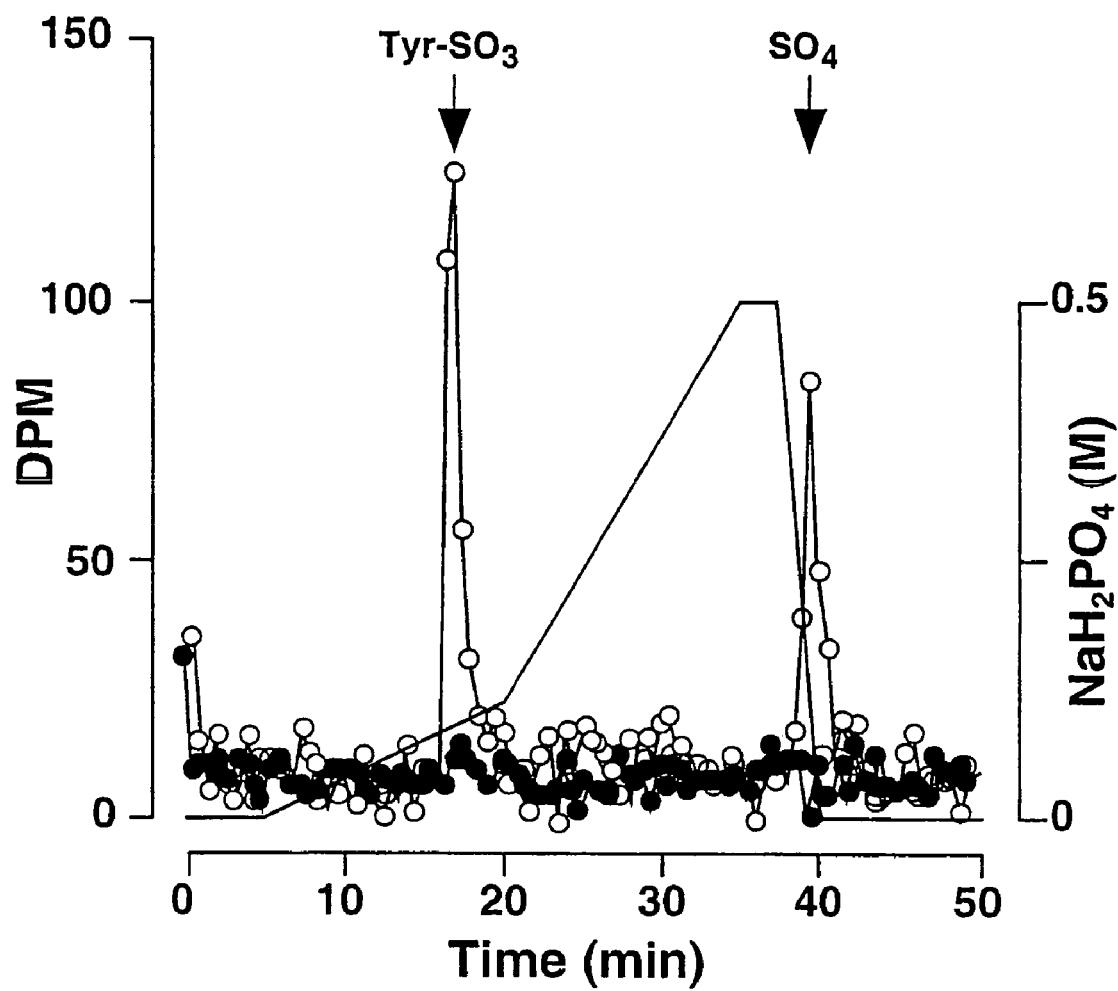
FIG. 1 is a graph showing sulfotyrosine analysis. Microsomal extract (open circles) or buffer (closed circles) was combined with PSGL-1 peptide-derivatized beads in the presence of [$^{35}$S]PAPS and incubated under standard assay conditions. The beads were washed extensively and then treated with proteinase K. Released material was hydrolyzed under alkaline conditions, and analyzed by HPLC as described in Methods.

Validation of TPST Assay. Crude rat liver microsomal extract or buffer were combined with peptide-derivatized beads and [$^{35}$S]PAPS and incubated under standard assay conditions. After washing, the beads were treated with proteinase K (1 mg/ml, 37° C., 15 h) in 50 mM Tris-HCl (pH 8.0), 1 mM CaCl$_2$. Released material was hydrolyzed in 1 M NaOH at 110° C. for 24 h under N$_2$ and the hydrolysate analyzed by HPLC as described (7). This analysis revealed two [$^{35}$S]-labeled peaks which co-migrated with tyrosine sulfate and free sulfate standards, respectively (FIG. 1). In the absence of enzyme, [$^{35}$S]-labeled products were not detected. This proves that peptidyl [$^{35}$S]tyrosine sulfate was formed, and that non-enzymatic tyrosine O-sulfation of substrate does not occur under these assay conditions.

Rat Liver TPST Co-Purifies with a Polypeptide of about 50 kDA. To determine whether rat liver TPST-1 activity was membrane-associated, post-nuclear supernatants were centrifuged (60 min, 100,000 g) and the supernatant (cytosol) and pellet (microsomes) were collected and assayed. More than 98% of the TPST-1 activity in crude homogenate was in the microsomal fraction. When microsomes were solubilized with 2% Triton X-100, 20 mM TAPS (pH 9.0) and centrifuged (60 min, 100,000 g), >95% of the enzyme activity was recovered in the 100,000 g supernatant. TPST-1 activity in post-nuclear supernatant of rat liver homogenate was not detectable when detergent was excluded from the assay mixture, consistent with a lumenal orientation of the enzyme active site.

The 18,400-fold enrichment of TPST from 2 kg of rat liver is summarized in Table 1. Microsomal extracts were prepared from 120 rat livers and applied to a Toyopearl SP-550C column. The column was washed and sequentially eluted with 0.35 M NaCl and 1 M NaCl. The bulk of the bound enzyme activity eluted with 1 M NaCl. Enzyme activity eluted from Toyopearl SP-550C from two 120 rat preps was diluted and applied to a PSGL-1 peptide column. The column was washed and sequentially eluted with 0.35 M NaCl and 1 M NaCl. Most of the bound enzyme activity eluted with 1 M NaCl.

Figure 2:
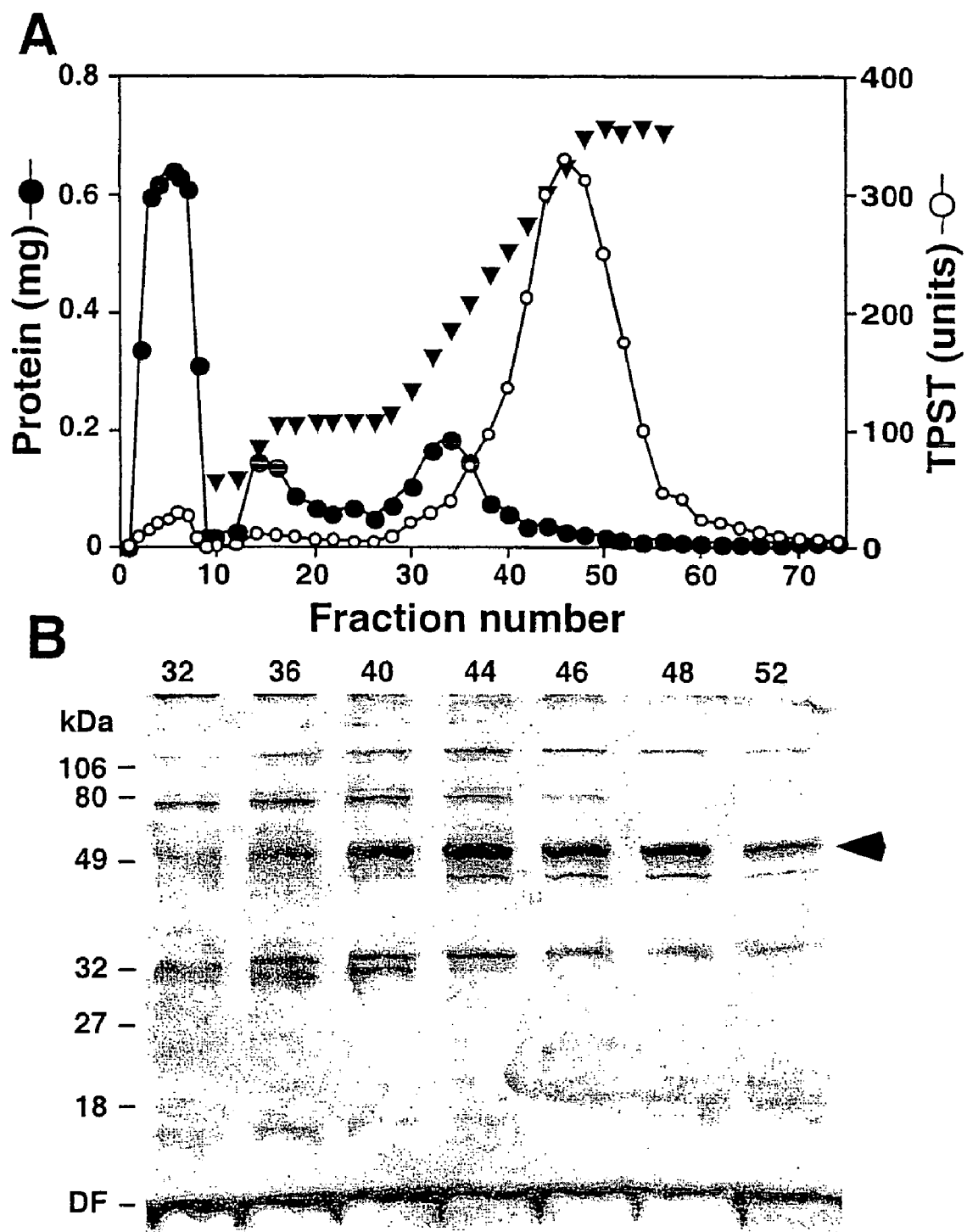
FIG. 2 shows a graph (A) of a PSGL-1 peptide column #2 chromatogram of purified rat liver TPST. TPST eluted from the first PSGL-1 peptide column was applied to the column and the column was eluted with 0.3 M NaCl followed by a linear 0.3 to 1M NaCl gradient in buffer B. B shows a SDS-PAGE analysis of PSGL-1 peptide column fractions of the rat liver TPST. Aliquots of the indicated fractions were electrophoresed on SDS 10% polyacrylamide gels under reducing conditions. Proteins were visualized by silver staining. The arrow indicates the protein band that was sequenced. DF=dye front.

Fractions from the first peptide column were pooled, dialyzed, and applied to a second PSGL-1 peptide column. The column was washed, eluted with 0.3 M NaCl, and then developed with a linear 0.3 to 1 M NaCl gradient (FIG. 2A). Enzyme activity eluted as a broad peak between 0.7 and 1.0 M NaCl, resolved from the bulk of the protein. Following the second peptide column the enzyme was enriched by about 18,440-fold to a specific activity of about 2,950 units/mg with a yield of about 8%. Enzyme containing fractions eluted from the second peptide column were subjected to SDS-PAGE. This showed a major protein band at about 50 kDa that co-eluted with enzyme activity and thus was a candidate for further analysis (FIG. 2B, arrow). This polypeptide had a slightly faster electrophoretic mobility under non-reducing conditions (not shown).

The most 5' human EST clone (#116978, GeneBank Accession #T93946) had a 1795 bp insert containing an 81 nt 5' untranslated region, a 1110 nt coding region, and a 604 nt 3' untranslated region. The most 5' EST mouse TPST clone (#567635, GeneBank Accession #AA183558) had a 1560 bp insert which includes 999 nt of coding sequence and a 561 nt 3' untranslated region. Based on the sequence of the mouse EST, a primer was designed to amplify the 5' end of the cDNA from mouse liver Marathon-Ready™ cDNA (Clontech). The primers used were: top strand 5'-CCATC-CTAATACGACTCACTATAGGGC-3' (SEQ ID NO:42) (AP-1), bottom strand 5'-GCGCACAGACACTCCT-TGTCGCAG-3' (SEQ ID NO:42). The cycling parameters were: 30 cycles; denaturation, 94° C., 30 s; annealing/extension, 68° C., 3 min. A product of about 1.4 kb was gel purified, ligated into the pGEM-T, and sequenced on both strands. A full-length mouse TPST cDNA was constructed by splicing the 425 nt 5' end of the PCR product to the 1456 nt 3' end of the EST clone by blunt end ligation at a unique SspI restriction site.

The amino acid sequence and corresponding cDNA for human TPST-1 are shown in SEQ ID NO:1 and SEQ ID NO:2, respectively. The amino acid sequence and corresponding cDNA for mouse TPST-1 are shown in SEQ ID NO:3 and SEQ ID NO:4, respectively. FIG. 3, showing human TPST-1, indicates two potential sites for N-linked glycosylation (as indicated by asterisk) and the putative

TABLE I

Purification of Rat Liver Tyrosylprotein Sulfotransferase

| | Protein | | | Sulfotransferase | | | |
|---|---|---|---|---|---|---|---|
| Step | Volume ml | Concentration mg/ml | Total mg | Total Activity units | Specific Activity units/mg | Yield % | Purification - Fold |
| Tissue | | | 2,000,000 | | | | |
| Post-nuclear supernatant | 4,060 | 34.6 | 140,400 | 23,080 | 0.16 | | |
| Microsomal Extract | 3,720 | 11.6 | 43,000 | 36,510 | 0.85 | 100 | 5.3 |
| Toyopearl SP-550C | 300 | 12.6 | 3,780 | 8,880 | 2.35 | 24 | 14.7 |
| Peptide Column #1 | 60 | 0.38 | 23 | 4,600 | 200 | 13 | 1,250 |
| Peptide Column #2 | 30 | 0.026 | 0.8 | 2,360 | 2,950 | 8 | 18,440 |

Molecular Cloning of Human and Mouse TPST-1. Eluate from the second peptide column was subjected to preparative SDS-PAGE. The band of about 50 kDa was excised and subjected to in gel tryptic digestion and HPLC separation. Four peaks were selected and sequenced by automated Edman degradation. Eight additional peptide sequences were obtained by on-line ion trap LC/MS/MS sequencing. These sequences did not match known protein sequence in the NCBI database. The peptide sequences were used to perform reiterative searches of the EST database using the TBLASTN and BLASTN algorithms. Confirmatory searches were performed with the MS/MS data using the SEQUEST algorithm. Searches identified 27 human and 15 mouse ESTs which formed contigs spanning 1100 nt open reading frames. I.M.A.G.E. Consortium cDNA clones (28) were obtained (Research Genetics, Inc.) and the nucleotide sequences of both strands determined.

transmembrane domain is boxed. The mouse TPST-1 has a putative transmembrane domain which corresponds to that of the hTPST-1.

The nucleotide sequences (SEQ ID NO:2) and the corresponding amino acid (SEQ ID NO:1) of the human TPST-1 open reading frame are 89% and 96% identical to the mouse sequences SEQ ID NO:4 and SEQ ID NO:3, respectively. For both the human and mouse cDNAs, the sequences surrounding the proposed initiating ATG codons have an A in position −3 and a G in position +4, thereby conforming to Kozak consensus features. Both cDNAs have polyadenylation signals upstream from the beginning of the poly(A) tail.

The cDNAs encode TPST-1 proteins of 370 amino acids with molecular masses of 42,185 Da for the human and 42,129 Da for the mouse protein. All twelve peptide sequences from the rat protein are represented in the amino acid sequences of TPST-1. Of the 128 amino acids of rat peptide sequence, the human amino acid sequence of TPST-1 differed at only 3 positions. In the rat TPST-1 Ala$^{64}$ is a Thr, Asp$^{68}$ is an Asn, and Ser$^{17}$ is an Ala, whereas the mouse sequence differs at only one position.

All known glycosyltransferases and Golgi sulfotransferases cDNAs with the exception of heparan sulfate D-glucosaminyl 3-O-sulfotransferase, predict proteins with Type II transmembrane topology with short cytoplasmic domains and lumenal catalytic domains. Kyte-Doolittle hydrophobicity plots of human (FIG. 3) and mouse (not shown) TPST-1 reveal a prominent hydrophobic segment of 17 residues near the NH$_2$-terminus. This segment is preceded by basic residues and is not followed by a suitable signal peptidase cleavage site. This indicates that TPST has Type II transmembrane topology and therefore predicts that the catalytic domain resides in the lumen of the Golgi. This prediction is supported by the observation that TPST activity in rat liver microsomes is detectable only after detergent lysis of the microsomes. Both polypeptides are predicted to have six lumenal cysteine residues and two potential sites for the addition of N-linked glycans. No other protein motifs were found by the MOTIFS program (Genetics Computer Group, Inc.).

Expression of Recombinant TPST-1 in Mammalian Cells. Human TPST-1 was expressed in CHO-K1 and 293-T cells using a vector modified for expression of fusion proteins with an NH$_2$-terminal HPC4 epitope. Cells transfected with empty plasmid or plasmid encoding human TPST-1-HPC4 were extracted and assayed for TPST activity and protein content. Compared to mock transfected cells, TPST activity was overexpressed by a factor of 9-fold in CHO-K1 and 80-fold in 293-T cells transfected with human TPST-1 cDNA. Mouse TPST-1 expressed in 293-T cells using the unmodified pcDNA3.1(+) vector was overexpressed by 74-fold (Table 2). Of note is that the specific activity of TPST-1 in mock-transfected cells is comparable to the specific activity observed in the post-nuclear supernatant of rat liver homogenate. TPST activity was not detectable in cell-free conditioned media of CHO-K1 and 293-T cells transfected with empty plasmid or plasmid encoding mouse or human TPST-1.

TABLE II

Expression of Recombinant Human TPST-1-HPC4 Fusion Protein in Mammalian Cells

| Cell Line | Transfection | Specific Activity units/mg | Induction - Fold |
|---|---|---|---|
| CHO-K1 | Mock | 0.25 ± 0.11 (3) | — |
| " | hTPST-1-HPC4 | 2.31 ± 0.89 (3) | 9 |
| 293-T | Mock | 0.11 ± 0.03 (9) | — |
| " | hTPST-1-HPC4 | 8.84 ± 1.53 (5) | 80 |
| | mTPST-1 | 8.10 ± 1.37 (4) | 74 |

Extracts of CHO-K1 and 293-T cells transfected with the indicated construct were prepared as described in Methods. Extracts were assayed for protein content and TPST activity in duplicate. Induction of TPST activity was calculated according to the ratio of the mean specific activity of TPST transfected vs. the mean specific activity of mock transfected extracts. The number of independent experiments is indicated in parentheses. Values are the mean ± SD of the indicated number of independent experiments.

Figure 4:
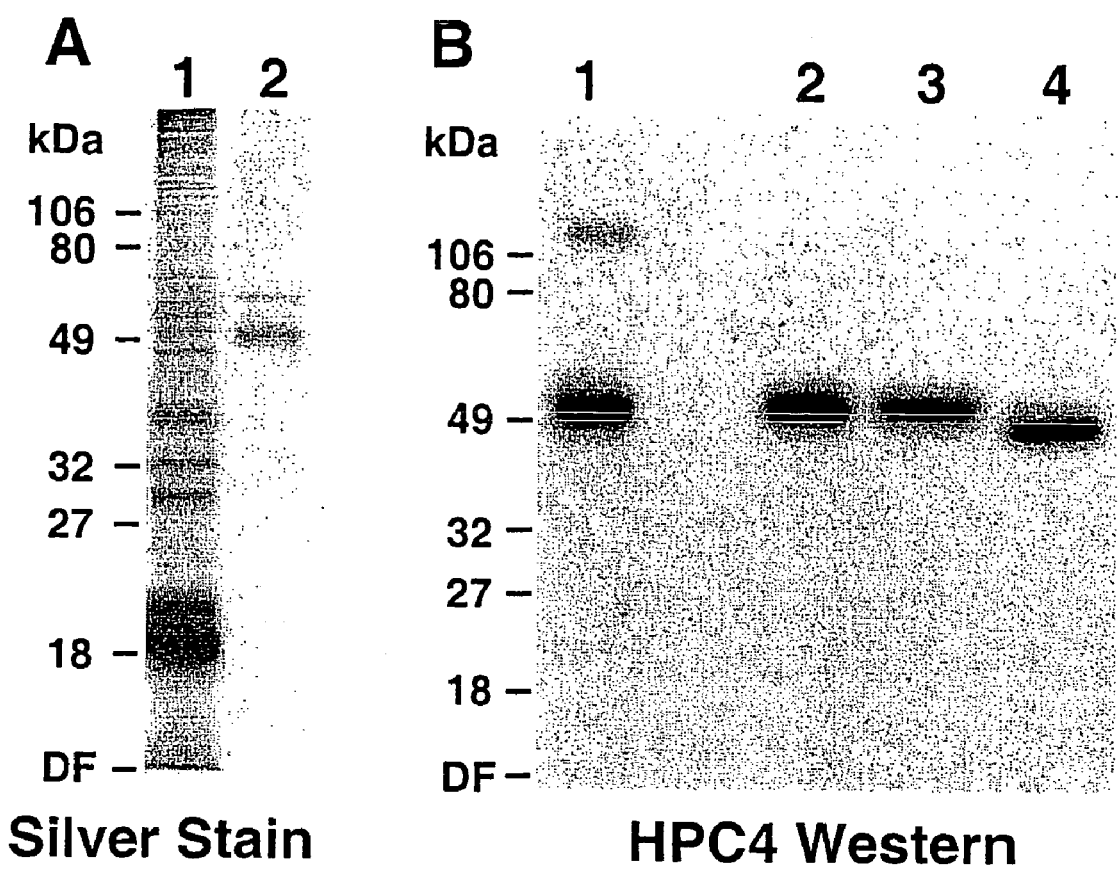
FIG. 4 shows a characterization of recombinant human TPST-1. Human TPST-1-HPC4 fusion protein was transiently expressed in 293-T cells and purified. A. Extracts of transfected cells (lane 1) and purified fusion protein (lane 2) were electrophoresed on 10% SDS polyacrylamide gels under reducing conditions and proteins visualized by silver staining. B. Purified TPST-1-HPC4 was electrophoresed on 10% SDS polyacrylamide gels under non-reducing (lane 1) and reducing (lane 2-4) conditions. Additional samples were either sham-treated (lane 3), or treated with peptide N-glycosidase F (lane 4). Fusion proteins were visualized by Western blotting using HPC4. DF=dye front.

Purification and Characterization of Recombinant Human TPST-1. To demonstrate that TPST-1 was encoded by the transfected cDNA, TPST-1-HPC4 fusion protein was purified from extracts of 293-T cells. Using HPC4 affinity chromatography, the TPST-1 fusion protein was enriched approximately 750-fold to a specific activity of about 6,300 u/mg. Silver staining of a reduced SDS polyacrylamide gel revealed a major protein of about 54 kDa and a minor contaminant with slightly slower electrophoretic mobility (FIG. 4A). Western blot analysis of non-reduced and reduced TPST-1-HPC4 revealed a single polypeptide with calculated molecular weights of 48 kDa under non-reducing and 54 kDa under reducing conditions (FIG. 4B). The slower electrophoretic mobility of TPST-1 under reducing conditions indicates that TPST contains disulfide bonds. A minor HPC4-reactive protein of about 100 kDa was observed under non-reducing, that likely represents TPST dimer. In addition, purified TPST-1 was treated with peptide N-glycosidase F and analyzed by SDS-PAGE followed by Western blotting using HPC4 (FIG. 4B). Peptide N-glycosidase F treatment resulted in a decrease of about 7 kDa in the apparent molecular weight of recombinant TPST-1, consistent with the removal of one or two complex N-linked glycans.

Figure 5:
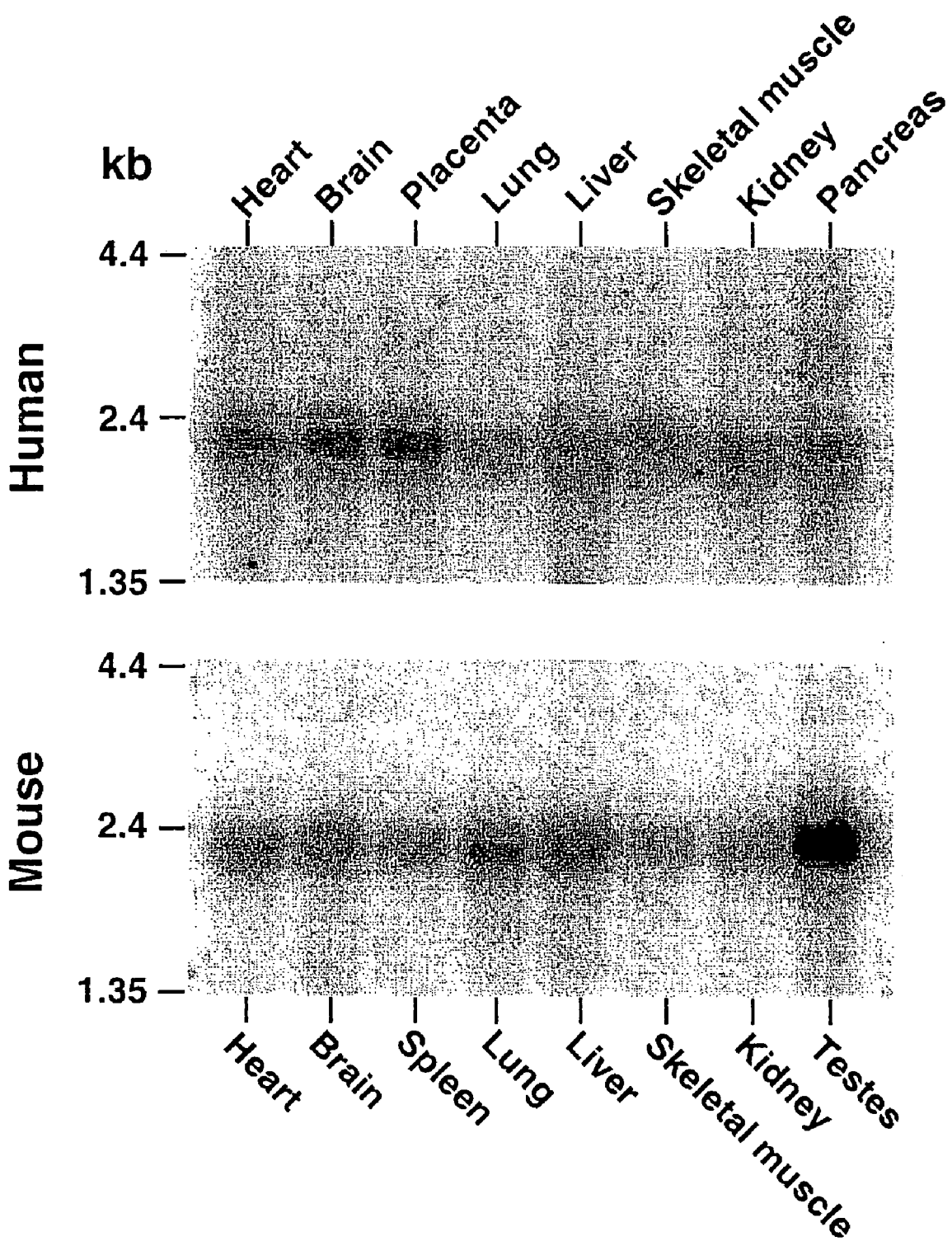
FIG. 5 shows a Northern blot analysis of poly(A)$^+$ mRNA from multiple human and mouse tissues probed with $^{32}$P-labeled partial cDNA probes from TPST-1.

Northern Blot Analysis. Northern blots were probed with $^{32}$P-labeled cDNA probes to determine the pattern of mRNA expression. This analysis showed a single transcript of about 1.8-2.0 kb in all human and mouse tissues examined (FIG. 5). The tissue sources of the overlapping EST clones from the human (brain, liver/spleen, heart, placenta, uterus, and adipose tissue) and mouse (brain, thymus, mammary gland, spleen, and testis) are consistent with a widespread tissue distribution of TPST transcripts.

Molecular Cloning of Human and Mouse TPST-2. The nucleotide and predicted amino acid sequences for human and mouse TPST-1 were used to perform reiterative searches of the EST database using the TBLASTN and BLASTN algorithms. Excluding ESTs that aligned with TPST-1, we identified 17 human EST sequences from 14 independent cDNA clones and 23 mouse EST sequences from 22 independent cDNA clones. These were aligned into separate contigs using the AssemblyLIGN program (Oxford Molecular Group PLC, Oxford, U.K.) The human and mouse TPST-2 contigs spanned open reading frames 1131 and 1128 nucleotides in length, respectively. I.M.A.G.E. Consortium cDNA clones (28) were purchased from Research Genetics (Huntsville, Ala.) and the nucleotide sequences of both strands determined by automated sequencing.

The most 5' mouse TPST-2 EST clone (clone 569461, GeneBank Accession No. AA369474) had a 1760-bp insert containing a 156-nucleotide 5' untranslated region, a 1128-nucleotide coding region, and a 476-nucleotide 3' untranslated region. The most 5' human TPST-2 EST clone (clone 810937, GeneBank Accession No. AA459614) had a 1854-bp insert. Alignment of the nucleotide sequences of human EST clone 810937 and mouse EST clone 569461 showed that the open reading frames were 89% identical. However, the alignment indicated that the human clone had a frameshift mutation due to the deletion of a guanosine at nucleotide 1200 that would result in premature termination of translation (FIG. 7) This conclusion is supported by the following observations. An independent human TPST-2 EST clone was sequenced (clone 304478, GeneBank Accession No. W21315) and the published sequences of two additional EST clones which were aligned to this region were compared. All three ESTs did not have the frame-shift mutation (FIG. 7). In addition, a BAC (bacterial artificial chromosome) clone (445C9 GeneBank Accession No. Z95115) which contains the complete genomic sequence of the human TPST-2 gene also lacked the frame shift mutation. To construct a full-length human TPST-2 cDNA, the 1087-nucleotide 5' end of the EST clone 810937 and 768-nucleotide 3' end of the EST clone 307478 were spliced together by blunt end ligation at a unique Eco47III restriction site. Therefore the full-length human TPST-2 cDNA is 1855-bp in length and contains a 197-nucleotide 5' untranslated region, a 1131-nucleotide coding region, and a 527-nucleotide 3' untranslated region.

The amino acid sequence and corresponding cDNA for human TPST-2 are shown in SEQ ID NO:5 and SEQ ID NO:6, respectively. The amino acid sequence and corresponding cDNA for mouse TPST-2 are shown in SEQ ID NO:7 and SEQ ID NO:8. FIG. 8, showing human TPST-2, indicates two potential sites for N-linked glycosylation (as indicated by asterisk) and the putative transmembrane domain is boxed. The mouse TPST-2 has a putative transmembrane domain which corresponds to that of the hTPST-2.

The nucleotide and amino acid sequences (SEQ ID NO:6 and SEQ ID NO:5) of the human TPST-2 open reading frame are 89% and 96% identical to the mouse TPST-2 sequences (SEQ ID NO:8 and SEQ ID NO:7), respectively. The sequences surrounding the proposed initiating ATG codons have a purine in position −3 and a cytosine in position +4, thereby conforming to Kozak consensus features (39). Both cDNAs have a single polyadenylation signal upstream from the beginning of the poly(A) tail.

The human and mouse TPST-2 cDNAs encode proteins of 377 and 376 amino acids with molecular masses of 41,909 Da for the human and 42,064 Da for the mouse protein, respectively. A Kyte-Doolittle hydrophobicity plot of human TPST-2 reveals a 17 residue hydrophobic segment near the N-terminus (FIG. 8). This segment is preceded by basic residues and is not followed by a suitable signal peptidase cleavage site. This indicates that TPST-2 has type II transmembrane topology. Both polypeptides (SEQ ID NO:5 and SEQ ID NO:7) are predicted to have two potential sites for the addition of N-linked glycans and six lumenal cysteine residues. The amino acid sequences of human and mouse TPST-2 are 67% and 65% identical to human and mouse TPST-1, respectively.

Expression and characterization of Recombinant TPST-2. Full-length human and mouse TPST-2 were expressed in 293-T cells as HPC4 fusion proteins as described in Experimental Procedures. Cells transfected with empty plasmid or plasmid encoding human and mouse TPST fusion proteins were extracted and assayed for TPST activity and protein content. Extracts were assayed as discussed above using a PSGL-1 peptide substrate (QATEYEYLDYDFLPE$\underline{C}$ (SEQ ID NO:22)). The specific activity of mock transfected 293-T cell extracts was 0.06±0.01 u/mg (mean±SD, n=6). When cells were transfected with human or mouse TPST-2 cDNA, the specific activity of 293-T cell extracts increased by 112-fold (7.07±1.28 u/mg, n=3) and 46-fold (2.91±0.86 u/mg, n=5), respectively. TPST activity was not detectable in culture supernatants of cells transfected with TPST-2 cDNAs, indicating that the enzyme is not secreted in an active form even when overexpressed.

293-T cells were also transfected with cDNAs encoding soluble forms i.e., lacking the transmembrane domain, of human and mouse TPST-2 with N-terminal HPC4 epitopes. TPST assays of conditioned media indicated that TPST-2 was efficiently secreted in an active form. Conditioned media from cells transfected with soluble human TPST-2 fusion protein was analyzed by Western blotting using HPC4 and an antiserum against the C-terminal 16 amino acids of TPST-2 (FIG. 9). Both HPC4 and the C-terminal peptide antiserum detected two closely spaced polypeptides of approximately 47 and 44 kDa. This demonstrates that TPST-2 is secreted as two distinct isoforms that are not the result of proteolytic degradation. To determine the structural basis for this heterogeneity, partially purified soluble TPST-2 was either sham-treated or treated with peptide N-glycosidase F and analyzed by Western blotting using the C-terminal peptide antiserum (FIG. 9). We observed that enzyme treated TPST-2 migrated as a single polypeptide with an apparent molecular mass of about 41 kDa. This result demonstrates that soluble TPST-2 is secreted with either one or two N-glycan chains.

Substrate Specificity of TPSTs. To determine if TPST-1 and TPST-2 catalyze sulfation of other substrates, extracts of human TPST-1 and TPST-2 transfected 293-T cells were assayed using peptides modeled on tyrosine sulfation sites in heparin cofactor II (HCII) and the α chain of the fourth component of complement (C4α) as substrates. The tyrosine residues in these peptides have been directly demonstrated to be sulfated in their respective native proteins (15, 40). In parallel duplicate assays of extracts from three independent transfections, we observed that TPST-1 efficiently sulfated the PSGL-1, C4α, and HCII peptides (see SEQ ID NOS: 22-24, respectively, FIG. 10). The lower specific activity observed using the HCII peptide may be because it has only a single tyrosine, in contrast to the PSGL-1 and C4α peptides which have three. We observed that the specific activity of extracts of TPST-1 and TPST-2 transfected 293-T cell were comparable using the PSGL-1 peptide as a substrate. In contrast, the specific activity of extracts of TPST-1 transfected cells was 21-fold higher using the HCII peptide as substrate and 9-fold higher using the C4α peptide when compared to TPST-2 extracts assayed in parallel. These data indicate that TPST-1 and TPST-2 differ in their specificities toward small peptide substrates in vitro.

Northern Blot Analysis. Northern blot analysis showed a TPST-2 transcript of about 1.8-2.0 kb in all human and mouse tissues examined (FIG. 11). The larger hybridizing species observed in pancreatic tissue likely represent incompletely processed transcripts. This broad tissue distribution of TPST-2 transcripts is similar to that observed for TPST-1 (FIG. 5), suggesting that both genes are expressed in the same cells.

Chromosomal Localization of the Human and Mouse TPST-2 Genes. Searches of the NCBI database revealed that sequences matching the human TPST-2 cDNA were located in a human BAC clone 445C9, (GeneBank Accession No. Z95115). This BAC clone was sequenced at the Sanger Center (Cambridge, U.K.) and maps to chromosome 22q12.1. The TPST-2 gene is centromeric to two known genes in the BAC clone, β B1-crystallin and β A4-crystallin (FIG. 12). The TPST-2 gene is transcribed from telomere to centromere and spans about 63.4 kilobase pairs. Alignment of the cDNA and genomic sequence shows that the TPST-2 gene contains 7 exons and 6 introns. Intron 1 is unusually large (about 45.4 kb) and contains a high mobility group-1 pseudogene (41). The coding region of TPST-2 spans exons III to VI. The nucleotide sequence at the 5' donor and 3' acceptor sites of all introns conform to the GT . . . AG rule (42). There were only three nucleotides in the human TPST-2 cDNA sequence that did not match the published genomic sequence. Two are conservative substitutions in the coding region ($C^{467} \rightarrow G, T^{897} \rightarrow C$) and one is in the 3' untranslated region ($C^{1847} \rightarrow T$), 7 nucleotides 5' to the polyadenylation site.

Warden et al. reported the chromosomal mapping of 40 mouse liver cDNA clones by interspecies backcross analysis (43). One of the mapped EST clones (m1650) was partially sequenced on both strands (GeneBank Accession Nos. L11849 and L12133). These sequences are >95% identical to nucleotides 12-155 and nucleotides 1109-1544 of the mouse TPST-2 cDNA, respectively. This EST clone defines the D5Ucla3 locus located in the central region of mouse chromosome 5 (Mouse Genome Database, The Jackson Laboratories).

Identification of TPST in *Caenorhabditis elegans*. TBLASTN searches on the non-redundant NCBI database using the TPST-1 and TPST-2 cDNAs as queries, identified two overlapping *C. elegans* EST clones (yk166cl and yk363g6). These clones were obtained from Dr. Yuji Kohara (National Institute of Genetics, Mishima, Japan) and the nucleotide sequences of both strands determined. Clone yk166cl is a full-length cDNA (SEQ ID NO:10) with a 1416-bp insert comprised of 54-nucleotide 5' untranslated region, a 1140-nucleotide coding region, and a 222-nucleotide 3' untranslated region. The *C. elegans* cDNA encodes a protein (SEQ ID NO: 9) of 380 amino acids, designated herein as TPST-A. Kyte-Doolittle hydrophobicity analysis indicates that the protein has type II transmembrane topology (not shown). The polypeptide has one potential N-glycosylation site and five lumenal cysteine residues. Alignment of the amino acid sequence of the *C. elegans* protein (SEQ ID NO:9) to that of human proteins show it is 54% and 52% identical to human TPST-1 (SEQ ID NO:1) and human TPST-2 (SEQ ID NO:5), respectively (FIG. 13) and has transmembrane domains which correspond to those of hTPST-1 and hTPST-1 and hTPST-2, respectively (see heavy underlining).

FIG. 13 shows the alignment of human TPST-1, human TPST-2, *C. elegans* TPST-A, and *C. elegans* TPST-B. Sequence identity between the four TPSTs is restricted to the C-terminal portion of the proteins. The relative positions of all of the intralumenal cysteine residues in TPST-1 are conserved in TPST-2. However, in *C. elegans* TPST-A the most membrane proximal intralumenal cysteine is absent.

*C. elegans* TPST-A was expressed as a full-length protein in 293-T cells from the unmodified pcDNA3.1(+) vector. Transfection of 293-T cells with *C. elegans* TPST-A cDNA resulted in a 40-fold increase in the specific activity of the cell extracts when compared to mock transfected controls using the PSGL-1 peptide as substrate (n=2). Searches of the high throughput genomic sequence database indicates that the TPST-A is located on a YAC (yeast artificial chromosome) clone (Y111B2, GeneBank Accession No. Z98857) that is currently being sequenced at the Sanger Center, (Cambridge, U.K.). This YAC maps to the right arm of chromosome III (71-73).

Database searches also revealed a second *C. elegans* TPST gene (TPST-B). This gene is present in cosmid F42G9 (GeneBank Accession No. U00051) that was sequenced at the Genome Sequencing Center at Washington University (St. Louis, Mo.). The cosmid contains a predicted open reading frame, designated F42G9.8, which predicts a 359 amino acid polypeptide, designated herein as TPST-B, with type II transmembrane topology (not shown). BESTFIT alignment of TPST-A and TPST-B (F42G9.8) reveals a 39% identity and 62% similarity at the amino acid level. The F42G9 cosmid maps to the left arm of chromosome III.

TPST-1 and other TPSTs exhibit homology to a large family of cytosolic sulfotransferases, including phenol- and hydroxysteroid-sulfotransferases. The known members of this family contain two regions which are highly conserved throughout phlogeny, called region I and region IV (31). These regions are involved in binding of the sulfate donor PAPS (32-35). Alignment of mouse TPST-1 and mouse estrogen sulfotransferase reveals a 20% identity and 52% similarity with 19 alignment gaps, 12 of which are 3 residues in length (FIG. 6). Notably, TPST-1 has a 35 residue amino terminal extension that includes the putative non-cleavable signal peptide/membrane anchor. In the estrogen sulfotransferase crystal structure, the residues which contact the 5' phosphate of PAPS (PKSGTTW (SEQ ID NO:44)) form a loop between β-sheet 3 and α-helix 3, which corresponds to region 1 (35). This region is highly conserved in TPST-1, TPST-2, TPST-A, and TPST-B, and corresponds to residues 78-84 (PRSGTTL (SEQ ID NO:45)) in TPST-1, residues 77-83 in TPST-2, residues 78-84 in TPST-A, and residues 94-100 in TPST-B (see FIG. 13). The residues involved in binding the 3' phosphate of PAP are located in two discontinuous regions of estrogen sulfotransferase. The first region includes two residues, $Arg^{130}$ and $Ser^{138}$, located just before and within α-helix 6. The second is comprised of residues 257-259 (Arg-Lys-Gly). The corresponding residues in TPST-1 are $Arg^{184}$, $Ser^{192}$, $Ala^{322}$, $Lys^{323}$, and $Leu^{324}$. Thus, although the degree of identity is limited, most of the residues involved in PAPS binding in the estrogen sulfotransferase (SEQ ID NO:13) structure are predicted to be conserved in TPST (FIG. 6). TPST exhibits a similar degree of homology to Golgi sulfotransferases, including heparan sulfate 2-sulfotransferase (36), chondroitin 6-sulfotransferase (37), and the C-terminal domain of heparan sulfate N-deacetylase/N-sulfotransferase (38).

TPST Gene and Protein Sequences and Homology. It will be appreciated that the invention includes nucleotide or amino acid sequences which have substantial sequence homology with the nucleotide and amino acid sequences shown in the Sequence Listings. The term "sequences having substantial sequence homology" means those nucleotide and amino acid sequences which have slight or inconsequential sequence variations from the sequences disclosed in the Sequence Listings, i.e. the homologous sequences function in substantially the same manner to produce substantially the same polypeptides as the actual sequences. The variations may be attributable to local mutations or structural modifications. Substantially homologous sequences further include sequences having at least 50% sequence homology with the TPST polynucleotide or polypeptide sequences shown herein or other percentages as defined elsewhere herein.

As noted elsewhere herein, the present invention includes polynucleotides represented by SEQ ID NO:2, SEQ ID NO:4, SEQ ID NO:6, SEQ ID NO:8, SEQ ID NO:10 and SEQ ID NO:12, and coding sequences thereof, which encode the proteins of SEQ ID NO:1, SEQ ID NO:3, SEQ ID NO:5, SEQ ID NO:7, SEQ ID NO:9, and SEQ ID NO:11, respectively.

Each polynucleotide (except SEQ ID NO:12) comprises untranslated regions upstream and downstream of the coding sequence and a coding sequence (which by convention includes the stop codon) (see Table III). Each polynucleotide further comprises a core base sequence which codes for a core amino acid sequence of each TPST enzyme.

TABLE III

TPST Base Sequences

| SEQ ID NO: | Bases of Coding Sequences | Untranslated Bases | Bases of Core Sequence |
|---|---|---|---|
| 2 | 82-1194 | 1-81, 1195-1768 | 289-1086 |
| 4 | 211-1323 | 1-210, 1324-1867 | 418-1215 |
| 6 | 198-1331 | 1-197, 1332-1855 | 402-1199 |
| 8 | 157-1287 | 1-156, 1288-1760 | 358-1155 |
| 10 | 66-1208 | 1-65, 1209-1426 | 273-1064 |
| 12 | 1-1077 | — | 256-1029 |

The coding sequence of each polynucleotide SEQ ID NO:2, SEQ ID NO:4, SEQ ID NO:6, SEQ ID NO:8, SEQ ID NO:10 and SEQ ID NO:12 encodes polypeptides of 370, 370, 377, 376, 380 and 359 amino acids, respectively (SEQ ID NO:1, SEQ ID NO:3, SEQ ID NO:5, SEQ ID NO:7, SEQ ID NO:9, and SEQ ID NO:11).

A comparison of the TPSTs identified herein revealed considerable homology in specific portions of the amino acid sequences. Each TPST of SEQ ID NO:3, SEQ ID NO:5, SEQ ID NO:7, SEQ ID NO:9, and SEQ ID NO:11 had homologous loci which had 100% identity with amino acid residues 78-84 and 156-161 of SEQ ID NO:1 (h-TPST-1). The TPSTs further had homologous loci having at least 80%, 71% and 70% identity with h-TPST-1 amino acid residues 70-105, 172-205, and 181-194, respectively (see Table IV).

TABLE IV

Homology of TPSTs with h-TPST-1 (% Identity)

| Enzyme | Subsequence of h-TPST-1 | | | | |
|---|---|---|---|---|---|
| | 78-84 | 70-105 | 156-161 | 172-205 | 181-194 |
| hTPST-2 | 100 | 88 | 100 | 93 | 100 |
| TPST-A | 100 | 91 | 100 | 81 | 71 |
| TPST-B | 100 | 80 | 100 | 71 | 79 |

A comparison of the overall homology of the TPSTs identified herein further reveals a considerable range in homology as indicated in the alignment matrices in Tables V and VI.

Table V compares the complete amino acid sequences of the various TPSTs. Human and mouse TPST-1 have 96% identity and 98% similarity. Human and mouse TPST-2 have 95% identity and 97% similarity. TPST-A and TPST-B have 39% identity and 62% similarity. Human TPST-1 and human TPST-2 have 67% identity and 79% similarity. Mouse TPST-1 and mouse TPST-2 have 65% identity and 78% similarity. Human TPST-1 and mouse TPST-2 have 65% identity and 78% similarity. Human TPST-2 and mouse TPST-1 have 67% identity and 79% similarity. Human and mouse TPST-1 each have 54% identity and 73% similarity with TPST-A. Human and mouse TPST-2 each have 52% identity and 68% similarity with TPST-A. Human and mouse TPST-1 have 36% identity, and 62% and 60% similarity with TPST-B. Human and mouse TPST-2 have 39% identity and 63% and 62% similarity with TPST-B.

TABLE V

Homology Between TPST Complete Amino Acid Sequences (% identity/% similarity)

| | hTPST-1 | mTPST-1 | hTPST-2 | mTPST-2 | TPST-A | TPST-B |
|---|---|---|---|---|---|---|
| hTPST-1 | 100 | 96/98 | 67/79 | 65/78 | 54/73 | 36/62 |
| mTPST-1 | | 100 | 67/79 | 65/78 | 54/73 | 36/60 |
| hTPST-2 | | | 100 | 95/97 | 52/68 | 39/63 |
| mTPST-2 | | | | 100 | 52/68 | 39/62 |
| TPST-A | | | | | 100 | 39/62 |
| TPST-B | | | | | | 100 |

Table VI compares the core sequences of the various TPSTs. The core amino acid sequences of human TPST-1, mouse TPST-1, human TPST-2, mouse TPST-2, TPST-A and TPST-B are, respectively, residues 70-335, 70-335, 69-334, 68-333, 70-333, and 86-343.

Human and mouse TPST-1 core sequences have 99% identity and 100% similarity. Human and mouse TPST-2 core sequences have 97% identity and 98% similarity. TPST-A and TPST-B core sequences have 45% identity and 68% similarity. Human TPST-1 and human TPST-2 core sequences have 79% identity and 88% similarity. Mouse TPST-1 and mouse TPST-2 core sequences have 79% identity and 88% similarity. Human TPST-1 and mouse TPST-2 core sequences have 78% identity and 88% similarity. Human TPST-2 and mouse TPST-1 core sequences have 79% identity and 88% similarity. Human TPST-2 and mouse TPST-1 core sequences have 67% identity and 82% similarity with TPST-A core sequence. Human and mouse TPST-2 core sequences and TPST-A have 66% and 68% identity, respectively, and 81% similarity with TPST-A core sequence. Human and mouse TPST-1 core sequences have 44% and 43% identity, respectively, and 65% similarity with TPST-B core sequence. Human and mouse TPST-2 core sequence have 47% identity and 69% similarity with TPST-B core sequence.

TABLE VI

Homology Between TPST Core Amino Acid Sequences (% identity/% similarity)

| | hTPST-1 | mTPST-1 | hTPST-2 | mTPST-2 | TPST-A | TPST-B |
|---|---|---|---|---|---|---|
| hTPST-1 | 100 | 99/100 | 79/88 | 78/88 | 67/82 | 44/65 |
| mTPST-1 | | 100 | 79/88 | 79/88 | 67/82 | 43/65 |
| hTPST-2 | | | 100 | 97/98 | 66/81 | 47/69 |
| mTPST-2 | | | | 100 | 68/81 | 47/69 |
| TPST-A | | | | | 100 | 45/68 |
| TPST-B | | | | | | 100 |

A comparison of the overall base homology of the TPST gene open reading frames (coding sequences—see Table III) and core sequences reveals a considerable range as indicated in the alignment matrices in Tables VII and VIII.

Table VII compares the complete open reading frames of the various TPSTs. The open reading frames (orf) of human and mouse TPST-1 have 89% homology (identity). Human and mouse TPST-2 orfs have 89% homology. TPST-A and TPST-B orfs have 59% homology. Human TPST-1 and human TPST-2 orfs have 67% homology. Mouse TPST-1 and TPST-2 orfs have 68% homology. Human TPST-1 and mouse TPST-2 orfs have 67% homology. Human TPST-2 and mouse TPST-1 orfs have 69% homology. Human TPST-1 orfs and mouse TPST-1 orfs have 63% and 62% homology with TPST-A orf, respectively. Human TPST-2 and mouse TPST-2 orfs have 62% homology with TPST-A orf. Human TPST-1 and mouse TPST-1 orfs have 62% and 59% homology with TPST-B orf, respectively. Human TPST-2 and mouse TPST-2 orfs have 61% and 60% homology with TPST-B orf, respectively.

TABLE VII

Base Homology Between TPST Gene Open Reading Frames (%)

| | hTPST-1 | mTPST-1 | hTPST-2 | mTPST-2 | TPST-A | TPST-B |
|---|---|---|---|---|---|---|
| hTPST-1 | 100 | 89 | 67 | 67 | 63 | 62 |
| mTPST-1 | | 100 | 69 | 68 | 62 | 59 |
| hTPST-2 | | | 100 | 89 | 62 | 61 |
| mTPST-2 | | | | 100 | 62 | 60 |

TABLE VII-continued

Base Homology Between TPST Gene Open Reading Frames (%)

| | hTPST-1 | mTPST-1 | hTPST-2 | mTPST-2 | TPST-A | TPST-B |
|---|---|---|---|---|---|---|
| TPST-A | | | | | 100 | 59 |
| TPST-B | | | | | | 100 |

Base homologies of the various TPST gene core sequences (see Table III) are shown in Table VIII. The core sequences of human and mouse TPST-1 have 90% homology (identity). Human and mouse TPST-2 gene core sequences have 90% homology. Human TPST-A and TPST-B gene core sequences have 59% homology. Human TPST-1 and TPST-2 gene core sequences have 68% homology. Mouse TPST-1 and TPST-2 gene core sequences have 69% homology. Human TPST-1 and mouse TPST-2 gene core sequences have 67% homology. Human TPST-2 and mouse TPST-1 gene core sequences have 67% homology. Human and mouse TPST-1 gene core sequences have 63% and 62% homology, with TPST-A core sequence, respectively. Human and mouse TPST-2 gene core sequences each have 62% homology with TPST-A gene core sequence. Human and mouse TPST-1 gene core sequences have 62% and 59% homology with TPST-B gene core sequence, respectively. Human and mouse TPST-2 gene core sequences each have 60% homology with TPST-B gene core sequence.

Homologies provided in Tables V-VIII were calculated by BESTFIT, a program component of the Wisconsin Sequence Analysis Package Version 8.0 by the Genetics Computer Group at University Research Park, 575 Science Dr., Madison, Wis. 53711.

The term "identity" or "homology" used herein is defined by the output called "Percent Identity" of a computer alignment program called BESTFIT. "Similarity" values provided herein are also provided as an output of the BESTFIT program using the alignment values provided below. As noted, this program is a component of widely used package of sequence alignment and analysis programs called Wisconsin Package Version 8.0, Genetics Computer Group (GCG), Madison, Wisc. The BESTFIT program has two alignment variables, the gap creation penalty and the gap extension penalty, which can be modified to alter the stringency of a nucleotide and/or amino acid alignment produced by the program. The settings for gap creation penalty and gap extension penalty used herein to define identity were as follows:

For amino acid alignments:
Gap creation penalty=3.000
Gap extension penalty=0.100
For nucleotide alignments:
Gap creation penalty=50
Gap extension penalty=3

The program used the PAM 250 scoring matrix. Other parameter values used in the percent identity determination were default values previously established for the 8.0 version of the BESTFIT program. (see Schwartz, R. M. and Dayhoff, M. O., [1979] in Atlas of Protein Sequence and Structure, Dayhoff, M. O. Ed., pp. 353-358, National Biomedical Research Foundation, Washington, D.C.).

TABLE VIII

Base Homology Between TPST Gene Core Sequences (%)

| | hTPST-1 | mTPST-1 | hTPST-2 | mTPST-2 | TPST-A | TPST-B |
|---|---|---|---|---|---|---|
| hTPST-1 | 100 | 90 | 68 | 67 | 63 | 62 |
| mTPST-1 | | 100 | 70 | 69 | 62 | 59 |
| hTPST-2 | | | 100 | 90 | 62 | 60 |
| mTPST-2 | | | | 100 | 62 | 60 |
| TPST-A | | | | | 100 | 59 |
| TPST-B | | | | | | 100 |

In general, polynucleotides which encode tyrosylprotein sulfotransferases are contemplated by the present invention. In particular, the present invention contemplates DNA sequences having SEQ ID NO: 2, SEQ ID NO:4, SEQ ID NO:6, SEQ ID NO:8, SEQ ID NO:10, and SEQ ID NO:12, and DNA sequences comprising bases 82-1194 of SEQ ID NO:2, bases 211-1323 of SEQ ID NO:4, bases 198-1331 of SEQ ID NO:6, bases 157-1287 of SEQ ID NO:8, bases 66-1208 of SEQ ID NO:10 and bases 1-1077 of SEQ ID NO:12. The invention further comprises portions of said sequences which encode soluble forms of TPSTs.

The invention further contemplates DNA sequences comprising bases 289-1086 of SEQ ID NO:2, bases 418-1215 of SEQ ID NO:4, bases 402-1199 of SEQ ID NO:6, bases 358-1155 of SEQ ID NO:8, bases 273-1064 of SEQ ID NO:10, and bases 256-1029 of SEQ ID NO:12, which DNA sequences comprise portions of polynucleotides which encode proteins having tyrosylprotein sulfotransferase activity.

The invention further contemplates polynucleotides which are at least about 50% homologous, 60% homologous, 70% homologous, 80% homologous, 90% homologous, or 95% homologous to the coding sequences of SEQ ID NO:2 or SEQ ID NO:4 (see Table III) where homology is defined as strict base identity, wherein said polynucleotides encode proteins having tyrosylprotein sulfotransferase activity.

The invention further contemplates polynucleotides comprising sequences which are at least about 50% homologous, 60% homologous, 70% homologous, 80% homologous, 90% homologous, or 95% homologous to the core sequences of SEQ ID NO:2 or SEQ ID NO:4 (see Table III) where homology is defined as strict base identity, and wherein said polynucleotides encode proteins having tyrosylprotein sulfotransferase activity.

The present invention further contemplates nucleic acid sequences which differ in the codon sequence from the nucleic acids defined herein due to the degeneracy of the genetic code, which allows different nucleic acid sequences to code for the same protein as is further explained herein above and as is well known in the art. The polynucleotides contemplated herein may be DNA or RNA. The invention further comprises DNA or RNA nucleic acid sequences which are complementary to the sequences described above.

The present invention further comprises polypeptides which are encoded by the polynucleotide sequences described above. In particular, the present invention contemplates polypeptides having tyrosylprotein sulfotransferase activity including SEQ ID NO: 1, SEQ ID NO:3, SEQ ID NO:5, SEQ ID NO:7, SEQ ID NO:9, and SEQ ID NO:11 and versions thereof which lack the transmembrane domain and which are therefore soluble. The invention further contemplates polypeptides which are at least 36% homologous, 50% homologous, 65% homologous, 80% homologous, 90% homologous, or 95% homologous to the polypeptides represented herein by SEQ ID NO:1 or SEQ ID NO:3, wherein homology is defined as strict identity. The invention further contemplates polypeptides which are 40% homologous, 45% homologous, 65% homologous, 70% homologous, 75% homologous, 80% homologous, 85% homologous, 90% homologous, or 95% homologous to the polypeptide represented herein by a core sequence (residues 70-335) of SEQ ID NO:1 or SEQ ID NO:3.

The present invention further contemplates polypeptides, and polynucleotides which encode such polypeptides, having loci in substantially homologous positions which have at least 94% or greater identity with residues 70-105, or residues 172-205, and 78% or greater identity with residues 181-194 of SEQ ID NO:1, and which have tyrosylprotein sulfotransferase activity or polypeptides, or polynucleotides, or polynucleotides which encode such polypeptides, having amino acid residues 76-93, 96-102, 156-162, 184-188, 196-200, 202-205, 239-245, and 330-336 of SEQ ID NO:1, and which have tyrosylprotein sulfotransferases activity.

The present invention further contemplates polypeptides which differ in amino acid sequence from the polypeptides defined herein by substitution with functionally equivalent amino acids, resulting in what are known in the art as conservative substitutions, as discussed above herein.

Also included in the invention are DNA sequences which hybridize to the DNA sequences set forth in SEQ ID NO:2, SEQ ID NO:4, SEQ ID NO:6; SEQ ID NO:8, SEQ ID NO:10 or SEQ ID NO:12, or their complementary sequences, under conditions of high or low stringency (as well known by those of ordinary skill in the art) and which encode proteins having tyrosylprotein sulfotransferases activity.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein (expressly entirely incorporated herein by reference). The conditions of temperature and ionic strength determine the "stringency" of the hybridization.

In one embodiment, high stringency conditions are prehybridization and hybridization at 68° C., washing twice with 0.1×SSC, 0.1% SDS for 20 minutes at 22° C. and twice with 0.1×SSC, 0.1% SDS for 20 minutes at 50° C. Hybridization is preferably overnight.

In another embodiment, low stringency conditions are prehybridization and hybridization at 68° C., washing twice with 2×SSC, 0.1% SDS for 5 minutes at 22° C., and twice with 0.2×SSC, 0.1% SDS for 5 minutes at 22° C. Hybridization is preferably overnight.

In an alternative embodiment, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures.

The carrier material is then washed three times each for 15 minutes using 2×SSC, 0.2% SDS preferably at least 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

In summary, as shown herein, at least four mammalian tyrosylprotein sulfotransferases and two C. elegans tyrosylprotein sulfotransferases that catalyze tyrosine O-sulfation have been cloned and expressed. These enzymes catalyze tyrosine O-sulfation of a variety of protein substrates involved in diverse physiologic functions.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides are approximate and are used as examples for the purpose of description.

Changes may be made in the construction and the operation of the various components, elements and assemblies described herein or in the steps or the sequence of steps of the methods described herein without departing from the spirit and scope of the invention as defined in the following claims.

Various references are cited herein, the disclosures of which are incorporated by reference herein in their entirety.

REFERENCES CITED

1. Huttner, W. B. (1982) *Nature* (London) 299, 273-276.
2. Huttner, W. B. & Baeuerle, P. A. (1988) *Mod. Cell Biol.* 6, 97-140.
3. Niehrs, C., Beibwanger, R. & Huttner, W. B. (1994) *Chem. Biol. Interact.* 92, 257-271.
4. Bundgaard, J. R., Vuust, J. & Hehfeld. J. F. (1997) *J. Biol. Chem.* 272, 21700-21705.
5. Baeuerle, P. A. & Huttner, W. B. (1987) *J. Cell. Biol.* 105, 2655-2664.
6. Rosa, P. Mantovani, S., Rosboch, R. & Huttner, W. B. (1992) *J. Biol. Chem.* 267, 12227-12232.
7. Wilkins, P. P. Moore, K. L. McEver, R. P. & Cummings, R. D. (1995) *J. Biol. Chem.*, 270, 22677-22680.
8. Hortin, G. L., Farries, T. C., Graham, J. P. & Atkinson, J. P. (1989) *Proc. Natl., Acad. Sci. USA* 86, 1338-1342.
9. Hortin, G. L. (1990) *Blood* 76, 946-952.
10. Pittman, D. D., Wang, J. H., Kaufman, R. J. (1992) *Biochemistry* 31, 3315-3325.
11. Leyte, A., van Schijndel, H. B., Niehrs, C., Huttner, W. B., Ph. Verbeet, M., Mertens, K. & van Mourik, J. A. (1991) *J. Biol. Chem.* 266, 740-746.
12. Dong, J. F., Li, C. Q. & Lopez, J. A. (1994) *Biochemistry* 33, 13946-13953.
13. Marchese, P. Murata, M., Mazzucato, M., Pradella, P., De Marco, L., Ware, J. & Ruggeri, Z. M. (1995) *J. Biol. Chem.* 270, 9571-9578.
14. Hortin, G., Fok, K. F., Toren, P. C. & Strauss, A. W. (1987) *J. Biol. Chem.* 262, 3082-3085.
15. Hortin, G. Tollefsen, D. M. & Strauss, A. W. (1986) *J. Biol. Chem.* 261, 15827-15830.
16. Stone, S. R., Hofsteenge, J. (1986) *Biochemistry* 25, 4622-4628.
17. Skrzypczak-Jankun, E., Carperos, V. E. Ravichandran, K. G. & Tulinsky, A. (1991) *J. Mol. Biol.* 221, 1379-1393.
18. Niehrs, C. Kraft, M. Lee, R. W. H. & Huttner, W. B. (1990) *J. Biol. Chem* 265, 8525-8532.

19. Rens, D. S. & Roth, J. A. (1989) *J. Biol. Chem.* 264, 899-905.
20. Niehrs, C. & Huttner, W. B. (1990) *EMBO J.* 9, 35-42.
21. William, S., Ramaprasad, P. & Kasinathan, C. (1997) *Arch. Biochem. Biophys.* 338, 90-96.
22. Pouyani, T. & Seed, B. (1995) *Cell* 83, 333-343.
23. Sako, D., Comess, K. M., Barone, K. M., Camphausen, R. T., Cumming, D. A. & Shaw, G. D. (1995) *Cell* 83, 323-331.
24. Zeigler, D. M. & Pettit, F. H. (1966) *Biochemistry* 5, 2932-2938.
25. Eng, J. K., McCormick, A. L. & Yates, J. R. III (1994) *J. Am. Soc. Mass Spectrom.* 5, 976-989.
26. Lane, W. S., Galat, A., Harding, M. W. & Schreiber, S. L. (1991) *J. Protein Chem.* 10, 151-160.
27. Stearns, D. J., Kurosawa, S., Sims, P. J., Esmon, N. L. & Esmon, C. T. (1988) *J. Biol. Chem.* 263, 826-832.
28. Lennon, G., Auffray, C., Polymeropoulos, M. & Soares, M. B. (1996) *Genomics* 33, 151-152.
29. Shworak, N. W., Liu, J., Fritze, L. M. S., Schwartz, J. J., Zhang, L., Logeart, D. & Rosenberg, R. D. (1997) *J. Biol. Chem.* 272, 28008-28019.
30. Lee, R. W. H. & Huttner, W. B. (1985) *Proc. Natl. Acad. Sci. USA* 82, 6143-6147.
31. Weinshilboum, R. M., Otterness, D. M., Sksoy, I. A., Wood, T. C., Her, C. & Raftogianis, R. B. (1997) *FASEB J.* 11, 3-14.
32. Komatsu, K., Driscoll, W. J., Koh, Y. & Strott, C. A. (1994) *Biochem. Biophys. Res. Commun.* 198, 1119-1127.
33. Marsolais, F. & Varin, L. (1995) *J. Biol. Chem.* 270, 30458-30463.
34. Driscoll, W. J., Komatsu, K. & Strott, C. A. (1995) *Proc. Natl. Acad. Sci. U.S.A.* 92, 12328-12332.
35. Kakuta, Y., Pedersen, L. G., Carter, C. W., Negishi, M. & Pedersen, L. C. (1997) *Nature Struct. Biol.* 4, 904-908.
36. Kobayashi, M., Habuchi, H., Yoneda, M., Habuchi, O. & Kimata, K. (1997) *J. Biol. Chem.* 272, 13980-13985.
37. Fukata, M., Uchimura, K., Nakashima, K., Kato, M., Kimata, K., Shinomura, T. & Habuchi, O. (1995) *J. Biol. Chem.* 270, 18575-18580.
38. Hashimoto, Y., Orellana, A., Gil, G. & Hirschberg, C. B. (1992) *J. Biol. Chem.* 267, 15744-15750.
39. Kozak, M (1987) *Nucl. Acids Res.* 15, 8125-8148.
40. Horin, G., Sims, H., and Strauss, A. W. (19860 *J. Biol. Chem.* 261, 1786-1793.
41. Ferrari, S., Finelli, P., Rocchi, M., and Bianchi, M. E. (1996) *Genomics* 35, 367-371.
42. Breathnach, R. and Chambon, P. (1981) *Annu. Rev. Biochem.* 50, 349-383.
43. Warden, C. H., Mehrabian, M., He, K. Y., Yoon, M. Y., Diep, A., Xia, Y. R., Wen, P. Z., Svenson, K. L., Sparkes, R. S., and Lusis, A. J. (1993) *Genomics* 18, 295-307.

---

What is claimed is:

1. A method of determining whether a candidate compound is a modulator of tyrosylprotein sulfotransferase activity comprising:

(a) contacting a candidate compound with a purified or recombinant tyrosylprotein sulfotransferase under conditions suitable for causing transfer of sulfate from a sulfate donor to a tyrosine of a protein, polypeptide or peptide, wherein said tyrosylprotein sulfotransferase is encoded by a polynucleotide selected from the group consisting of:

(i) a polynucleotide which hybridizes to a nucleic acid sequence comprising nucleotides 198-1331 of SEQ ID NO:6;

(ii) a polynucleotide which hybridizes to a nucleic acid sequence comprising nucleotides 402-1199 of SEQ ID NO:6;

(iii) a polynucleotide encoding a polypeptide comprising the amino acid sequence encoded by nucleotides 198-1331 of SEQ ID NO:6; and (iv) a polynucleotide encoding a polypeptide comprising the amino acid sequence encoded by nucleotides 402-1199 of SEQ ID NO:6, and wherein the polynucleotides of (i) and (ii) hybridize under hybridization conditions comprising: incubation at 68° C. overnight followed by washing twice with two times SSC, 0.1% SDS at 22° C., and washing twice with 0.1 times SSC, 0.1% SDS at 50° C.; and (b) determining whether said candidate compound modulates the activity of said tyrosylprotein sulfotransferase, wherein said determining step further comprises measuring a level of tyrosylprotein sulfotransferase activity, wherein a level of tyrosylprotein sulfotransferase activity in the presence of said candidate compound that is modulated relative to tyrosylprotein sulfotransferase activity in the absence of said candidate compound is indicative of tyrosylprotein sulfotransferase modulatory activity of said candidate compound.

2. The method of claim 1, wherein said contacting step further comprises combining the candidate compound and the tyrosylprotein sulfotransferase with a sulfate donor and a protein, polypeptide, or peptide under conditions suitable for causing transfer of the sulfate from the sulfate donor to the tyrosine of the protein, polypeptide, or peptide thereby forming a sulfated protein, polypeptide or peptide.

3. The method of claim 1, wherein said determining step further comprises measuring a level of tyrosylprotein sulfotransferase activity, wherein a level of tyrosylprotein sulfotransferase activity in the presence of said candidate compound that is modulated relative to tyrosylprotein sulfotransferase activity in the absence of said candidate compound is indicative of tyrosylprotein sulfotransferase modulatory activity of said candidate compound.

4. The method of claim 3, wherein said determining step further comprises measuring a level of tyrosylprotein sulfotransferase activity, wherein a level of tyrosylprotein sulfotransferase activity in the presence of said candidate compound that is decreased relative to tyrosylprotein sulfotransferase activity in the absence of said candidate compound is indicative of tyrosylprotein sulfotransferase inhibitory activity of said candidate compound.

5. The method of claim 3, wherein said step of measuring a level of tyrosylprotein sulfotransferase activity further comprises measuring the quantity of said protein, polypeptide or peptide which has been sulfated.

6. The method of claim 3, wherein said step of measuring a level of tyrosylprotein sulfotransferase activity further comprises the steps of adding one or more reaction terminating reagents and measuring the quantity of said protein, polypeptide or peptide which has been sulfated.

7. The method of claim 3, wherein said step of measuring a level of tyrosylprotein sulfotransferase activity further comprises measuring the quantity of sulfate that has been transferred to said protein, polypeptide or peptide.

8. The method of claim 1, wherein said conditions are suitable for causing a linear reaction rate for the transfer of sulfate from a sulfate donor to the tyrosine of a protein, polypeptide or peptide.

9. The method of claim 1, wherein said tyrosylprotein sulfotransferase comprises the amino acid sequence of SEQ ID NO:5.

10. The method of claim 1, wherein said tyrosylprotein sulfotransferase comprises the amino acid sequence amino acids 69-334 of SEQ ID NO:5.

11. The method of claim 1, wherein said tyrosylprotein sulfotransferase lacks a transmembrane domain.

12. The method of claim 1, wherein said tyrosylprotein sulfotransferase is recombinant tyrosylprotein sulfotransferase.

13. The method of claim 12, wherein said recombinant tyrosylprotein sulfotransferase is prepared by a method comprising the steps of:
(i) culturing a host cell transformed or transfected with an expressible polynucleotide encoding the tyrosylprotein sulfotransferase; and
(ii) expressing in the cultured host cell the tyrosylprotein sulfotransferase.

14. The method of claim 13, wherein the expressible polynucleotide encodes a N-terminal transferrin signal peptide of SEQ ID NO:39 N-terminal of the tyrosylprotein sulfotransferase sequence.

15. The method of claim 14, wherein said signal peptide is cleaved from the tyrosylprotein sulfotransferase.

16. The method of claim 1, wherein said tyrosylprotein sulfotransferase is present in a conjugate that also comprises the HPC4 epitope of SEQ ID NO:34.

17. The method of claim 1, wherein said tyrosylprotein sulfotransferase is purified using affinity chromatography.

18. The method of claim 1, wherein said tyrosylprotein sulfotransferase is expressed as a fusion protein that also comprises the HPC4 epitope of SEQ ID NO:34, and said tyrosylprotein sulfotransferase is purified using an anti-HPC4 antibody.

19. The method of claim 1, wherein the protein, polypeptide or peptide is P-selectin glycoprotein ligand-1 (PSGL-1) or a tyrosine-containing fragment thereof.

20. The method of claim 19, wherein the PSGL-1 or tyrosine-containing fragment thereof comprises SEQ ID NO:22.

21. The method of claim 1, wherein the protein, polypeptide or peptide is heparin cofactor II (HCII) or a tyrosine-containing fragment thereof.

22. The method of claim 21, wherein the HCII or tyrosine-containing fragment thereof comprises SEQ ID NO:23.

23. The method of claim 1, wherein the protein, polypeptide or peptide is the α-chain of complement factor C4 (C4α) or a tyrosine-containing fragment thereof.

24. The method of claim 23, wherein the C4α or tyrosine-containing fragment thereof comprises SEQ ID NO:24.

25. The method of claim 1, wherein the protein, polypeptide or peptide is linked to a solid support.

26. The method of claim 1, wherein steps (a) and (b) are repeated for a plurality of candidate compounds.

27. The method of claim 26, wherein said plurality is a library of candidate compounds.

28. The method of claim 27, wherein said library is selected from the group consisting of a natural product library, a chemical library, and a peptide library.

29. The method of claim 1, wherein said candidate compound is a peptide.

30. The method of claim 1, wherein said candidate compound is a polypeptide or protein.

31. A method of determining whether a member of a library of candidate compounds is a modulator of tyrosylprotein sulfotransferase activity comprising:
(a) contacting a member of a library of candidate compounds with a tyrosylprotein sulfotransferase under conditions suitable for causing transfer of sulfate from a sulfate donor to a tyrosine of a protein, polypeptide or peptide, wherein said tyrosylprotein sulfotransferase is encoded by a polynucleotide selected from the group consisting of:
(i) a polynucleotide which hybridizes to a nucleic acid sequence comprising nucleotides 198-1331 of SEQ ID NO:6;

(ii) a polynucleotide which hybridizes to a nucleic acid sequence comprising nucleotides 402-1199 of SEQ ID NO:6;
(iii) a polynucleotide encoding a polypeptide comprising the amino acid sequence encoded by nucleotides 198-1331 of SEQ ID NO:6; and
(iv) a polynucleotide encoding a polypeptide comprising the amino acid sequence encoded by nucleotides 402-1199 of SEQ ID NO:6, and wherein the polynucleotides of (i) and (ii) hybridize under hybridization conditions comprising: incubation at 68° C. overnight followed by washing twice with two times SSC, 0.1% SDS at 22° C., and washing twice with 0.1 times SSC, 0.1% SDS at 50°C.; and (b) determining whether said member of the library of candidate compounds modulates the activity of said tyrosylprotein sulfotransferase, wherein said determining step further comprises measuring a level of tyrosylprotein sulfotransferase activity, wherein a level of tyrosylprotein sulfotransferase activity in the presence of said candidate compound that is modulated relative to tyrosylprotein sulfotransferase activity in the absence of said candidate compound is indicative of tyrosylprotein sulfotransferase modulatory activity of said candidate compound.

* * * * *

UNITED STATES PATENT AND TRADEMARK OFFICE
CERTIFICATE OF CORRECTION

PATENT NO. : 7,316,912 B2  
APPLICATION NO. : 11/336497  
DATED : January 8, 2008  
INVENTOR(S) : Kevin L. Moore It is certified that error appears in the above-identified patent and that said Letters Patent is hereby corrected as shown below:

On Page 2, at Column 1, Line 7, in Other Publications section, please delete "5'Similar" and insert --5' Similar--, therefor.

On Page 2, at Column 1, Line 8, in Other Publications section, please delete "CEO7235"," and insert --CE07235",--, therefor.

On Page 2, at Column 1, Line 19, on Other Publications section, please delete "Famuily"," and insert --Family",--, therefor.

On Page 2, at Column 1, Line 22, in Other Publications section, please delete "yk166c1:5'End," and insert --yk166c1:5 End,--, therefor.

On Page 2, at Column 1, Line 23, in Other Publications section, please delete "Read,"Sep." and insert --Read," Sep.--, therefor.

On Page 2, at Column 1, Line 33, in Other Publications section, please delete "Parmacol.," and insert --Pharmacol.,--, therefor.

On Page 2, at Column 1, Line 39, in Other Publications section, please delete "CEO7235"" and insert --CE07235,"--, therefor.

On Page 2, at Column 2, Line 2, in Other Publications section, please delete "Differntial" and insert --Differential--, therefor.

On Page 2, at Column 2, Line 11, in Other Publications section, please delete "Postranslational" and insert --Posttranslational--, therefor.

UNITED STATES PATENT AND TRADEMARK OFFICE
CERTIFICATE OF CORRECTION

PATENT NO. : 7,316,912 B2
APPLICATION NO. : 11/336497
DATED : January 8, 2008
INVENTOR(S) : Kevin L. Moore It is certified that error appears in the above-identified patent and that said Letters Patent is hereby corrected as shown below:

On Page 2, at Column 2, Line 23, please delete "263-826-832," and insert --263:826-832,--, therefor.

At Column 2, Line 10, please delete "Methods." and insert --methods.--, therefor.

At Column 3, Line 67, please delete "eukaryoties." and insert --eukaryotes.--, therefor.

At Column 4, Line 46, please delete "extra cytoplasmic" and insert --extracytoplasmic--, therefor.

At Column 8, Line 66, please delete "eurkaryotes" and insert --eukaryotes--, therefor.

At Column 9, Lines 18-19, please delete "extraccellular" and insert --extracellular--, therefor.

At Column 10, Line 57, please delete "an" and insert --a--, therefor.

At Column 11, Line 23, please delete "umbeliferone," and insert --umbelliferone,--, therefor.

At Column 11, Line 38, please delete "(Fluorengenic" and insert --(Fluorogenic--, therefor.

At Column 12, Line 7, please delete "aminos" and insert --amino--, therefor.

At Column 13, Line 54, please delete "al.,." and insert --al.,--, therefor.

UNITED STATES PATENT AND TRADEMARK OFFICE
CERTIFICATE OF CORRECTION

PATENT NO. : 7,316,912 B2
APPLICATION NO. : 11/336497
DATED : January 8, 2008
INVENTOR(S) : Kevin L. Moore It is certified that error appears in the above-identified patent and that said Letters Patent is hereby corrected as shown below:

At Column 14, Line 12, please delete "acetylchoilinesterase," and insert --acetylcholinesterase,--, therefor.

At Column 15, Line 18, please delete "recirculatary" and insert --recirculatory--, therefor.

At Column 20, Line 58, please delete "kDA." and insert --kDa.--, therefor.

At Column 23, Line 2, please delete "Ser$^{17}$" and insert --Ser$^{171}$--, therefor.

At Column 27, Line 61, please delete "phlogeny," and insert --phylogeny,--, therefor.

At Column 36, Line 18, please delete "(19860" and insert --(1986)--, therefor.

At Column 69, Line 61, in Claim 10, after "sequence" please insert --of--.

At Column 70, Line 11, in Claim 14, after "SEQ ID NO:39" please insert --,--.

Signed and Sealed this

Twenty-eighth Day of October, 2008

JON W. DUDAS
*Director of the United States Patent and Trademark Office*